United States Patent
Sawchuk

(10) Patent No.: US 12,274,556 B2
(45) Date of Patent: *Apr. 15, 2025

(54) MEDICAL DEVICE AND METHOD FOR PREDICTING CARDIAC EVENT SENSING BASED ON SENSING CONTROL PARAMETERS

(71) Applicant: Medtronic, Inc., Minneapolis, MN (US)

(72) Inventor: Robert T. Sawchuk, Roseville, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/482,913

(22) Filed: Oct. 8, 2023

(65) Prior Publication Data

US 2024/0032846 A1 Feb. 1, 2024

Related U.S. Application Data

(63) Continuation of application No. 17/391,855, filed on Aug. 2, 2021, now Pat. No. 11,779,255.

(60) Provisional application No. 63/060,773, filed on Aug. 4, 2020.

(51) Int. Cl.
| | |
|---|---|
| A61B 5/363 | (2021.01) |
| A61B 5/00 | (2006.01) |
| A61B 5/29 | (2021.01) |
| A61B 5/339 | (2021.01) |
| A61B 5/361 | (2021.01) |
| A61N 1/362 | (2006.01) |
| A61N 1/39 | (2006.01) |

(52) U.S. Cl.
CPC .............. *A61B 5/363* (2021.01); *A61B 5/29* (2021.01); *A61B 5/339* (2021.01); *A61B 5/7264* (2013.01); *A61B 5/7282* (2013.01); *A61B 5/361* (2021.01); *A61B 5/4836* (2013.01); *A61B 2560/02* (2013.01); *A61N 1/362* (2013.01); *A61N 1/39622* (2017.08)

(58) Field of Classification Search
CPC ........... A61B 5/363; A61B 5/29; A61B 5/339; A61B 5/7282; A61N 1/3621
See application file for complete search history.

(56) References Cited

U.S. PATENT DOCUMENTS

| | | |
|---|---|---|
| 5,507,782 A | 4/1996 | Kieval et al. |
| 6,266,555 B1 | 7/2001 | Werner et al. |
| 6,301,503 B1 | 10/2001 | Hsu et al. |

(Continued)

*Primary Examiner* — Catherine M Voorhees

(57) ABSTRACT

A medical device is configured to receive sensed cardiac event data including a value of a feature determined from each one of a plurality of cardiac events sensed from a cardiac signal according to a first setting of a sensing control parameter. The medical device is configured to classify each value of the feature of each one of the sensed cardiac events as either a predicted sensed event or a predicted undersensed event according to a second setting of the sensing control parameter that is less sensitive to sensing cardiac events than the first setting. The medical device is configured to determine a predicted sensed event interval between each consecutive pair of the predicted sensed events and predict that an arrhythmia is detected or not detected based on the predicted sensed event intervals.

21 Claims, 22 Drawing Sheets

(56) References Cited

U.S. PATENT DOCUMENTS

| | | | |
|---|---|---|---|
| 7,496,403 B2 | 2/2009 | Cao et al. | |
| 8,135,456 B2 | 3/2012 | Halluska | |
| 8,521,269 B1 | 8/2013 | Gunderson et al. | |
| 10,252,071 B2 | 4/2019 | Cao et al. | |
| 10,463,314 B1 * | 11/2019 | Najarian | G16H 50/30 |
| 10,675,478 B2 | 6/2020 | Marshall et al. | |
| 11,779,255 B2 * | 10/2023 | Sawchuk | A61B 5/7264 |
| | | | 600/515 |
| 2007/0049982 A1 * | 3/2007 | Cao | A61N 1/371 |
| | | | 607/27 |
| 2011/0112597 A1 | 5/2011 | Snell et al. | |
| 2013/0261479 A1 * | 10/2013 | Kemppainen | A61B 5/355 |
| | | | 600/517 |
| 2017/0312534 A1 * | 11/2017 | Cao | A61N 1/3956 |
| 2019/0133457 A1 * | 5/2019 | Sun | A61B 5/0205 |

* cited by examiner

|  |  | SENSITIVITY | | |
|---|---|---|---|---|
|  |  | PROGRAMMED | TEST | TEST |
|  |  | 0.075 mV | 0.9 mV | 1.2 mV |
| EVENT | RRI | MAX PEAK AMP | PREDICTED | |
| VF1 | 235 | 1.88 | S | S |
| VF2 | 225 | 1.38 | S | S |
| VF3 | 228 | 1.7 | S | S |
| VF4 | 242 | 1.19 | S | U |
| VF5 | 233 | 0.75 | U | U |
| VF6 | 242 | 0.78 | U | U |
| VF7 | 258 | 2.06 | S | S |
| VF8 | 282 | 1.34 | S | S |
| VF9 | 265 | 2.44 | S | S |
| VF10 | 213 | 1.99 | S | S |
| VF11 | 240 | 1.49 | S | S |
| VF12 | 235 | 1.71 | S | S |
| VF13 | 250 | 1.22 | S | S |
| VF14 | 227 | 1.52 | S | S |
| VF15 | 243 | 1.24 | S | S |
| VF16 | 242 | 1.62 | S | S |
| VF17 | 203 | 1.68 | S | S |
| VF18 | 217 | 1.1 | S | U |
| VF19 | 275 | 0.96 | S | U |
| VF20 | 250 | 1.48 | S | S |
| VF21 | 233 | 1.14 | S | U |
| VF22 | 315 | 1.11** | S | U |
| VF23 | 228 | 2.28 | S | S |
| VF24 | 202 | 0.74 | U | U |
| VF25 | 243 | 0.62 | U | U |
| VF26 | 235 | 0.99 | S | S |
| VF27 | 250 | 1.01 | S | U |
| VF28 | 225 | 1.04 | S** | U |
| VF29 | 227 | 0.81 | U | U |
| DETECTION |  |  | VF** | VF** | ND |

| SENSITIVITY (mV) | DETECTION (s) |
|---|---|
| 0.075 | ≤7 |
| 0.1 | ≤7 |
| 0.15 | 7 |
| 0.2 | 10 |
| 0.3 | 11 |
| 0.45 | 12 |
| 0.6 | 12 |
| 0.9 | 15 |
| 1.2 | NO DETECTION |

| SENSITIVITY (mV) | SAFETY MARGIN | DETECTION |
|---|---|---|
| 0.075 | >4X | Y |
| 0.1 | >4X | Y |
| 0.15 | >4X | Y |
| 0.2 | >4X | Y |
| 0.3 | 3X | Y |
| 0.45 | 2X | Y |
| 0.6 | 1X | Y |
| 0.9 | 1X | Y |
| 1.2 | 0 | N |

FIG. 14

MEDICAL DEVICE AND METHOD FOR PREDICTING CARDIAC EVENT SENSING BASED ON SENSING CONTROL PARAMETERS

REFERENCE TO RELATED APPLICATIONS

This application is a Continuation of U.S. patent application Ser. No. 17/391,855, filed Aug. 2, 2021, which claims the benefit of provisional U.S. Patent Application No. 63/060,773, filed Aug. 4, 2020, the entire content of both incorporated herein by reference.

TECHNICAL FIELD

The disclosure relates generally to a medical device and method for predicting cardiac event sensing according to different sensing control parameter settings.

BACKGROUND

Medical devices may sense electrophysiological signals from the heart, brain, nerve, muscle or other tissue. Such devices may be implantable, wearable or external devices using implantable and/or surface (skin) electrodes for sensing the electrophysiological signals. In some cases, such devices may be configured to deliver a therapy based on the sensed electrophysiological signals. For example, implantable or external cardiac pacemakers, cardioverter defibrillators, cardiac monitors and the like, sense cardiac electrical signals from a patient's heart. A medical device may sense cardiac electrical signals from a heart chamber and deliver electrical stimulation therapies to the heart chamber using electrodes carried by a transvenous medical electrical lead, a non-transvenous medical electrical lead or leadless electrodes coupled directly to the housing of the medical device.

A cardiac pacemaker or cardioverter defibrillator may deliver therapeutic electrical stimulation to the heart via electrodes carried by one or more medical electrical leads and/or electrodes on a housing of the medical device. The electrical stimulation may include signals such as pacing pulses or cardioversion or defibrillation shocks. In some cases, a medical device may sense cardiac electrical signals attendant to the intrinsic or pacing-evoked depolarizations of the heart and control delivery of stimulation signals to the heart based on sensed cardiac electrical signals. Upon detection of an abnormal rhythm, such as bradycardia, tachycardia or fibrillation, an appropriate electrical stimulation signal or signals may be delivered to restore or maintain a more normal rhythm of the heart. For example, an implantable cardioverter defibrillator (ICD) may deliver pacing pulses to the heart of the patient upon detecting bradycardia or tachycardia or deliver cardioversion or defibrillation (CV/DF) shocks to the heart upon detecting tachycardia or fibrillation.

SUMMARY

In general, the disclosure is directed to a medical device system and method for analyzing sensed cardiac event data for evaluating the sensing performance according to at least one alternative sensing control parameter setting. The sensing control parameter may be a programmable sensitivity setting used to sense intrinsic cardiac events attendant to the depolarization of the myocardial tissue, e.g., R-waves attendant to ventricular depolarization and/or P-waves attendant to atrial depolarization. A medical device system operating according to the techniques disclosed herein senses cardiac events according to a programmed sensing control parameter setting and stores a feature of each sensed cardiac event. The medical device system may classify each of the stored event features as being a predicted sensed or a predicted undersensed cardiac event based on at least one different setting of the sensing control parameter. The different setting of the sensing control parameter may be less sensitive to sensing cardiac events than the programmed sensing control parameter setting used to sense the cardiac events. The medical device system may determine when an arrhythmia detection is predicted based on the predicted sensed events and/or predict a therapy response to the predicted sensed events. For example, the medical device system may determine a time interval required to detect a tachyarrhythmia episode according to at least one different setting of the sensing control parameter for comparison to a tachyarrhythmia detection time according to the programmed sensing control parameter setting.

In one example, the disclosure provides a medical device including a processor configured to receive sensed cardiac event data. The sensed cardiac event data includes a value of a feature determined from each one of multiple cardiac events sensed from a cardiac signal according to a first setting of a sensing control parameter. The processor is configured to classify each value of the first feature as either a predicted sensed event or a predicted undersensed event according to a second setting of the sensing control parameter. The second setting is less sensitive to sensing cardiac events than the first setting. The processor is configured to determine a predicted sensed event interval between each consecutive pair of the predicted sensed events and predict that an arrhythmia is detected or not detected based on the predicted sensed event interval. The processor generates an output based on the arrhythmia detection prediction associated with the second setting of the sensing control parameter.

In another example, the disclosure provides a method that includes receiving sensed cardiac event data that includes a value of a feature determined from each one of multiple cardiac events sensed from a cardiac signal according to a first setting of a sensing control parameter. The method further includes classifying each value of the first feature as either a predicted sensed event or a predicted undersensed event according to a second setting of the sensing control parameter. The second setting is less sensitive to sensing cardiac events than the first setting. The method further includes determining a predicted sensed event interval between each consecutive pair of the predicted sensed events and predicting that an arrhythmia is detected or not detected based on the predicted sensed event intervals. The method includes generating an output based on the arrhythmia detection prediction associated with the second setting of the sensing control parameter.

In another example, the disclosure provides a non-transitory computer-readable medium storing a set of instructions which, when executed by a processor of a medical device, cause the medical device to receive sensed cardiac event data including a value of a feature determined from each one of multiple cardiac events sensed from a cardiac signal according to a first setting of a sensing control parameter and classify each value of the feature as either a predicted sensed event or a predicted undersensed event according to a second setting of the sensing control parameter. The second setting is less sensitive to sensing cardiac events than the first setting. The instructions further cause the device to determine a predicted sensed event interval between each consecutive pair of the predicted sensed events, predict that an arrhythmia is detected or not detected based on the predicted sensed event intervals, and generate an output based on the arrhythmia detection prediction associated with the second setting of the sensing control parameter.

In another example, the disclosure provides a graphical user interface system including a processor and a display unit coupled to the processor. The processor is configured to receive sensed cardiac event data including a value of a feature determined from each one of multiple cardiac events sensed from a cardiac signal according to a first setting of a sensing control parameter. The processor is configured to classify each value of the feature as one of a predicted sensed event or a predicted undersensed event according to a second setting of the sensing control parameter. The second setting is less sensitive to sensing cardiac events than the first setting. The processor is configured to determine a predicted sensed event interval between each consecutive pair of the predicted sensed events, predict that an arrhythmia is detected or not detected based on the predicted sensed event intervals; and generate an output of data corresponding to the arrhythmia detection prediction associated with the second setting of the sensing control parameter. The display unit is configured to receive the generated output of data from the processor and display a visual representation of the arrhythmia detection prediction.

This summary is intended to provide an overview of the subject matter described in this disclosure. It is not intended to provide an exclusive or exhaustive explanation of the apparatus and methods described in detail within the accompanying drawings and description below. Further details of one or more examples are set forth in the accompanying drawings and the description below.

BRIEF DESCRIPTION OF DRAWINGS

FIG. 12 is a table of sensed cardiac event data and classifications of predicted sensed and predicted undersensed events of the sensed cardiac event data according to one example.

FIG. 13 is a diagram of data that may be generated by a processor and displayed by display unit according to one example.

FIG. 14 is a diagram of another example of a data table that may be displayed by a display unit from data generated by a processor of a medical device system according to techniques disclosed herein.

DETAILED DESCRIPTION

Figure 1A:
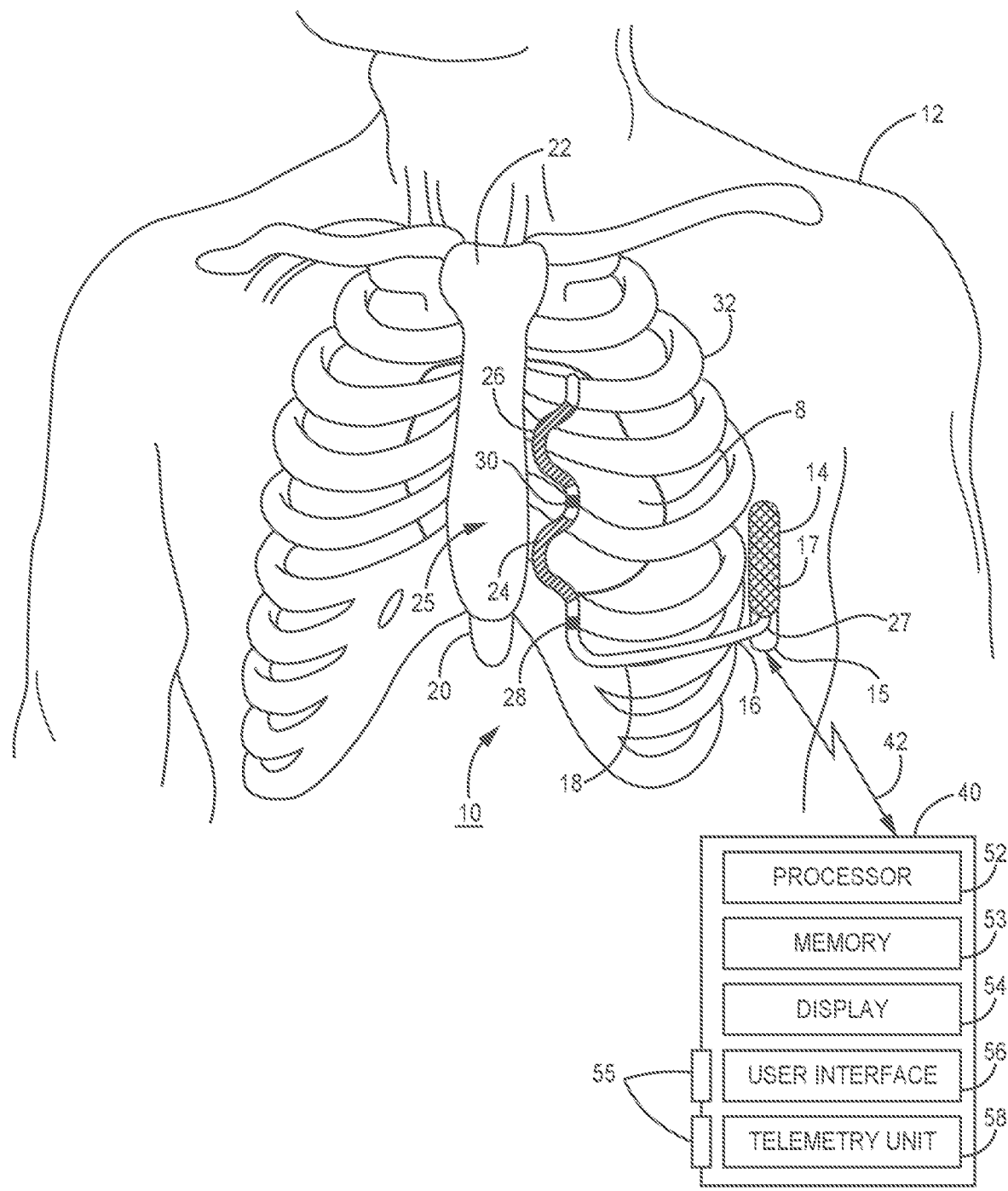
FIGS. 1A and 1B are conceptual diagrams of an ICD system configured to sense cardiac electrical events and deliver cardiac electrical stimulation therapies according to one example.

In general, this disclosure describes a medical device system and techniques for determining a rate of cardiac event signals sensed according to different settings of at least one sensing control parameter. Cardiac event signals, also referred to herein as "cardiac events," may be sensed by a medical device for determining a cardiac rate and for detecting an abnormal cardiac rhythm for providing cardiac electrical stimulation therapy as needed. The "cardiac event" being sensed is an event associated with a single cardiac cycle or heartbeat such as an R-wave attendant to ventricular depolarization or a P-wave attendant to atrial depolarization. The cardiac event may be a systolic event or diastolic event. The cardiac events may be sensed for detecting cardiac arrhythmias. For example, the rate of sensed cardiac events may be determined for detecting atrial or ventricular tachyarrhythmia, such as atrial tachycardia (AT), atrial fibrillation (AF), ventricular tachycardia (VT) or ventricular fibrillation (VF). In other examples, the rate of sensed cardiac events may be determined for controlling cardiac pacing for treating bradycardia, asystole or other abnormal rhythms or conduction abnormalities. In some examples, one or more alternative settings of the sensitivity used for sensing cardiac events are applied by a processor to sensed cardiac event data to determine which sensed cardiac events are still likely to be sensed if the sensitivity is reprogrammed to an alternative setting.

The sensed cardiac event data is determined by a medical device from cardiac events that are sensed using a programmed sensitivity setting. Using the stored sensed cardiac event data, a processor may determine new sensed event intervals according to predicted sensed or undersensed events. This determination of new cardiac event rates or intervals according to an alternative sensitivity setting may be used to determine a time of arrhythmia detection and/or therapy delivery. For example, this determination may be used to determine a time required to detect a tachyarrhythmia episode. The techniques disclosed herein for analyzing the rate and/or intervals of cardiac events according to different sensing control parameter settings may be implemented in a variety of cardiac devices configured for sensing cardiac events and determining a cardiac event interval or rate for detecting a cardiac rhythm and, in some cases, controlling a cardiac electrical stimulation therapy.

In the illustrative examples presented herein, a cardiac medical device, such as a cardiac monitor, pacemaker or ICD, is configured to sense cardiac electrical signals and deliver cardiac electrical stimulation pulses for capturing and depolarizing the myocardium. The pacemaker or ICD may be coupled to a transvenous or non-transvenous lead, or the medical device may be a leadless device in various examples. For example, the pacemaker or ICD may be coupled to an "extra-cardiovascular" lead, referring to a lead that positions electrodes outside the blood vessels, heart, and pericardium surrounding the heart of a patient. Implantable electrodes carried by extra-cardiovascular leads, for example, may be positioned extra-thoracically (outside the ribcage and sternum) or intra-thoracically (beneath the ribcage or sternum, sometimes referred to as a sub-sternal position) but may not necessarily be in intimate contact with myocardial tissue. In the examples described below in conjunction with FIGS. 1A-2C, electrodes for sensing cardiac electrical signals are carried by a lead that may be advanced to a supra-diaphragmatic position, which may be within the thoracic cavity or outside the thorax in various examples.

In other examples, the medical device may be coupled to a transvenous lead that positions electrodes within a blood vessel but may remain outside the heart in an "extra-cardiac" location. For example, a transvenous medical lead may be advanced along a venous pathway to position electrodes within the internal thoracic vein (ITV), an intercostal vein, the superior epigastric vein, or the azygos, hemiazygos, or accessory hemiazygos veins, as examples. In still other examples, a transvenous lead may be advanced to position electrodes within the heart, such as the intracardiac electrodes generally shown in FIG. 3. Furthermore, a leadless medical device that is located within the heart, as generally shown in FIG. 4, or implanted outside the heart for sensing cardiac electrical signals using electrodes on the housing of the medical device may implement techniques disclosed herein.

More generally, the disclosed techniques may be used in any device that is configured to determine a rate or intervals of sensed cardiac events, which may include external heart rate monitors such as fitness trackers, watches, or other cardiac monitors that may use skin or surface electrodes for sensing cardiac electrical signals. The techniques disclosed herein are not dependent on the particular type of sensing electrodes used or their position, either internal or external. The medical devices shown in FIGS. 1A-4 are intended to show illustrative examples of devices that may be implemented in a system performing techniques disclosed herein with no limitation intended.

The cardiac events sensed by any of the devices described herein, e.g., in conjunction with FIGS. 1A-4 below, are primarily referred to as being cardiac electrical event signals, which may include P-waves attendant to atrial depolarization, R-waves attendant to ventricular depolarization or T-waves attendant to ventricular repolarization. However, it is to be understood that a cardiac medical device may sense other cardiac signals that are not necessarily electrical signals, such as mechanical cardiac signals. Examples of other types of cardiac signals that may be sensed by an implantable or external medical device include blood pressure signals, heart sounds, blood flow signals, impedance signals, heart acceleration signals, and oxygen saturation signals. The techniques disclosed herein for sensing a cardiac event using a sensing control parameter setting, storing a cardiac event feature and sensed event interval for each sensed cardiac event, and determining which of the sensed cardiac events would be sensed using a different sensing control parameter setting based on an analysis of the stored sensed event features and time intervals may be implemented in conjunction with a variety of cardiac signals, not necessarily limited to cardiac electrical signals.

The terms "cardiac event" and "cardiac event signal" as used herein therefore refer to any cardiac event that may be sensed during a single cardiac cycle or heartbeat and is not necessarily an electrical signal. For example, a systolic blood pressure, a diastolic blood pressure, an S1 heart sound, an S2 heart sound, a peak systolic flow, a peak oxygen saturation, and a peak ventricular acceleration, may all be examples of electrical or mechanical cardiac event signals that occur on a cyclical basis with each cardiac cycle. Cardiac events may be sensed for each cardiac cycle, e.g., beat-to-beat, over multiple cardiac cycles, to determine multiple sensed cardiac event intervals, which correspond to the heart rate. A cardiac rhythm, such as normal sinus rhythm, tachyarrhythmia, bradycardia or other rhythms may be determined from multiple cardiac event signals occurring at sensed event intervals that fall into a heart rate zone defining the particular rhythm. Depending on the sensed cardiac event interval between two consecutively sensed cardiac events, the event ending the sensed cardiac event interval may be classified as a normal sinus rhythm beat, a premature beat, a tachyarrhythmia beat, a bradycardia beat, a ventricular pause, etc. However, in order to detect an arrhythmia, such as atrial or ventricular tachycardia or fibrillation, a threshold number of sensed event intervals that fall within a tachycardia or fibrillation rate zone may be required before detection is made and a subsequent therapy is delivered. Accordingly, the sensing control parameter setting for sensing a single cardiac event signal refers to a setting used to sense a cardiac event that occurs within one cardiac cycle, such as any of the examples given above. Tachyarrhythmia detection parameters refer to parameters that are applied to detect the heart rhythm over multiple cardiac cycles, based on sensed cardiac events that are each sensed within one of the multiple cardiac cycles.

Figure 1B:
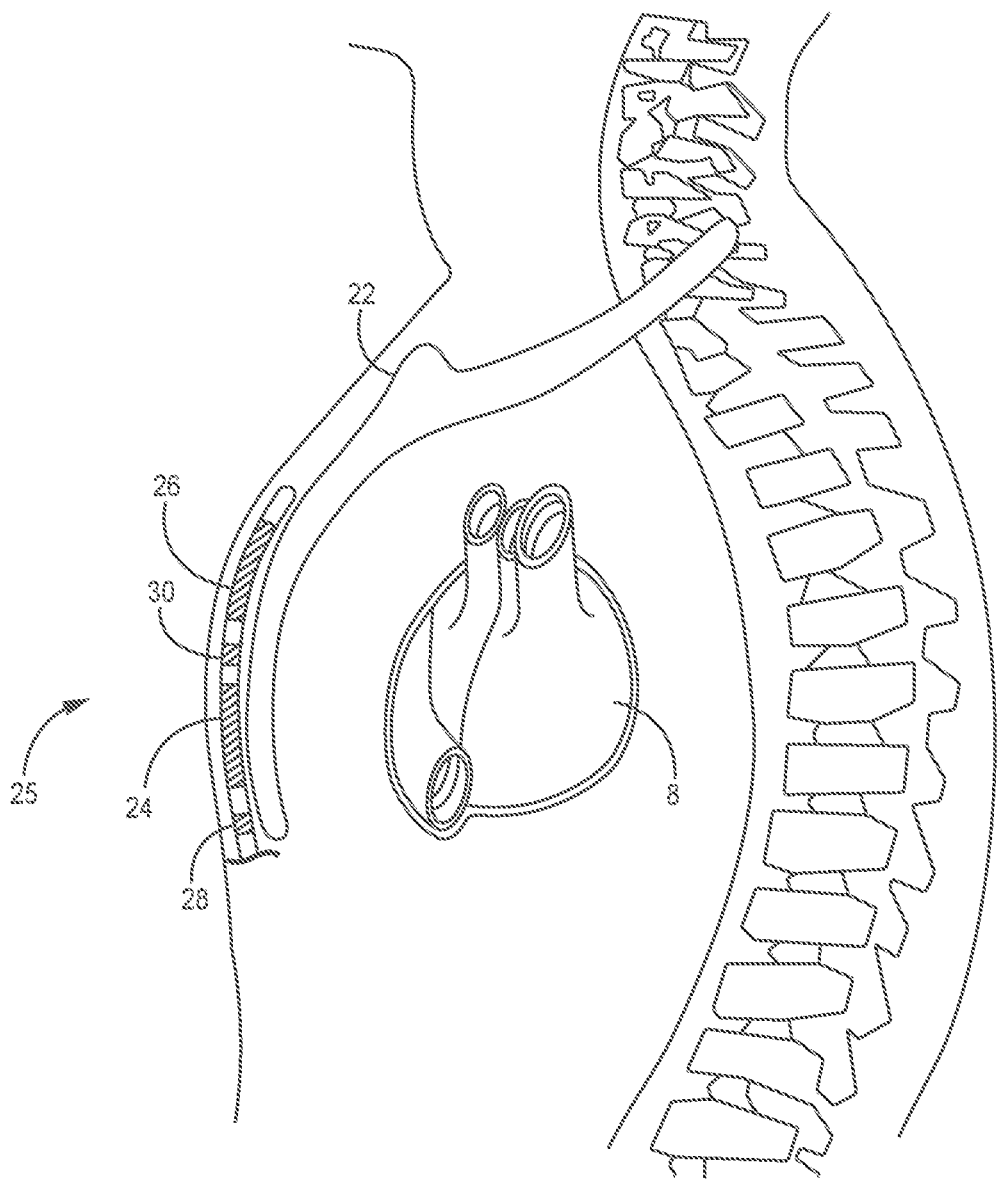

FIGS. 1A and 1B are conceptual diagrams of an ICD system 10 configured to sense cardiac electrical events and deliver cardiac electrical stimulation therapies according to one example. ICD system 10 is one example of a medical device configured sense cardiac electrical signals and perform the techniques disclosed herein. ICD system 10 includes an ICD 14 connected to an extra-cardiovascular electrical stimulation and sensing lead 16. FIG. 1A is a front view of ICD 14 implanted within patient 12. FIG. 1B is a side view of ICD 14 implanted within patient 12. FIGS. 1A and 1B are described in the context of an ICD system 10 capable of providing high voltage CV/DF shocks and in some examples cardiac pacing pulses.

ICD 14 includes a housing 15 that forms a hermetic seal that protects internal components of ICD 14. The housing 15 of ICD 14 may be formed of a conductive material, such as titanium or titanium alloy. The housing 15 may function as an electrode (sometimes referred to as a "can" electrode). Housing 15 may be used as an active can electrode for use in delivering CV/DF shocks or other high voltage pulses delivered using a high voltage therapy circuit. In other examples, housing 15 may be available for use in delivering unipolar, low voltage cardiac pacing pulses and/or for sensing cardiac electrical signals in combination with electrodes carried by lead 16. In other instances, the housing 15 of ICD 14 may include a plurality of electrodes on an outer portion of the housing. The outer portion(s) of the housing 15 functioning as an electrode(s) may be coated with a material, such as titanium nitride, e.g., for reducing post-stimulation polarization artifact.

ICD 14 includes a connector assembly 17 (also referred to as a connector block or header) that includes electrical feedthroughs crossing housing 15 to provide electrical connections between conductors extending within the lead body 18 of lead 16 and electronic components included within the housing 15 of ICD 14. As will be described in further detail herein, housing 15 may house one or more processors, memories, transceivers, cardiac electrical signal sensing circuitry, therapy delivery circuitry, power sources and other components for sensing cardiac electrical signals, detecting a heart rhythm, and controlling and delivering electrical stimulation pulses to treat an abnormal heart rhythm.

Lead 16 is shown in this example as an extra-cardiovascular lead implanted outside the ribcage and sternum. Lead 16 includes an elongated lead body 18 having a proximal end 27 that includes a lead connector (not shown) configured to be connected to ICD connector assembly 17 and a distal portion 25 that includes one or more electrodes. In the example illustrated in FIGS. 1A and 1B, the distal portion 25 of lead body 18 includes defibrillation electrodes 24 and 26 and pace/sense electrodes 28 and 30. In some cases, defibrillation electrodes 24 and 26 may together form a defibrillation electrode in that they may be configured to be activated concurrently. Alternatively, defibrillation electrodes 24 and 26 may form separate defibrillation electrodes in which case each of the electrodes 24 and 26 may be activated independently.

Electrodes 24 and 26 (and in some examples housing 15) are referred to herein as defibrillation electrodes because they may be utilized, individually or collectively, for delivering high voltage stimulation therapy (e.g., cardioversion or defibrillation shocks). Electrodes 24 and 26 may be elongated coil electrodes and generally have a relatively high surface area for delivering high voltage electrical stimulation pulses compared to pacing and sensing electrodes 28 and 30. However, electrodes 24 and 26 and housing 15 may also be utilized to provide pacing functionality, sensing functionality or both pacing and sensing functionality in addition to or instead of high voltage stimulation therapy. In this sense, the use of the term "defibrillation electrode" herein should not be considered as limiting the electrodes 24 and 26 for use in only high voltage cardioversion/defibrillation shock therapy applications. For example, either of electrodes 24 and 26 may be used as a sensing electrode in a sensing vector for sensing cardiac electrical signals and determining a need for an electrical stimulation therapy.

Electrodes 28 and 30 are relatively smaller surface area electrodes which are available for use in sensing electrode vectors for sensing cardiac electrical signals and may be used for delivering relatively low voltage pacing pulses in some configurations. Electrodes 28 and 30 are referred to as pace/sense electrodes because they are generally configured for use in low voltage applications, e.g., used as either a cathode or anode for delivery of pacing pulses and/or sensing of cardiac electrical signals, as opposed to delivering high voltage CV/DF shocks. In some instances, electrodes 28 and 30 may provide only pacing functionality, only sensing functionality or both.

ICD 14 may obtain cardiac electrical signals corresponding to electrical activity of heart 8 via a combination of sensing electrode vectors that include combinations of electrodes 24, 26, 28 and/or 30. In some examples, housing 15 of ICD 14 is used in combination with one or more of electrodes 24, 26, 28 and/or 30 in a sensing electrode vector. In the example illustrated in FIGS. 1A and 1B, electrode 28 is located proximal to defibrillation electrode 24, and electrode 30 is located between defibrillation electrodes 24 and 26. One, two or more pace/sense electrodes may be carried by lead body 18. For instance, a third pace/sense electrode may be located distal to defibrillation electrode 26 in some examples. Electrodes 28 and 30 are illustrated as ring electrodes; however, electrodes 28 and 30 may comprise any of a number of different types of electrodes, including ring electrodes, short coil electrodes, hemispherical electrodes, directional electrodes, segmented electrodes, or the like. Electrodes 28 and 30 may be positioned at other locations along lead body 18 and are not limited to the positions shown. In other examples, lead 16 may include fewer or more pace/sense electrodes and/or defibrillation electrodes than the example shown here.

In the example shown, lead 16 extends subcutaneously or submuscularly over the ribcage 32 medially from the connector assembly 27 of ICD 14 toward a center of the torso of patient 12, e.g., toward xiphoid process 20 of patient 12. At a location near xiphoid process 20, lead 16 bends or turns and extends superiorly, subcutaneously or submuscularly, over the ribcage and/or sternum, substantially parallel to sternum 22. Although illustrated in FIG. 1A as being offset laterally from and extending substantially parallel to sternum 22, the distal portion 25 of lead 16 may be implanted at other locations, such as over sternum 22, offset to the right or left of sternum 22, angled laterally from sternum 22 toward the left or the right, or the like. Alternatively, lead 16 may be placed along other subcutaneous or submuscular paths. The path of extra-cardiovascular lead 16 may depend on the location of ICD 14, the arrangement and position of electrodes carried by the lead body 18, and/or other factors. The techniques disclosed herein are not limited to a particular path of lead 16 or final locations of electrodes 24, 26, 28 and 30.

Electrical conductors (not illustrated) extend through one or more lumens of the elongated lead body 18 of lead 16 from the lead connector at the proximal lead end 27 to electrodes 24, 26, 28, and 30 located along the distal portion 25 of the lead body 18. The elongated electrical conductors contained within the lead body 18, which may be separate respective insulated conductors within the lead body 18, are each electrically coupled with respective defibrillation electrodes 24 and 26 and pace/sense electrodes 28 and 30. The respective conductors electrically couple the electrodes 24, 26, 28, and 30 to circuitry, such as a therapy delivery circuit and/or a sensing circuit, of ICD 14 via connections in the connector assembly 17, including associated electrical feedthroughs crossing housing 15. The electrical conductors transmit therapy from a therapy delivery circuit within ICD 14 to one or more of defibrillation electrodes 24 and 26 and/or pace/sense electrodes 28 and 30 and transmit sensed electrical signals produced by the patient's heart 8 from one or more of defibrillation electrodes 24 and 26 and/or pace/sense electrodes 28 and 30 to the sensing circuit within ICD 14.

The lead body 18 of lead 16 may be formed from a non-conductive material, including silicone, polyurethane, fluoropolymers, mixtures thereof, and/or other appropriate materials, and shaped to form one or more lumens within which the one or more conductors extend. Lead body 18 may be tubular or cylindrical in shape. In other examples, the distal portion 25 (or all of) the elongated lead body 18 may have a flat, ribbon or paddle shape. Lead body 18 may be formed having a preformed distal portion 25 that is generally straight, curving, bending, serpentine, undulating or zig-zagging.

In the example shown, lead body 18 includes a curving distal portion 25 having two "C" shaped curves, which together may resemble the Greek letter epsilon, "ε." Defibrillation electrodes 24 and 26 are each carried by one of the two respective C-shaped portions of the lead body distal portion 25. The two C-shaped curves are seen to extend or curve in the same direction away from a central axis of lead body 18, along which pace/sense electrodes 28 and 30 are positioned. Pace/sense electrodes 28 and 30 may, in some instances, be approximately aligned with the central axis of the straight, proximal portion of lead body 18 such that mid-points of defibrillation electrodes 24 and 26 are laterally offset from pace/sense electrodes 28 and 30.

Other examples of extra-cardiovascular leads including one or more defibrillation electrodes and one or more pacing and sensing electrodes carried by curving, serpentine, undulating or zig-zagging distal portion of the lead body 18 that may be implemented with the techniques described herein are generally disclosed in U.S. patent Ser. No. 10/675,478 (Marshall, et al.), incorporated herein by reference in its entirety. The techniques disclosed herein are not limited to any particular lead body design, however. In other examples, lead body 18 is a flexible elongated lead body without any pre-formed shape, bends or curves.

ICD 14 analyzes the cardiac electrical signals received from one or more sensing electrode vectors to monitor for abnormal rhythms, such as bradycardia, ventricular tachycardia (VT) or ventricular fibrillation (VF). ICD 14 may analyze the heart rate and morphology of the cardiac electrical signals to monitor for tachyarrhythmia in accordance with any of a number of tachyarrhythmia detection techniques. ICD 14 generates and delivers electrical stimulation therapy in response to detecting a tachyarrhythmia (e.g., VT or VF) using a therapy delivery electrode vector which may be selected from any of the available electrodes 24, 26, 28, 30 and/or housing 15. ICD 14 may deliver ATP in response to VT detection and in some cases may deliver ATP prior to a CV/DF shock or during high voltage capacitor charging in an attempt to avert the need for delivering a CV/DF shock. If ATP does not successfully terminate VT or when VF is detected, ICD 14 may deliver one or more CV/DF shocks via one or both of defibrillation electrodes 24 and 26 and/or housing 15. ICD 14 may deliver the CV/DF shocks using electrodes 24 and 26 individually or together as a cathode (or anode) and with the housing 15 as an anode (or cathode). ICD 14 may generate and deliver other types of electrical stimulation pulses such as post-shock pacing pulses, asystole pacing pulses, or bradycardia pacing pulses using a pacing electrode vector that includes one or more of the electrodes 24, 26, 28, and 30 and the housing 15 of ICD 14.

ICD 14 is shown implanted subcutaneously on the left side of patient 12 along the ribcage 32. ICD 14 may, in some instances, be implanted between the left posterior axillary line and the left anterior axillary line of patient 12. ICD 14 may, however, be implanted at other subcutaneous or submuscular locations in patient 12. For example, ICD 14 may be implanted in a subcutaneous pocket in the pectoral region. In this case, lead 16 may extend subcutaneously or submuscularly from ICD 14 toward the manubrium of sternum 22 and bend or turn and extend inferiorly from the manubrium to the desired location subcutaneously or submuscularly. In yet another example, ICD 14 may be placed abdominally. Lead 16 may be implanted in other extra-cardiovascular locations as well. For instance, as described with respect to FIGS. 2A-2C, the distal portion 25 of lead 16 may be implanted underneath the sternum/ribcage in the substernal space.

An external device 40 is shown in telemetric communication with ICD 14 by a communication link 42. External device 40 may include a processor 52, memory 53, display 54, user interface 56 and telemetry unit 58. Processor 52 controls external device operations and processes data and signals received from ICD 14. Display 54, which may include a graphical user interface (GUI), displays data and other information to a user for reviewing ICD operation and programmed parameters as well as cardiac electrical signals retrieved from ICD 14. As described below, processor 52 may receive sensed cardiac event data from ICD 14 for performing an analysis of the sensed cardiac event data based on different sensing control parameter settings. The analysis may generate a predicted sensed cardiac event rate and/or intervals that indicate how the ICD 14 may respond to sensed cardiac events when a different sensing control parameter setting is programmed in ICD 14 for sensing the cardiac event signals.

For example, processor 52 may determine predicted sensed cardiac event intervals for a different sensitivity setting than the programmed sensitivity setting used by ICD 14 for obtaining sensed cardiac event data. Based on the predicted sensed cardiac event intervals, processor 52 may determine a time interval until a predicted tachyarrhythmia detection by ICD 14 and generate a display of data related to the analysis on display unit 54. In one example, ICD 14 is configured to determine a maximum peak amplitude of multiple cardiac events that are sensed by the sensing circuitry included in ICD 14. The maximum peak amplitudes may be transmitted to external device 40 as sensed cardiac event data. Based on the maximum peak amplitudes and a different sensitivity setting than the sensitivity programmed in ICD 14, processor 52 may predict which cardiac events would be sensed with the different sensitivity setting and determine associated cardiac event intervals.

Processor 52 executes instructions stored in memory 53. Processor 52 may include any one or more of a microprocessor, a controller, a digital signal processor (DSP), an application specific integrated circuit (ASIC), a field-programmable gate array (FPGA), or equivalent discrete or analog logic circuitry. In some examples, processor 52 may include multiple components, such as any combination of one or more microprocessors, one or more controllers, one or more DSPs, one or more ASICs, or one or more FPGAs, as well as other discrete or integrated logic circuitry. The functions attributed to processor 52 herein may be embodied as software, firmware, hardware or any combination thereof.

Memory 53 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital or analog media. Memory 53 may be configured to store sensing control parameters and associated programmable settings. Memory 53 may store predicted sensed cardiac event data determined by processor 52 for use in generating an output representative of the predicted sensed cardiac events as disclosed herein.

User interface 56 may include a mouse, touch screen, key pad or the like to enable a user to interact with external device 40 to initiate a telemetry session with ICD 14 for retrieving data from and/or transmitting data to ICD 14, including programmable parameters for controlling cardiac event sensing and therapy delivery. A clinician may use user interface 56 to send and receive commands to ICD 14 via external device 40. As described herein, a clinician may use user interface 56 to specify one or more sensing control parameters. Typically, user interface 56 includes one or more input devices and one or more output devices, including display unit 54. The input devices of user interface 56 may include a communication device such as a network interface, keyboard, pointing device, voice responsive system, video camera, biometric detection/response system, button, sensor, mobile device, control pad, microphone, presence-sensitive screen, touch-sensitive screen (which may be included in display unit 54), network, or any other type of device for detecting input from a human or machine.

The one or more output devices of user interface 56 may include a communication unit such as a network interface, display, sound card, video graphics adapter card, speaker, presence-sensitive screen, one or more USB interfaces, video and/or audio output interfaces, or any other type of device capable of generating tactile, audio, video, or other output. Display unit 54 may function as an input and/or output device using technologies including liquid crystal displays (LCD), quantum dot display, dot matrix displays, light emitting diode (LED) displays, organic light-emitting diode (OLED) displays, cathode ray tube (CRT) displays, e-ink, or monochrome, color, or any other type of display capable of generating tactile, audio, and/or visual output. In other examples, user interface 56 may produce an output to a user in another fashion, such as via a sound card, video graphics adapter card, speaker, presence-sensitive screen, touch-sensitive screen, one or more USB interfaces, video and/or audio output interfaces, or any other type of device capable of generating tactile, audio, video, or other output. In some examples, display unit 54 is a presence-sensitive display that may serve as a user interface device that operates both as one or more input devices and one or more output devices.

Telemetry unit 58 includes a transceiver and antenna configured for bidirectional communication with a telemetry circuit included in ICD 14 and is configured to operate in conjunction with processor 52 for sending and receiving data relating to ICD functions via communication link 42. Communication link 42 may be established between ICD 14 and external device 40 using a radio frequency (RF) link such as BLUETOOTH®, Wi-Fi, or Medical Implant Communication Service (MICS) or other RF or communication frequency bandwidth or communication protocols. Data stored or acquired by ICD 14, including cardiac signals or associated data derived therefrom, results of device diagnostics, and histories of detected rhythm episodes and delivered therapies, may be retrieved from ICD 14 by external device 40 following an interrogation command.

In particular, external device 40 may retrieve sensed cardiac event data determined by ICD 14. For example, as described below, external device 40 may retrieve maximum peak amplitude data from ICD 14. The maximum peak amplitude of each cardiac event sensed by ICD 14 may be determined, e.g., during a detected tachyarrhythmia episode. The maximum peak amplitudes may be used by processor 52 in an analysis to determine predicted sensed cardiac event intervals based on a different sensitivity setting applied to the retrieved maximum peak amplitudes. In this way, a prediction of whether a tachyarrhythmia would be detected using a different sensitivity setting and the predicted time required to detect the tachyarrhythmia may be determined by processor 52 and displayed on a GUI by display unit 54.

External device 40 may be embodied as a programmer used in a hospital, clinic or physician's office to retrieve data from ICD 14 and to program operating parameters and algorithms in ICD 14 for controlling ICD functions. External device 40 may alternatively be embodied as a home monitor or handheld device. External device 40 may be used to program cardiac signal sensing control parameters, cardiac rhythm detection parameters and therapy control parameters used by ICD 14. While external device 40 is shown only in FIG. 1A, it is to be understood that all or portions of the techniques disclosed herein may be performed by an external device, such as device 40, configured to communicate with an implantable or external medical device configured to sense cardiac electrical signals, including but not limited to any of the ICDs or pacemakers shown in FIGS. 1A-4. Aspects of external device 40 may generally correspond to the external programming/monitoring unit disclosed in U.S. Pat. No. 5,507,782 (Kieval, et al.), hereby incorporated herein by reference in its entirety. An example programmer that may be configured to perform the techniques disclosed herein is the CARELINK® Programmer, commercially available from Medtronic, Inc., Minneapolis, Minnesota, USA.

In some examples, external device 40 includes external ports 55 adapted for electrical connection to a cardiac lead carrying electrodes, such as lead 16 so that processor 52 may receive a cardiac electrical signal directly for determining sensed cardiac event data according to one sensitivity setting and analyze the sensed cardiac event data according to one or more alternative sensitivity settings according to the techniques disclosed herein.

Figure 2A:
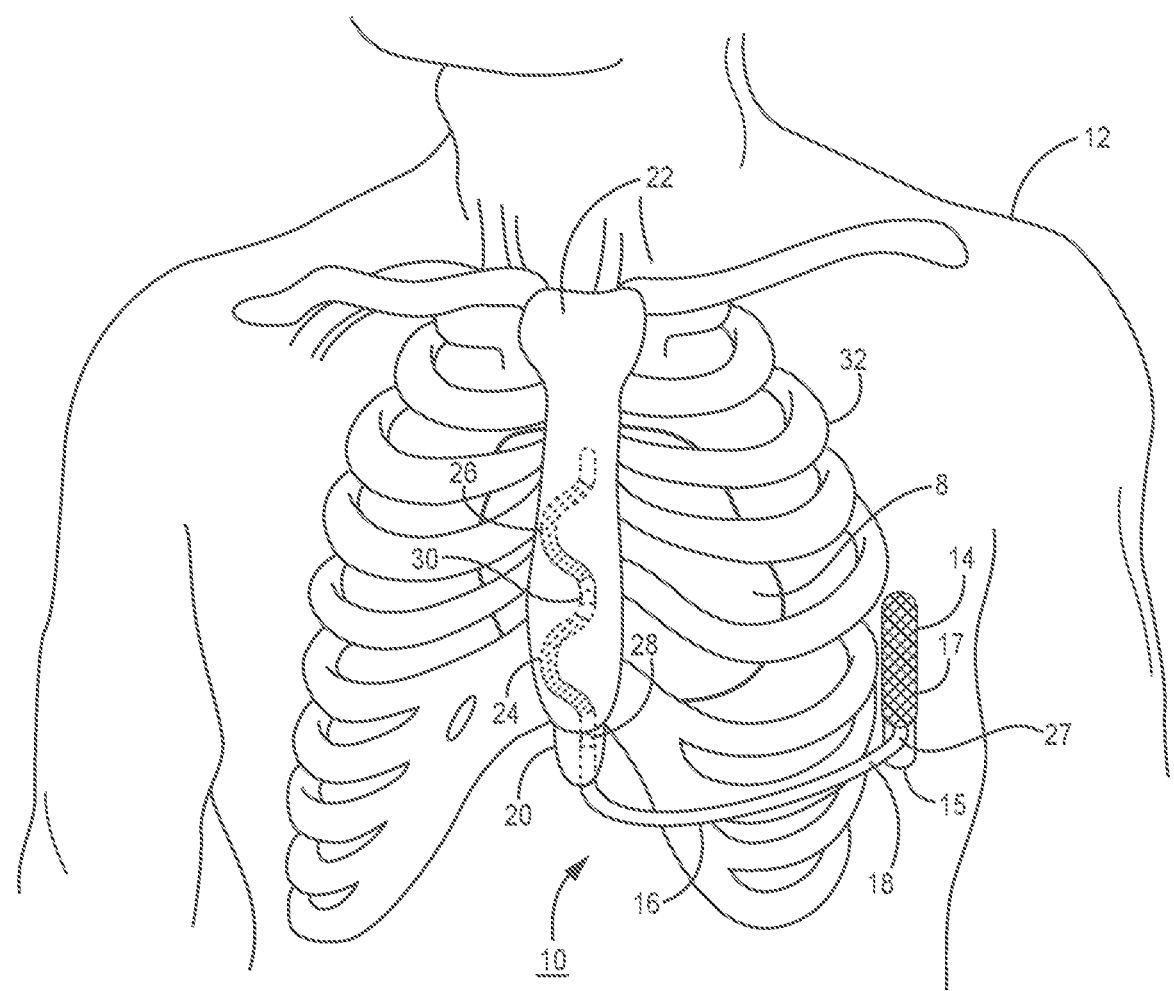
FIGS. 2A-2C are conceptual diagrams of a patient implanted with the ICD system shown in FIGS. 1A-1B in a different implant configuration.
Figure 2B:
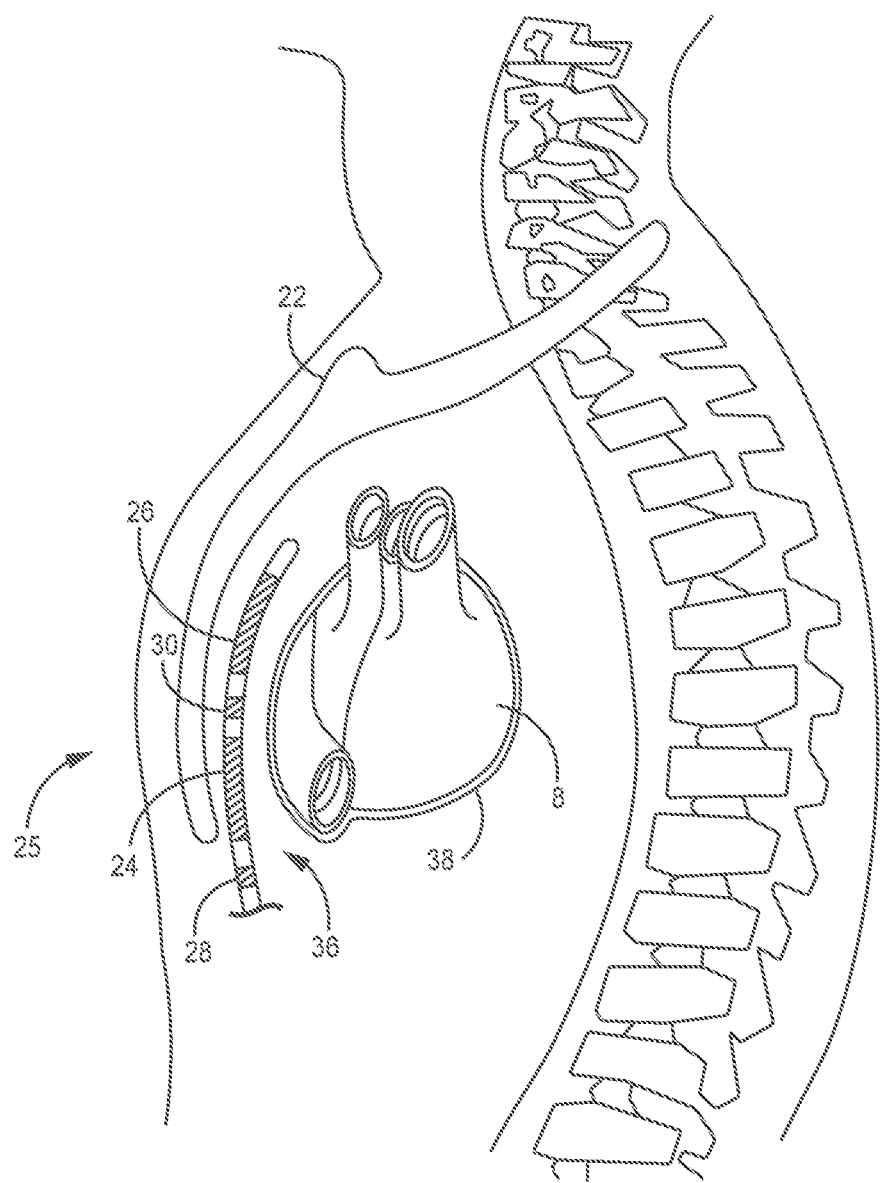
Figure 2C:
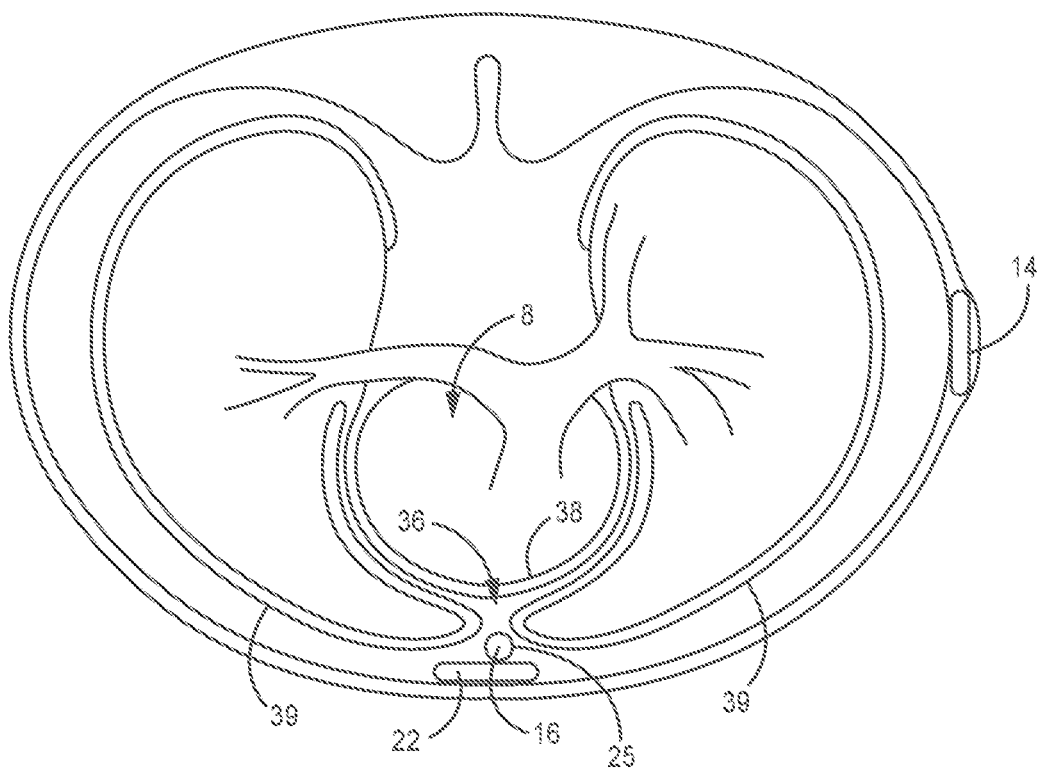

FIGS. 2A-2C are conceptual diagrams of patient 12 implanted with ICD system 10 in a different implant configuration than the arrangement shown in FIGS. 1A-1B. FIG. 2A is a front view of patient 12 implanted with ICD system 10. FIG. 2B is a side view of patient 12 implanted with ICD system 10. FIG. 2C is a transverse view of patient 12 implanted with ICD system 10. In this arrangement, lead 16 of system 10 is implanted at least partially underneath sternum 22 of patient 12. Lead 16 extends subcutaneously or submuscularly from ICD 14 toward xiphoid process 20 and at a location near xiphoid process 20 bends or turns and extends superiorly within anterior mediastinum 36 in a substernal position.

Anterior mediastinum 36 may be viewed as being bounded laterally by pleurae 39, posteriorly by pericardium 38, and anteriorly by sternum 22 (see FIG. 2C). The distal portion 25 of lead 16 may extend along the posterior side of sternum 22 substantially within the loose connective tissue and/or substernal musculature of anterior mediastinum 36. A lead implanted such that the distal portion 25 is substantially within anterior mediastinum 36, or within a pleural cavity or more generally within the thoracic cavity, may be referred to as a "substernal lead."

In the example illustrated in FIGS. 2A-2C, lead 16 is located substantially centered under sternum 22. In other instances, however, lead 16 may be implanted such that it is offset laterally from the center of sternum 22. In some instances, lead 16 may extend laterally such that distal portion 25 of lead 16 is underneath/below the ribcage 32 in addition to or instead of sternum 22. In other examples, the distal portion 25 of lead 16 may be implanted in other extra-cardiovascular, intra-thoracic locations, including the pleural cavity or around the perimeter of and adjacent or within the pericardium 38 of heart 8.

Figure 3:
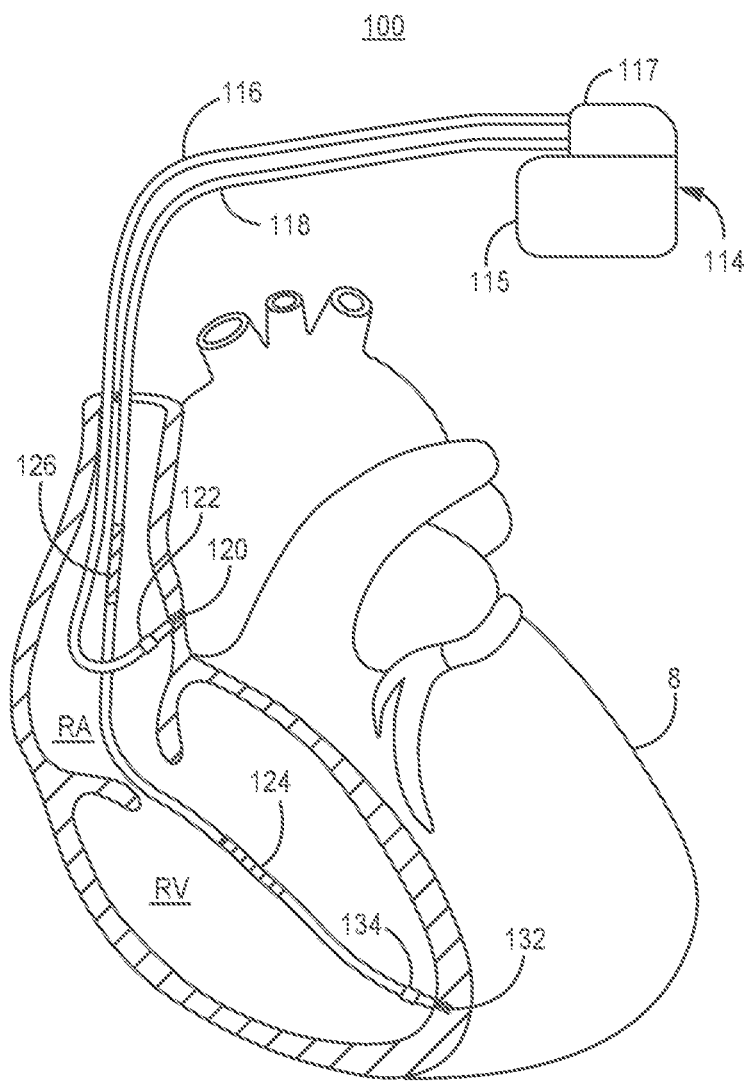
FIG. 3 is a conceptual diagram of an ICD system including transvenous medical electrical leads according to one example.
Figure 4:
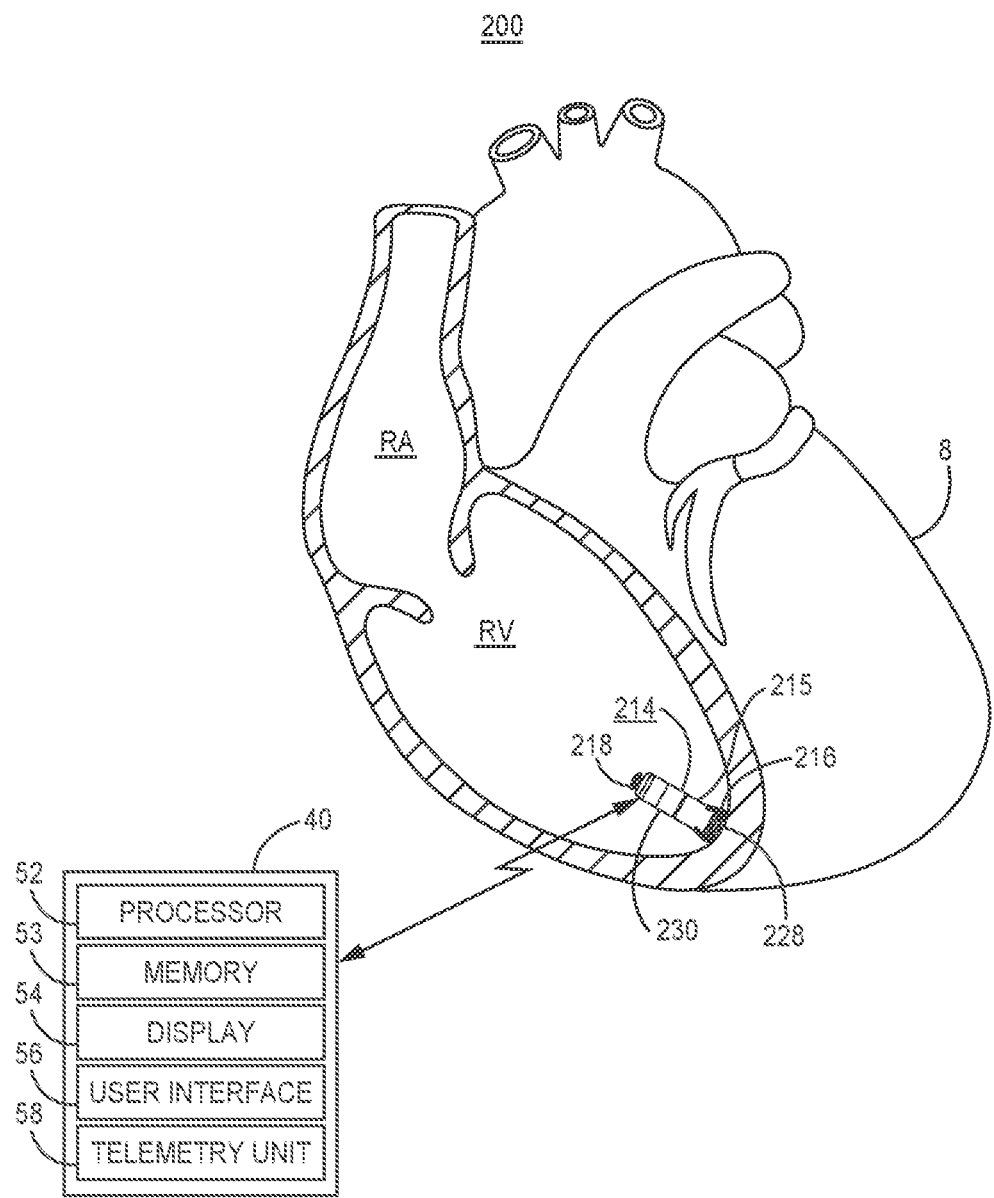
FIG. 4 is a conceptual diagram of an intracardiac medical device according to one example.

FIG. 3 is a conceptual diagram of an ICD system 100 according to another example. ICD system 100 includes ICD 114 coupled to transvenous leads 116 and 118 in communication with the right atrium (RA) and right ventricle (RV), respectively, of heart 8. ICD 114 includes a housing 115 enclosing circuitry, such as a processor, telemetry circuitry, sensing circuitry and therapy delivery circuitry, e.g., as generally described below in conjunction with FIG. 5. ICD 114 includes connector assembly 117 having connector bores for receiving proximal connectors of RA lead 116 and RV lead 118. RA lead 116 may carry a distal tip electrode 120 and ring electrode 122 for sensing atrial electrical signals and producing an atrial intra-cardiac electrogram (EGM) signal. RA electrodes 120 and 122 may be used for delivering RA pacing pulses. RV lead 118 may carry pacing and sensing electrodes 132 and 134 for sensing a ventricular electrical signal and producing an RV EGM signal. RV electrodes 132 and 134 may be used to deliver RV pacing pulses. RV lead 118 may also carry an RV defibrillation electrode 124 and a superior vena cava (SVC) defibrillation electrode 126. Defibrillation electrodes 124 and 126 are shown as coil electrodes spaced apart proximally from the distal pacing and sensing electrodes 132 and 134.

ICD 114 may be configured to provide dual chamber sensing and pacing therapies as well as high voltage CV/DF shock therapies in response to detecting VT or VF. In other examples, ICD 114 may be configured to provide multi-chamber sensing and pacing therapies, including CRT, in which case a coronary sinus lead may be advanced along a cardiac vein to position electrodes for sensing and pacing the left ventricle of heart 8.

FIG. 4 is a conceptual diagram of an intracardiac pacemaker 214 configured to sense cardiac signals and deliver a pacing therapy according to another example. Pacemaker 214 may be a transcatheter pacemaker which is adapted for implantation wholly within a heart chamber, e.g., wholly within the right ventricle (RV) or wholly within the left ventricle (LV) of heart 8 for sensing cardiac signals and delivering ventricular pacing pulses. Pacemaker 214 may alternatively be implantable wholly with an atrial chamber for sensing cardiac signals and delivering atrial pacing pulses. Pacemaker 214 may be reduced in size compared to subcutaneously implanted pacemakers and may be generally cylindrical in shape to enable transvenous implantation via a delivery catheter. Pacemaker 214 may include a delivery tool interface 218 for engaging with a delivery tool, such as a catheter delivery system, for advancing pacemaker 214 along a transvenous pathway and into heart 8. Pacemaker 214 may include a fixation member 216 for anchoring pacemaker 214 at an implant site within or on heart 8. Pacemaker 214 is shown positioned in the RV, along an endocardial wall, e.g., near the RV apex though other locations are possible. The techniques disclosed herein are not limited to the pacemaker location shown in the example of FIG. 4 and other positions within or on heart 8 are possible.

Pacemaker 214 may be capable of producing electrical stimulation pulses, e.g., pacing pulses, delivered to heart 8 via one or more electrodes 228 and 230 on the outer housing 215 of the pacemaker. For example, pacemaker 214 may be configured to deliver RV pacing pulses and sense an RV cardiac electrical signal using housing based electrodes 228 and 230 for producing an RV electrogram (EGM) signal. The cardiac electrical signals may be sensed using the housing based electrodes that are also used to deliver pacing pulses to the RV in some examples.

Pacemaker 214 may include a telemetry circuit for communicating with another medical device, e.g., external device 40, described above in conjunction with FIG. 1A. In some examples, pacemaker 214 may be configured to communicate with another medical device implanted within the patient. For example, pacemaker 214 may be co-implanted in a patient implanted with ICD 14 shown in FIGS. 1A-2C and may be configured to communicate with ICD 14 via wireless communication. ICD 14 may, in turn, be configured to communicate with external device 40 and may serve as a relay device for communication between pacemaker 214 and external device 40.

Pacemaker 214 may sense cardiac electrical events, e.g., P-waves and/or R-waves, and determine a feature of each sensed event. In some examples, the feature is the maximum peak amplitude of the sensed event. Pacemaker 214 may store the maximum peak amplitudes and the sensed event intervals as cardiac event data for transmission to another medical device for analysis based on a different sensing control parameter, as described below. External device 40 may generate a display on display unit 54 indicating which events sensed by pacemaker 214 would still be sensed using a different sensing control parameter setting, e.g., a different sensitivity.

In response to a sensed cardiac event signal, pacemaker 214 may be configured to inhibit or trigger a cardiac pacing pulse according to a pacing therapy protocol. Pacemaker 214 may schedule a pacing pulse by starting a pacing interval in response to a sensed cardiac event and generate the pacing pulse in response to the pacing interval expiring before the next cardiac event signal is sensed. Pacemaker 214 may be configured to deliver pacing therapy to provide bradycardia pacing, atrial synchronized ventricular pacing, rate response pacing, asystole pacing or other pacing therapies. In some examples, pacemaker 214 may detect a tachyarrhythmia based on sensed cardiac event intervals and deliver ATP therapy in response to detecting the tachyarrhythmia. Pacemaker 214 is described as having pacing capabilities, however, in some examples, the medical device performing techniques disclosed herein may be a monitoring only device that senses cardiac event signals and determines a feature and interval associated with each sensed cardiac event for analysis using a different sensing control parameter setting.

Figure 5:
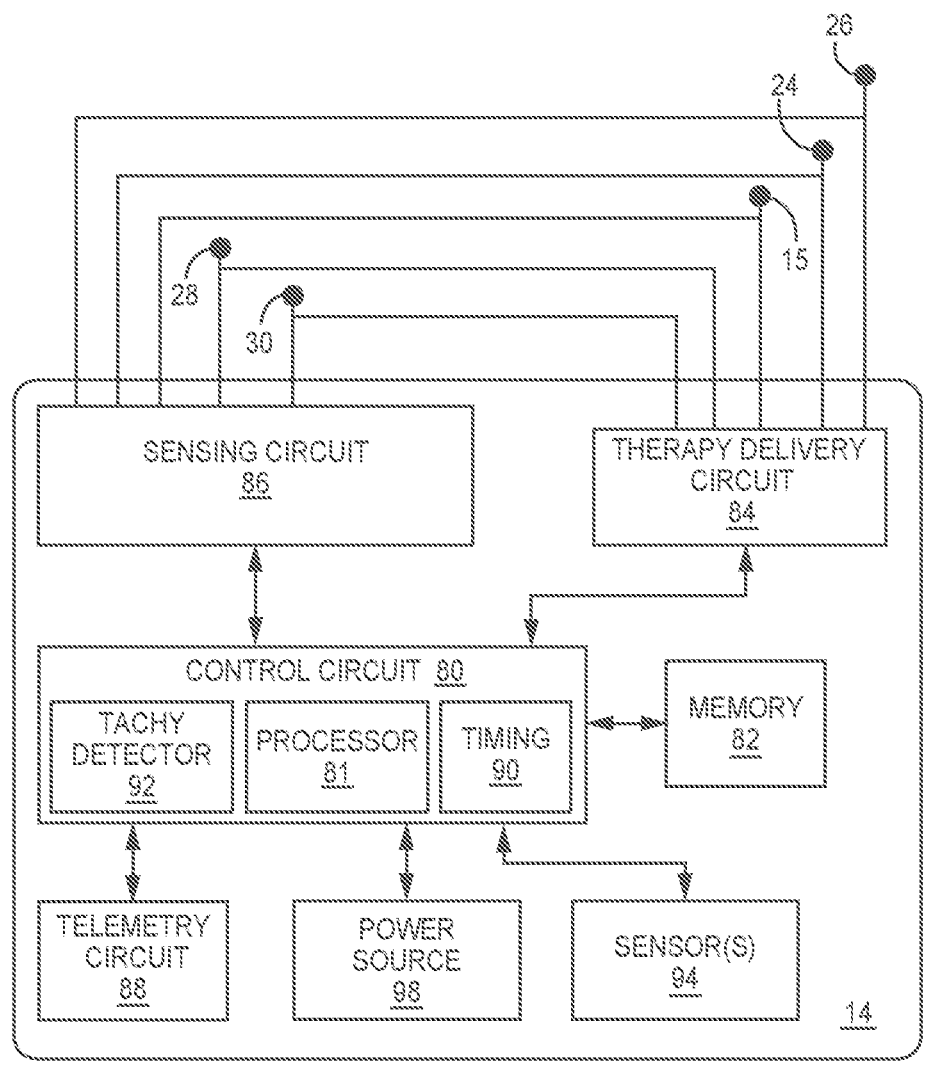
FIG. 5 is a conceptual diagram of a medical device configuration for sensing cardiac signals and determining sensed cardiac event data according to one example.

FIG. 5 is a conceptual diagram of a medical device configuration for sensing cardiac signals and determining sensed cardiac event data according to one example. FIG. is described in conjunction with the ICD 14 of FIGS. 1A-2C for the sake of convenience. It is to be understood, however, that the circuitry and functionality attributed to the circuitry and components described in conjunction with FIG. 5 may be included, in whole or in part, in any of the example implantable medical devices described or listed herein, such as the ICD 114 shown in FIG. 3 or pacemaker 214 shown in FIG. 4. The ICD housing is shown schematically as an electrode in FIG. 5 since the housing of the medical device may be used an electrode for cardiac signal sensing and/or therapy delivery in some examples. The electronic circuitry enclosed within housing 15 includes software, firmware and hardware that cooperatively monitor cardiac signals, determine when an electrical stimulation therapy is necessary, and deliver therapy as needed according to programmed therapy delivery algorithms and control parameters, which may be stored in memory 82. ICD 14 may be coupled to an extra-cardiovascular lead, such as lead 16 shown in FIG. 1A, carrying extra-cardiovascular electrodes 24, 26, 28, and 30, for delivering electrical stimulation pulses to the patient's heart and for sensing cardiac electrical signals. It is understood, however, that electrodes 24, 26, 28 and 30 shown in FIG. 5 may be carried by a transvenous lead advanced within an artery or vein to an extra-cardiac or intracardiac location. Furthermore, electrodes coupled to the medical device may be housing based electrodes, on the housing of the medical device as shown in FIG. 4.

ICD 14 as shown in FIG. 5 includes a control circuit 80, memory 82, therapy delivery circuit 84, cardiac electrical signal sensing circuit 86, and telemetry circuit 88. In some examples, ICD 14 may include other sensors 94 for sensing a cardiac signal corresponding to any of the example cardiac signals given above, such as a pressure sensor, flow sensor, impedance sensing circuitry, accelerometer or other motion sensor, optical sensor, acoustical sensor or the like. While sensor(s) 94 are conceptually shown enclosed by housing 15 in FIG. 5, it is recognized that one or more sensors 94 may be enclosed by the medical device housing 15 and/or one or more sensors 94 may be carried outside the housing, e.g., on an exterior portion of the housing 15 and/or carried by a lead extending away from housing 15.

A power source 98 provides power to the circuitry of ICD 14, including each of the components 80, 82, 84, 86, 88, and 94 as needed. Power source 98 may include one or more energy storage devices, such as one or more rechargeable or non-rechargeable batteries. The connections between power source 98 and each of the other components 80, 82, 84, 86 and 88 are to be understood from the general block diagram of FIG. 5 but are not shown for the sake of clarity. For example, power source 98 may be coupled to one or more charging circuits included in therapy delivery circuit 84 for charging holding capacitors or other charge storage devices included in therapy delivery circuit 84 that are discharged at appropriate times under the control of control circuit 80 for producing electrical pulses according to a therapy protocol. In other examples, power source 98 may serve as a voltage or current source to therapy delivery circuit 84 without requiring a charge storage device. Power source 98 is also coupled to components of cardiac electrical signal sensing circuit 86, such as sense amplifiers, analog-to-digital converters, switching circuitry, etc. as needed.

The circuits shown in FIG. 5 represent functionality included in ICD 14 or another medical device operating according to the techniques disclosed herein and may include any discrete and/or integrated electronic circuit components that implement analog and/or digital circuits capable of producing the functions attributed to ICD 14 herein. Functionality associated with one or more circuits may be performed by separate hardware, firmware or software components, or integrated within common hardware, firmware or software components. For example, cardiac event sensing and determination of sensed cardiac event features and sensed event intervals may be performed cooperatively by sensing circuit 86 and control circuit 80 and may include operations implemented in a processor or other signal processing circuitry included in control circuit executing instructions stored in memory 82. Control signals such as blanking and timing intervals and sensing threshold amplitude signals may be sent from control circuit to sensing circuit 86 according to programmed sensing control parameter settings.

The various circuits of ICD 14 may include an application specific integrated circuit (ASIC), an electronic circuit, a processor (shared, dedicated, or group) and memory that execute one or more software or firmware programs, a combinational logic circuit, state machine, or other suitable components or combinations of components that provide the described functionality. The particular form of software, hardware and/or firmware employed to implement the functionality disclosed herein will be determined primarily by the particular system architecture employed in the implantable medical device and by the particular detection and therapy delivery methodologies employed by the implantable medical device. Providing software, hardware, and/or firmware to accomplish the described functionality in the context of any modern medical device, given the disclosure herein, is within the abilities of one of skill in the art.

Memory 82 may include any volatile, non-volatile, magnetic, or electrical non-transitory computer readable storage media, such as random access memory (RAM), read-only memory (ROM), non-volatile RAM (NVRAM), electrically-erasable programmable ROM (EEPROM), flash memory, or any other memory device. Furthermore, memory 82 may include non-transitory computer readable media storing instructions that, when executed by one or more processing circuits, cause control circuit 80 and/or other ICD components to perform various functions attributed to ICD 14 or those ICD components. The non-transitory computer-readable media storing the instructions may include any of the media listed above.

Control circuit 80 communicates, e.g., via a data bus, with therapy delivery circuit 84 and sensing circuit 86 and optionally sensors 94 for sensing cardiac event signals, detecting cardiac rhythms, and controlling delivery of cardiac electrical stimulation therapies in response to sensed cardiac event signals. Processor 81 may include one or more digital signal processors (DSPs), general purpose microprocessors, application specific integrated circuits (ASICs), field programmable logic arrays (FPLAs), or other equivalent integrated or discrete logic circuitry for executing instructions which may be stored in memory 82 to perform functionality attributed to pacemaker 14 herein.

Therapy delivery circuit 84 and sensing circuit 86 are electrically coupled to electrodes 24, 26, 28, 30, e.g., by lead 16, and the housing 15, which may function as a common or ground electrode or as an active can electrode for delivering CV/DF shock pulses or cardiac pacing pulses. Cardiac electrical signal sensing circuit 86 (also referred to herein as "sensing circuit" 86) may be selectively coupled to electrodes 28, 30 and/or housing 15 in order to monitor electrical activity of the patient's heart. Sensing circuit 86 may additionally or alternatively be selectively coupled to defibrillation electrodes 24 and/or 26 for use in a sensing electrode vector together or in combination with one or more of electrodes 28, 30 and/or housing 15. Sensing circuit 86 may be enabled to selectively receive cardiac electrical signals from one or more sensing electrode vectors from the available electrodes 24, 26, 28, 30, and housing 15 in some examples. Sensing circuit 86 may monitor one or more cardiac electrical signals for sensing cardiac electrical events and/or producing digitized cardiac signal waveforms for analysis by control circuit 80. For example, sensing circuit 86 may include switching circuitry for selecting which of electrodes 24, 26, 28, 30, and housing 15 are coupled to one or more sensing channels of sensing circuit 86.

As described below in conjunction with FIG. 6, sensing circuit 86 may be configured to amplify, filter, rectify and digitize or otherwise process the cardiac electrical signal received from selected sensing electrodes to improve the signal quality for sensing cardiac electrical event signals, such as R-waves or P-waves. Cardiac event detection circuitry included within sensing circuit 86 may include one or more sense amplifiers, filters, rectifiers, threshold detectors, comparators, analog-to-digital converters (ADCs), timers or other analog or digital components configured to sense cardiac electrical events.

Sensing circuit 86 may control an auto-adjusting cardiac event sensing threshold over each cardiac cycle. Sensing circuit 86 may sense a cardiac electrical event in response to a sensing threshold crossing by the cardiac electrical signal and produce a cardiac sensed event signal, e.g., an atrial sensed event signal in response to a P-wave sensing threshold crossing or a ventricular sensed event signal in response to an R-wave sensing threshold crossing. The cardiac sensed event signals are passed to control circuit 80. The cardiac event sensing threshold may be set to a starting threshold based on the maximum peak amplitude of a sensed cardiac event. The cardiac event sensing threshold may decay or decrease from the starting amplitude over the cardiac cycle according to one or more decay rates and/or one or more step drops until the next cardiac event is sensed in response to a sensing threshold crossing. The cardiac event sensing threshold amplitude may be decreased to a minimum threshold equal to a programmed sensitivity for sensing the cardiac event. The programmed sensitivity setting is sometimes referred to as the "sensing floor" because it is the lowest sensing threshold that may be reached during a cardiac cycle. The sensing floor may or may not be reached during a given cardiac cycle depending on how early the next cardiac event signal occurs following the most recently sensed cardiac event signal.

The sensing threshold amplitude may be decreased from a starting threshold amplitude toward the programmed sensitivity according to one or more decay intervals and corresponding decay rates and/or one or more drop time intervals and corresponding step drops. These sensing threshold control parameters may be stored in memory 82 and passed to sensing circuit 86 from control circuit 80 for use by hardware, firmware and/or software of control circuit 80 and/or sensing circuit 86 in controlling the sensing threshold amplitude.

Control circuit 80 receives the cardiac sensed event signals from sensing circuit 86 for determining sensed event intervals, e.g., RR intervals (RRIs) and/or PP intervals (PPIs), by timing circuit 90. An RRI is the time interval between two consecutively sensed R-waves and may be determined between consecutive ventricular sensed event signals received by control circuit 80 from sensing circuit 86. A PPI is the time interval between two consecutively sensed P-waves and may be determined between consecutive atrial sensed event signals received by control circuit 80 from sensing circuit 86. Timing circuit 90 may start an escape interval timer in response to a sensed event signal and restart the escape interval timer in response to the next sensed event signal. The value of the escape interval timer at the time of the next sensed event signal may be buffered in memory 82 as the sensed event interval for the associated sensed event signal. In this way, memory 82 may store a series of sensed event intervals. Each sensed event interval may be stored in conjunction with one or more sensed cardiac event features determined from the sensed cardiac event signal, such as the maximum peak amplitude of the sensed cardiac event signal. As described below in conjunction with FIG. 8, the maximum peak amplitude of a sensed cardiac event may be used to set the starting sensing threshold amplitude for the next cardiac cycle.

The sensed event signals, e.g., ventricular sensed event signals and/or atrial sensed event signals, may be used by control circuit 80 for detecting tachyarrhythmia and determining a need for therapy. For example, timing circuit 90 may include various timers and/or counters used to control the timing of therapy delivery by therapy delivery circuit 84. In response to expiration of an escape interval timer without receiving a cardiac sensed event signal, control circuit 80 may control therapy delivery circuit 84 to generate and deliver a pacing pulse. Timing circuit 90 may additionally set time windows such as morphology template windows, morphology analysis windows or perform other timing related functions of ICD 14 including synchronizing cardioversion shocks or other therapies delivered by therapy delivery circuit 84 with sensed cardiac events.

Control circuit 80 may include a tachyarrhythmia detector 92 configured to analyze signals received from sensing circuit 86 for detecting tachyarrhythmia. Tachyarrhythmia detector 92 may detect tachyarrhythmia based on cardiac events sensed by sensing circuit 86 meeting tachyarrhythmia detection criteria, such as a threshold number of sensed cardiac events occurring sensed event intervals falling in a tachyarrhythmia interval range. Tachyarrhythmia detector 92 may be implemented in control circuit 80 as hardware, software and/or firmware that processes and analyzes signals received from sensing circuit 86 for detecting tachyarrhythmia, e.g., supraventricular tachycardia (SVT), VT and/or VF. Tachyarrhythmia detector 92 may include comparators and counters for counting cardiac event intervals, e.g., PPIs or RRIs determined by timing circuit 90, that fall into various rate detection zones for determining an atrial rate and/or a ventricular rate or performing other rate- or interval-based assessment of cardiac sensed event signals for detecting and discriminating tachyarrhythmias.

For example, tachyarrhythmia detector 92 may compare the RRIs determined by timing circuit 90 to one or more tachyarrhythmia detection interval zones, such as a tachycardia detection interval zone and a fibrillation detection interval zone. RRIs falling into a detection interval zone are counted by a respective VT interval counter or VF interval counter and in some cases in a combined VT/VF interval counter included in tachyarrhythmia detector 92. The VF detection interval threshold may be set to 300 to 350 milliseconds (ms), as examples. For instance, if the VF detection interval is set to 320 ms, RRIs that are less than 320 ms are counted by the VF interval counter. When VT detection is enabled, the VT detection interval may be programmed to be in the range of 350 to 420 ms, or 400 ms as an example. RRIs that are less than the VT detection interval but greater than the VF detection interval may be counted by a VT interval counter. In order to detect VT or VF, the respective VT or VF interval counter is required to reach a threshold "number of intervals to detect" (NID).

As an example, the NID to detect VT may require that the VT interval counter reaches 18 VT intervals, 24 VT intervals, 32 VT intervals or other selected NID. In some examples, the VT intervals may be required to be consecutive intervals, e.g., 18 out of 18, 24 out of 24, or 32 out of the most recent 32 consecutive RRIs. The NID required to detect VF may be programmed to a threshold number X VF intervals out of Y consecutive RRIs. For instance, the NID required to detect VF may be 18 VF intervals out of the most recent 24 consecutive RRIs or 30 VF intervals out 40 consecutive RRIs, as examples. When a VT or VF interval counter reaches an NID threshold, a ventricular tachyarrhythmia may be detected by tachyarrhythmia detector 92. The NID may be programmable and range from as low as 12 to as high as 40, with no limitation intended. VT or VF intervals may be detected consecutively or non-consecutively out of the specified number of most recent RRIs. In some cases, a combined VT/VF interval counter may count both VT and VF intervals and detect a tachyarrhythmia episode based on the fastest intervals detected when a specified NID is reached.

Tachyarrhythmia detector 92 may be configured to perform other signal analysis for determining if other detection criteria are satisfied before detecting VT or VF, such as R-wave morphology criteria and onset criteria. To support additional cardiac signal analyses, sensing circuit 86 may pass a digitized electrocardiogram (ECG) signal (or EGM signal when sensed using intracardiac electrodes) to control circuit 80 for morphology analysis performed by tachyarrhythmia detector 92 for detecting and discriminating heart rhythms. A cardiac electrical signal from the selected sensing vector may be passed through a filter and amplifier, provided to a multiplexer and thereafter converted to a multi-bit digital signal by an analog-to-digital converter, all included in sensing circuit 86, for storage in memory 82. Memory 82 may include one or more circulating buffers to temporarily store digital cardiac electrical signal segments for analysis performed by control circuit 80. Control circuit 80 may be a microprocessor-based controller including processor 81 that employs digital signal analysis techniques to characterize the digitized signals stored in memory 82 to recognize and classify the patient's heart rhythm employing any of numerous signal processing methodologies for analyzing cardiac signals and cardiac event waveforms, e.g., R-waves.

Therapy delivery circuit 84 includes charging circuitry, one or more charge storage devices such as one or more high voltage capacitors and/or low voltage capacitors, and switching circuitry that controls when the capacitor(s) are discharged across a selected pacing electrode vector or CV/DF shock vector. Charging of capacitors to a programmed pulse amplitude and discharging of the capacitors for a programmed pulse width may be performed by therapy delivery circuit 84 according to control signals received from control circuit 80. Control circuit 80 may include various timers or counters that control when cardiac pacing pulses are delivered. For example, timing circuit 90 may include programmable digital counters set by a microprocessor of the control circuit 80 for controlling the basic pacing time intervals associated with various pacing modes or ATP sequences delivered by ICD 14. The microprocessor of control circuit 80 may also set the amplitude, pulse width, polarity or other characteristics of the cardiac pacing pulses, which may be based on programmed values stored in memory 82.

In response to detecting VT or VF, control circuit 80 may schedule a therapy and control therapy delivery circuit 84 to generate and deliver the therapy, such as ATP and/or CV/DF therapy. Therapy can be generated by initiating charging of high voltage capacitors via a charging circuit, both included in therapy delivery circuit 84. Charging is controlled by control circuit 80 which monitors the voltage on the high voltage capacitors, which is passed to control circuit 80 via a charging control line. When the voltage reaches a predetermined value set by control circuit 80, a logic signal is generated on a capacitor full line and passed to therapy delivery circuit 84, terminating charging. A CV/DF pulse is delivered to the heart under the control of the timing circuit 90 by an output circuit of therapy delivery circuit 84 via a control bus. The output circuit may include an output capacitor through which the charged high voltage capacitor is discharged via switching circuitry, e.g., an H-bridge, which determines the electrodes used for delivering the cardioversion or defibrillation pulse and the pulse wave shape.

In some examples, the high voltage therapy circuit configured to deliver CV/DF shock pulses can be controlled by control circuit 80 to deliver pacing pulses, e.g., for delivering ATP, post shock pacing pulses or ventricular pacing pulses. In other examples, therapy delivery circuit 84 may include a low voltage therapy circuit for generating and delivering pacing pulses for a variety of pacing needs.

Sensor(s) 94 may include one or more sensors configured to produce a cardiac signal having a cyclical or pulsatile waveform corresponding to cardiac events that each occur within a respective cardiac cycle. Sensor(s) 94 may sense a cardiac event, such as a heart sound, systolic blood pressure waveform, impedance waveform, or other pulsatile event signal associated with a heartbeat. Sensor(s) 94 may pass cardiac sensed event signals to control circuit 80 and may determine a sensed cardiac event feature associated with each sensed event signal. In other examples, control circuit 80 may sense cardiac events from a sensor signal received from sensor(s) 94 and/or determine the event feature from the sensor signal in response to a sensed event signal from the sensor. Techniques described herein for sensing cardiac electrical events, determining sensed event features and sensed event intervals, and analyzing the sensed event features and event intervals based on an alternative sensing control parameter setting to predict which cardiac events in cardiac event data obtained by ICD 14 (or another medical device) will still be sensed may be applied to other cardiac signals sensed by sensor(s) 94.

It is recognized that the methods disclosed herein for determining and analyzing sensed cardiac event signal features and sensed event intervals may be implemented in a medical device system that is used for monitoring cardiac electrical signals by sensing circuit 86 and/or other cardiac signals by sensor(s) 94 without necessarily having therapy delivery capabilities or in a pacemaker that monitors cardiac electrical signals and delivers cardiac pacing therapies by therapy delivery circuit 84, without high voltage therapy capabilities, such as cardioversion/defibrillation shock capabilities.

Control parameters utilized by control circuit 80 for sensing cardiac events and controlling therapy delivery may be programmed into memory 82 via telemetry circuit 88. Telemetry circuit 88 includes a transceiver and antenna for communicating with external device 40 (shown in FIG. 1A) using RF communication or other communication protocols as described above. Under the control of control circuit 80, telemetry circuit 88 may receive downlink telemetry from and send uplink telemetry to external device 40. Telemetry circuit 88 may transmit sensed cardiac event features and associated sensed event intervals to another medical device for processing an analysis according to the techniques disclosed herein. In other examples, control circuit 80 may be configured to perform the analysis of cardiac event signal features and sensed event intervals and control telemetry circuit 88 to transmit the data resulting from and/or used in the analysis.

Figure 6:
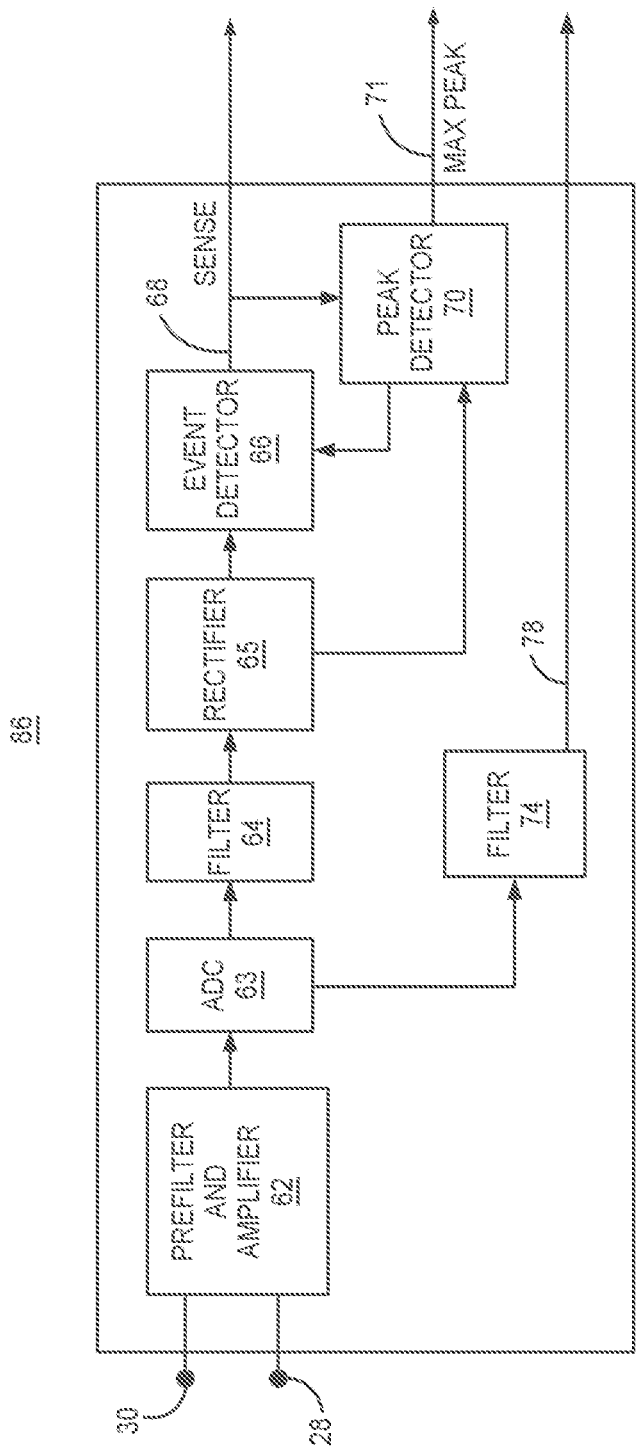
FIG. 6 is a conceptual diagram of circuitry that may be included in the sensing circuit of FIG. 5 according to one example.

FIG. 6 is a conceptual diagram of circuitry that may be included in sensing circuit 86 according to one example. Sensing circuit 86 is coupled to a sensing electrode vector, which may include any available electrodes selected for sensing cardiac electrical signals and is shown as pace/sense electrodes 28 and 30 as an example. In other examples, the sensing electrode vector coupled to sensing circuit 86 may include a defibrillation electrode 24 and/or 26 and/or housing 15.

The electrical signal developed across the sensing electrode vector, e.g., electrodes 28 and 30, is received as a differential input signal to the pre-filter and pre-amplifier 62. Non-physiological high frequency and DC signals may be filtered by a low pass or bandpass filter included in pre-filter and pre-amplifiers 62, and high voltage signals may be removed by protection diodes included in pre-filter and pre-amplifier 62. Pre-filter and pre-amplifier 62 may amplify the pre-filtered signal by a gain of between 10 and 100, and in one example a gain of 17.5, and may convert the differential signal to a single-ended output signal passed to analog-to-digital converter (ADC) 63. Pre-filter and amplifier 62 may provide anti-alias filtering and noise reduction prior to digitization.

ADC 63 converts the cardiac electrical signal from an analog signal to a digital bit stream. In one example, ADC 63 may be a sigma-delta converter (SDC), but other types of ADCs may be used. In some examples, the output of ADC 63 may be provided to a decimator (not shown), which functions as digital low-pass filter that increases the resolution and reduces the sampling rate of the cardiac electrical signal.

The digital output of ADC 63 may be passed to a digital bandpass filter 64. Filter 64 may have a relatively narrow bandpass of approximately 13 Hz to 39 Hz for passing cardiac electrical event signals, such as R-waves, typically occurring in this frequency range. In some examples, the digital output of ADC 63 may be passed to a wideband filter 74 have a bandpass of approximately 2.5 to 100 Hz. In some examples, filter 74 may include a notch filter to attenuate 60 Hz or 50 Hz line noise.

The narrowband filtered signal is passed from filter 64 to rectifier 65 to produce a filtered, rectified signal that is received by a cardiac event detector 66 for sensing cardiac events in response to the narrowband filtered and rectified signal crossing a cardiac event sensing threshold amplitude, for example an R-wave sensing threshold amplitude. In some examples, cardiac event detector 66 may include a P-wave detector for producing atrial sensed event signals in response to a P-wave sensing threshold and/or a T-wave detector for producing a T-wave sensed event signal in response to a T-wave sensing threshold crossing. Cardiac event detector 66 may include an auto-adjusting sense amplifier, comparator and/or other detection circuitry that compares the narrowband filtered and rectified cardiac electrical signal to a cardiac event sensing threshold amplitude in real time and produces a sensed event signal 68, which may be a ventricular sensed (VS) event signal or an atrial sensed (AS) event signal, when the filtered, rectified signal crosses the cardiac event sensing threshold amplitude outside of any blanking intervals applied by sensing circuit 86. A cardiac event sensing threshold applied by cardiac event detector 66 may be a multi-level sensing threshold, for example as generally disclosed in commonly assigned U.S. Pat. No. 10,252,071 (Cao, et al.), incorporated herein by reference in its entirety.

The rectified signal output from rectifier 65 may be passed to a peak detector 70, which may include a sample and hold circuit, for detecting the maximum peak amplitude of the rectified signal following a cardiac sensed event signal 68 produced by cardiac event detector 66. The maximum peak amplitude may be passed back to cardiac event detector 66 for setting the starting cardiac event sensing threshold amplitude for starting the next cardiac cycle based on the detected maximum peak amplitude of the currently sensed cardiac event. The sensing threshold amplitude may be set to a starting amplitude that is a percentage of the maximum peak amplitude, e.g., 60%, 70%, 80% or other selected percentage. The starting sensing threshold amplitude may be held for a time interval or decay over a decay interval. The sensing threshold amplitude may be decreased over one or more decay intervals and/or be decreased by a step drop in amplitude one or more times until it reaches the minimum sensing threshold amplitude equal to the programmed sensitivity. The techniques described herein are not limited to a specific behavior of the sensing threshold amplitude as it is decreased from a starting amplitude based on the maximum peak amplitude of the most recently sensed cardiac event signal to a programmed sensitivity.

The maximum peak signal 71 indicates the maximum peak amplitude of the sensed cardiac event signal and is passed to control circuit 80 and/or memory 82. The maximum peak signal 71 may include a time stamp indicating the time of the maximum peak. The maximum peak amplitude and associated time stamp may be buffered in memory 82. In some examples, the maximum peak amplitude is stored along with a time stamp of the sensed event signal 68 received by control circuit 80 and/or the time stamp of the maximum peak. In this way, a sensed event interval determined by control circuit 80 and the corresponding maximum peak amplitude of the sensed cardiac event (ending the determined sensed event interval) may be stored in memory 82 in a buffer, which may be configured to store a predetermined number of cycles, e.g., on a first in first out basis. As described below, the maximum peak amplitudes and corresponding sensed event intervals may be used by control circuit 80 or an external processor or computer, e.g., processor 52 of eternal device 40 (FIG. 1A), for determining which of the sensed cardiac events are predicted to be sensed when an alternative sensitivity setting is used.

The maximum peak amplitude of each sensed event is an event feature that may be stored in memory 82 with the corresponding event interval as sensed cardiac event data that is analyzed for predicting which of the sensed cardiac events would still be sensed at a different sensitivity (or other programmable sensing control parameter) setting than the currently programmed settings used by sensing circuit 86 for sensing the cardiac events. By storing only the cardiac event feature, e.g., maximum peak amplitude, and the sensed event time interval, control circuit 80 or another processor may analyze the sensed cardiac event data to predict the cardiac events that would be sensed using different sensing control parameter settings without requiring storage of the cardiac signal itself. Storage of the cardiac signal may require significantly higher memory capacity which may limit the number of and/or duration of cardiac signal episodes that may be stored and analyzed. When another medical device processor is performing the analysis of the sensed cardiac event data, the data may be transmitted with relatively less transmission power and time than required to transmit a stored cardiac signal episode for analysis by another medical device.

Sensing circuit 86 may include wideband filter 74 for producing a cardiac EGM or ECG signal 78 that is passed to control circuit 80 for performing morphological analysis of the cardiac signal waveforms. For example, control circuit 80 may perform morphology analysis of the wideband filtered cardiac electrical signal to detect and distinguish R-waves arising from non-sinus tachycardia or fibrillation waves from normally conducted R-waves. While a single sensing electrode vector is shown for passing a signal to both narrowband filter 64 for cardiac event sensing and wideband filter 74 for morphology signal analysis, in other examples, different sensing electrode vectors may be coupled to sensing circuit 86 for passing different cardiac electrical signals to the narrowband filter 64 and the wideband filter 74. In some examples, sensing circuit 86 may include two sensing channels including different filters, amplifiers, ADCs and/or other signal processing circuitry such that two different filtered signals are produced by the respective sensing channels for use in sensing cardiac event signals and/or for morphology analysis or other signal analyses. The configuration of sensing circuit 86 as shown in FIG. 6 is illustrative in nature and should not be considered limiting of the techniques described herein. Sensing circuit 86 may include more or fewer components than illustrated and described in FIG. 6 and some components may be shared between multiple sensing channels.

Figure 7:
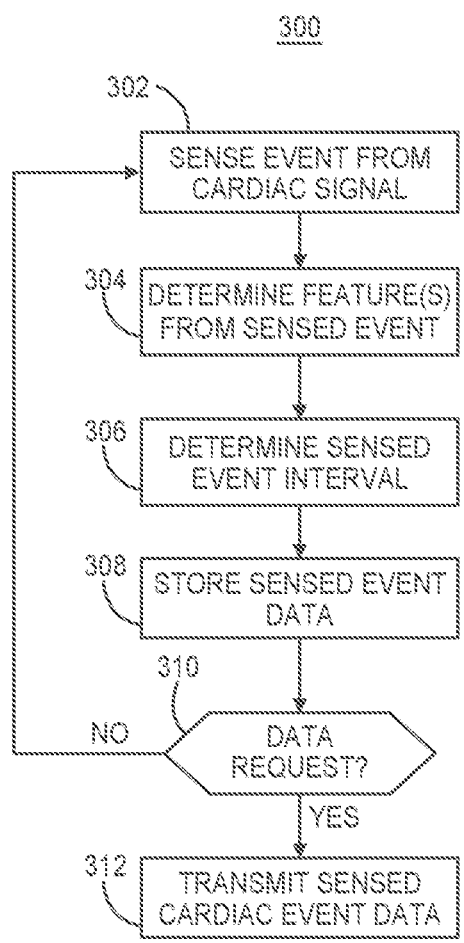
FIG. 7 is a flow chart of a method that may be performed by a medical device for sensing cardiac events from a cardiac signal according to one example.

FIG. 7 is a flow chart 300 of a method that may be performed by a medical device for sensing cardiac events from a cardiac signal according to one example. At block 302, sensing circuit 86 may sense a cardiac event from a cardiac electrical signal. For example, cardiac event detector 66 may sense a cardiac event such as a P-wave or R-wave in response to the cardiac signal crossing a sensing threshold. In response to sensing the cardiac event, the cardiac event detector 66 may produce a cardiac sensed event signal as described above. At block 304, the sensing circuit 86 (or in some examples control circuit 80) may determine an event feature from the sensed cardiac event. In one example, the event feature is the maximum peak amplitude of the sensed cardiac event, e.g., the maximum peak P-wave amplitude or the maximum peak R-wave amplitude, which follows the cardiac sensed event signal during a post-sense blanking interval.

In other examples, the feature determined from the sensed event may depend on the criteria used by sensing circuit 86 for sensing the cardiac event. For instance, sensing circuit 86 may include a slew rate detector for determining the slew rate of the cardiac event signal. An R-wave, for example, may be sensed by the cardiac event detector 66 at block 302 in response to the detected slew rate exceeding a slew rate threshold. In this case, the maximum slew rate of the cardiac event may be determined as the event feature at block 304. Other features of a sensed event that may be determined at block 304 may include waveform morphology attributes such as signal width, signal area, frequency content or the like which may be compared to respective thresholds or ranges for determining if a cardiac event is sensed. When other event features do not meet cardiac event sensing criteria, the sensed event according to the sensing threshold crossing may be identified as a non-cardiac event. For example, if the morphology of the waveform does not match an R-wave morphology template, the signal width is wider or narrower than an R-wave threshold range, or the frequency content is above a noise threshold, the sensed event may be identified as a non-cardiac event and ignored for the purposes of storing sensed cardiac event data and/or rejected in the analysis of the sensed cardiac event data according to different sensing control parameter settings. It is understood that more than one feature may be determined from each sensed cardiac event at block 304. In some examples, cardiac event sensing techniques may rely on one or more cardiac signal features meeting a respective threshold or criterion for sensing the cardiac event, which may include discriminating between cardiac and non-cardiac (e.g., noise) events. As such, in some examples, multiple features of the sensed cardiac event may be determined at block 304.

At block 306, control circuit 80 may determine the sensed event interval associated with the currently sensed cardiac event. The sensed event interval may be determined by timing circuit 90 as the time interval from the most recent preceding cardiac sensed event signal received from sensing circuit 86 to the current sensed event signal. The sensed event interval and associated maximum peak amplitude (or other determined feature) of the current sensed event may be stored in memory 82 at block 308 as sensed cardiac event data.

The sensed cardiac event data, including the maximum peak amplitudes (and/or other sensed event features) and the sensed event interval are stored in memory 82 at block 308. In some examples, rather than storing the sensed cardiac event intervals, a time stamp at the time that a cardiac sensed event signal is received, or the time stamp of the associated maximum peak amplitude, may be stored in memory 82 with the determined maximum peak amplitude. The sensed cardiac event data may be stored in memory 82 at block 308 to fill a buffer corresponding to an episode of the cardiac signal and associated sensed cardiac events. As described below, the method of flow chart 300 may be performed to obtain sensed cardiac event data during an induced tachyarrhythmia. At other times, the method of flow chart 300 may be performed during a spontaneous tachyarrhythmia episode. For example, the process of flow chart 300 may be performed when an increased heart rate is detected by control circuit 80 and the onset of a spontaneous tachyarrhythmia episode is suspected due to the increased heart rate. In this way, sensed cardiac event data associated with a spontaneously occurring tachyarrhythmia may be obtained.

In some examples, the data may be determined and buffered in memory until a predetermined number of sensed cardiac event data buffers are filled, which may be overwritten on a regularly scheduled basis. In other examples, the sensed cardiac event data may be determined on an ongoing basis, filling the sensed cardiac event data buffer on a first-in-first-out basis. In this way, if control circuit 80 detects a tachyarrhythmia or other cardiac arrhythmia episode of interest, the buffered sensed cardiac event data associated with the arrhythmia episode may be saved for analysis according to at least one different sensing control parameter. In other examples, the sensed cardiac event data may be determined over a specified time interval or specified number of sensed cardiac events at scheduled times. The data may be obtained over a time interval that corresponds to cardiac event sensing with no pacing or cardiac event sensing with intermittent pacing.

In some examples, control circuit 80 may perform subsequent analysis of the sensed cardiac event data such that transmission of the data to another device is not required. In other examples, however, the sensed cardiac event data may be stored in memory 82 for transmission to another medical device for performing analysis of the data. As such, at block 310, telemetry circuit 88 may receive a data request from another medical device, e.g., external device 40. In response to the data request received by telemetry circuit 88, control circuit 80 may retrieve the stored sensed cardiac event data from memory 82 and control telemetry circuit 88 to transmit the stored sensed cardiac event data at block 312. In other examples, telemetry circuit 88 may transmit the sensed cardiac event data without waiting for a data request at block 310. For example, when the sensed cardiac event data is acquired during an induced tachyarrhythmia or other device testing or programming session, telemetry circuit 88 may be in communication with the telemetry circuit of external device 40 and transmit the sensed cardiac event data as it is acquired or after all data for a cardiac signal episode is acquired.

The data transmitted at block 312 may be analyzed by a processor of another device, e.g., external device 40 or a computer receiving data from external device 40. As described below, the transmitted sensed cardiac event data may be analyzed according to a setting of a programmable sensing control parameter that is different than the setting currently programmed and used by sensing circuit 86 to sense the cardiac events associated with the transmitted data. By analyzing the sensed cardiac event data according to a different sensing control parameter setting, the processor may predict which cardiac events will be sensed according to a different sensing control parameter and determine sensed event intervals associated with the predicted sensed events. The processor may determine a change in a time to detect a tachyarrhythmia and/or an expected change in the therapy response of ICD 14 when differences in the sensed event intervals exist based on the different sensing control parameter setting. The predicted sensed cardiac events, predicted sensed event intervals, and a predicted time to detect a tachyarrhythmia may be determined by the processor based only the cardiac event data without requiring transmission or storage of the cardiac signal from which the actual sensed cardiac event data is obtained.

In the illustrative examples presented herein, a processor of another device, such as external device 40, a personal computer, a tablet, personal handheld or other device processor may receive the transmitted sensed cardiac event data and perform an analysis of the sensed cardiac event data based one or more different settings of a programmable sensing control parameter. However, it is recognized that in any of the examples presented herein, the processor performing the analysis of the sensed cardiac event data may be a processor 81 included in control circuit 80. In this case, the sensed cardiac event data need not be transmitted by telemetry circuit 88 but may be stored in memory 82 and retrieved by processor 81 for analysis according to the techniques disclosed herein.

Figure 8:
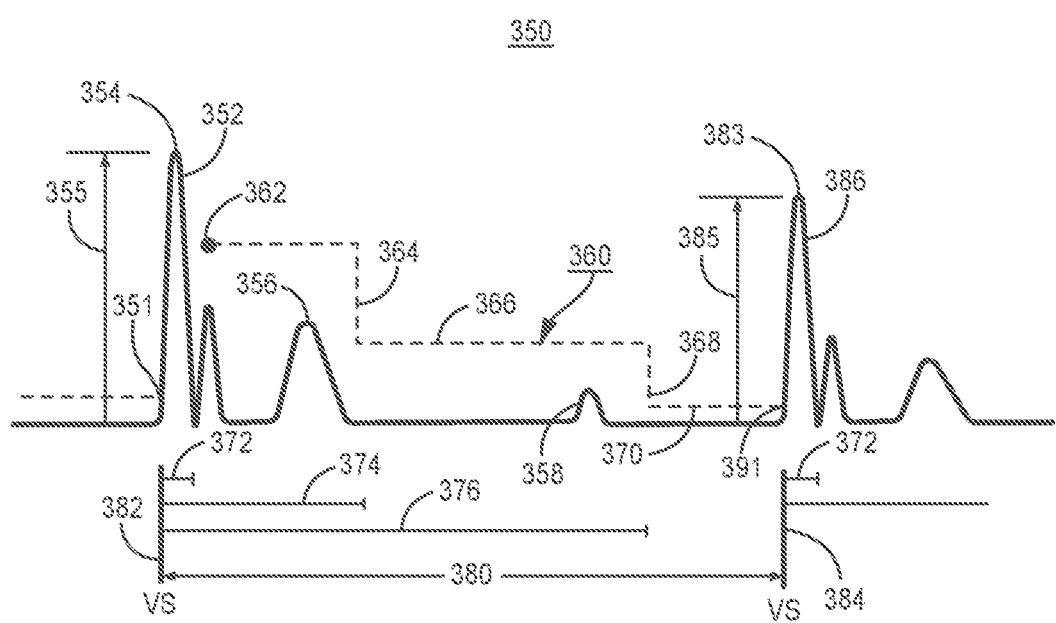
FIG. 8 is a diagram of a filtered and rectified cardiac electrical signal.

FIG. 8 is a diagram of a filtered and rectified cardiac electrical signal 350 including an R-wave 352, a T-wave 356, and a P-wave 358 and an automatically adjusted R-wave sensing threshold 360 that is adjusted between a starting threshold 362 and the programmed sensitivity 370. The starting threshold 362 may be determined as a percentage of the maximum peak amplitude 355 of sensed R-wave 352. R-wave 352 is sensed upon sensing threshold crossing 351. Sensing circuit 86 produces a VS event signal 382 in response to the sensing threshold crossing 351. Sensing circuit 86 may be configured to detect the maximum peak 354 of R-wave 352. The maximum peak 354 may be detected during a post-sense blanking interval 372, e.g., by peak detector 70 shown in FIG. 6. The amplitude 355 of the maximum peak 354 may be used by sensing circuit 86 to set the starting R-wave sensing threshold 362. In some examples, the starting R-wave sensing threshold 362 may be set to a percentage of maximum peak amplitude 355, e.g., between 55% and 70% of the maximum peak amplitude 355, or another selected percentage, which may be 62.5% in one example.

The starting threshold 362 may be held for a sense delay interval 374 to avoid oversensing T-wave 356 as an R-wave. In other examples, the starting threshold 362 may decay at a specified decay rate for a predetermined decay interval. In the example shown, R-wave sensing threshold 360 is decreased by a step decrement 364 upon expiration of sense delay interval 374. Sense delay interval 374 may be between 300 and 400 ms, as examples, and is 360 ms in one example. At the expiration of sense delay interval 374, sensing circuit 86 adjusts the R-wave sensing threshold 360 from the starting amplitude 362 set to a first percentage of maximum peak amplitude 355 to an intermediate sensing threshold amplitude 366 that is a second percentage of R-wave maximum peak amplitude 355 that is less than the first percentage. Intermediate sensing threshold amplitude 366 may be set to between 25% and 60% of the maximum peak amplitude 355 or between 30% and 35% of the maximum peak amplitude 355 as examples. Intermediate sensing threshold amplitude 366 is less than the starting sensing threshold amplitude 362 by step decrement 364.

R-wave sensing threshold 360 may be held at the intermediate amplitude 366 for a drop time interval 376 as shown in FIG. 8. In other examples, R-wave sensing threshold 360 may decay at a specified decay rate from the expiration of the sense delay interval 374 until the expiration of drop time interval 376 or until reaching the sensing floor equal to the programmed sensitivity 370. In the example shown, upon expiration of drop time interval 376, sensing circuit 86 adjusts R-wave sensing threshold 360 from the intermediate sensing threshold amplitude 366 to the sensitivity 370 in a step decrement 368. The sensitivity 370 defines the minimum sensing threshold amplitude or sensing floor of R-wave sensing threshold 360. The drop time interval 376 may be between 1 second and 2 seconds and is 1.5 seconds in one example. The sensitivity 370 may be programmable over a range of 0.075 millivolts (mV) to 1.2 mV, as examples, though lower or higher sensitivity settings may be available.

Each of the first percentage used to set starting sensing threshold amplitude 362 as a percentage of maximum peak amplitude 355, the second percentage used to set intermediate sensing threshold amplitude 366 as a percentage of maximum peak amplitude 355, the sensitivity 370, the post-sense blanking interval 372, the sense delay interval 374 and the drop time interval 376 may be programmable or adjustable sensing control parameters. Accordingly, processor 52 of external device 40 (and/or control circuit 80) may be configured to analyze sensed cardiac event data to determine predicted sensed cardiac events according to one or more different settings of one sensing control parameter or combinations of different settings of two or more sensing control parameters. In illustrative examples described below, control circuit 80 or programmer 52 of external device 40 is configured to at least determine predicted sensed cardiac events according to different settings of sensitivity 370.

As shown in FIG. 8, R-wave sensing threshold 360 is held at sensitivity 370 until the cardiac electrical signal 350 crosses the sensing threshold 360, at sensing threshold crossing 391, resulting in the next VS event signal 384 produced by sensing circuit 86. It is to be understood that the cardiac electrical signal 350 may not cross the sensing threshold 360 before a pacing interval expires during some cardiac cycles. In this case, therapy delivery circuit 84 may generate and deliver a pacing pulse. At other times, the next R-wave 386 may occur earlier after R-wave 352, before R-wave sensing threshold 360 reaches sensitivity 370 (before drop time interval 376 expires) or even before R-wave sensing threshold 360 reaches the intermediate sensing threshold amplitude 366 (before sense delay interval 374 expires). The cardiac event interval 380, which is an RRI in this example, may be determined by control circuit 80 (or processor 52 of external device 40) as the time interval between VS event signal 382 corresponding to threshold crossing 351 and VS event signal 384 corresponding to threshold crossing 391.

The maximum peak 383 is identified during the next post-sense blanking interval 372 and the maximum peak amplitude 385 is determined. The maximum peak amplitude 385 and the associated RRI 380 may be stored in a sensed cardiac event buffer in memory 82 for use in subsequent analysis of alternative sensing control parameters.

It is to be understood that the next R-wave 386 may occur earlier in time after sensed R-wave 352 and cross the sensing threshold 360 before sensing threshold 360 reaches the minimum sensing threshold 370 during some ventricular cycles, particularly during fast ventricular rates. It is also to be understood that the cardiac electrical signal 350 may not cross the sensing threshold 360 before a pacing interval expires during some cardiac cycles. In this case, therapy delivery circuit 84 may generate and deliver a pacing pulse. A maximum peak amplitude of an R-wave may not be recorded for a paced cycle. In this case, control circuit 80 may store the maximum peak amplitude of the most recent sensed cardiac event or store the average of a predetermined number of most recently sensed cardiac events. In this way, a maximum peak amplitude is available for setting the starting sensing threshold 362 following a paced event, e.g., at the expiration of a post-pace blanking period.

The particular behavior of R-wave sensing threshold 360 shown in FIG. 8 as it is adjusted between the starting threshold amplitude 362, set based on the maximum peak amplitude 355, and the sensitivity 370 is one illustrative example of how sensing circuit 86 may adjust the sensing threshold 360. It is to be understood that a variety of cardiac event sensing threshold control parameters, e.g., R-wave sensing threshold control parameters for ventricular rate determination or P-wave sensing threshold control parameters for atrial rate determination, may include one or more decay rates, each associated with a decay interval, and/or one or more step decrements, each associated with a drop time interval. Various sensing control parameters may be used by sensing circuit 86 for adjusting the R-wave sensing threshold 360 between the starting threshold 362 and sensitivity 370. For example, the R-wave sensing threshold 360 may decay, linearly or non-linearly, from starting sensing threshold amplitude 362 to sensitivity 370 at a predetermined decay rate until a sensing threshold crossing or a pacing interval expires, whichever occurs first.

The techniques disclosed herein for determining sensed cardiac event data are not limited for use with any particular sensing threshold control parameters or sensing threshold adjustment schemes. The sensing control parameters used by sensing circuit 86 to adjust sensing threshold 360, however, are the same sensing control parameters used by control circuit 80 and/or external device processor 52 for determining predicted sensed cardiac events during post processing of the sensed cardiac event data. At least one different setting of at least one sensing control parameter is used, however, in determining the predicted sensed cardiac events. For example, one or more sensitivity settings that are greater than sensitivity 370 may be applied to determine predicted sensed cardiac events. In another example, one or more drop time intervals that are longer than drop time interval 376 may be applied to determine predicted sensed cardiac events. In yet another example, one or more percentages greater than the percentage used to set the starting sensing threshold 362 and/or the intermediate threshold 366 based on a most recent maximum peak amplitude may be applied to the sensed cardiac event data.

Since the sensed cardiac event data obtained by ICD 14 excludes any undersensed cardiac events, analysis of sensing control parameters that increase the sensitivity to sensing cardiac events may be omitted. For example, analyzing the sensed cardiac event data using a sensitivity setting that is lower than sensitivity 370 is not expected to change the sensed event intervals since all cardiac events sensed using the sensitivity 370 are also expected to be sensed at a lower setting of the sensitivity. However, when the setting of sensitivity 370 is increased, effectively reducing the sensitivity to sensing cardiac events, some cardiac events that are sensed using sensitivity 370 may no longer be sensed according to a higher sensitivity setting. Likewise, if drop time interval 376 is extended to a longer setting and/or the percentage of maximum peak amplitude 355 used to set the staring sensing threshold 362 and/or the intermediate threshold 366 is higher, the sensitivity to sensing cardiac events may be decreased, resulting in some sensed cardiac events being predicted as undersensed according to the alternative sensing control parameter settings.

The predicted value of the sensing threshold 360 determined by processor 52 (or control circuit 80) at the time of a sensed event signal (or its maximum peak amplitude) may change from the sensing threshold value actually applied at the time of a sensed event signal for at least two reasons. One reason is that the sensing threshold 360 is likely to reach the minimum sensing threshold earlier in the cardiac cycle when an alternative, higher sensitivity setting is being evaluated compared to the sensing threshold 360 applied according to the programmed sensitivity setting 370. For instance, if the calculated percentage of the maximum peak amplitude 355 used to set the starting sensing threshold 362 or the calculated percentage of the maximum peak amplitude 355 used to set the intermediate sensing threshold 366 is less than the alternative sensitivity setting, due to a low amplitude R-wave or fibrillation wave, the predicted sensing threshold is set equal to the sensitivity setting being analyzed instead of the calculated percentage. The sensitivity setting is the sensing floor or minimum sensing threshold applied to the cardiac signal. Accordingly the predicted sensing threshold at the time of a maximum peak amplitude may be the sensitivity setting under analysis starting from the expiration of the post-sense blanking period 372 in some instances.

Another reason that the predicted value of the sensing threshold at the time of a maximum peak amplitude may change from the actual sensing threshold used to sense the event is that a preceding actual sensed event may be classified as a predicted undersensed event due to its maximum peak amplitude being less than the determined, predicted value of the sensing threshold corresponding in time to the preceding actual sensed event signal. This situation is described below in conjunction with FIG. 9. When an actual sensed event is predicted to be undersensed according to an alternative sensitivity setting, the determined sensing threshold will be decreased according to the maximum peak amplitude of the most recent preceding predicted sensed event and the time since that event down to the higher, alternative sensitivity setting and held at the higher sensitivity setting until the next actual sensed event time after the classified undersensed event. Assuming the next actual sensed event is associated with a maximum peak amplitude greater than the higher sensitivity setting (or other predicted value of the sensing threshold at the time of the next actual sensed event), the next actual sensed event may be classified by processor 52 as a predicted sensed event according to the alternative sensitivity setting. The maximum peak amplitude of the classified sensed event is used as a starting value for determining the sensing threshold over the next ventricular cycle. As such, the predicted behavior of the sensing threshold 360 may be different over one or more cardiac cycles of a cardiac signal episode, resulting in different predicted sensed event intervals between the events classified as predicted sensed events (and excluding events classified as predicted undersensed events).

Figure 9:
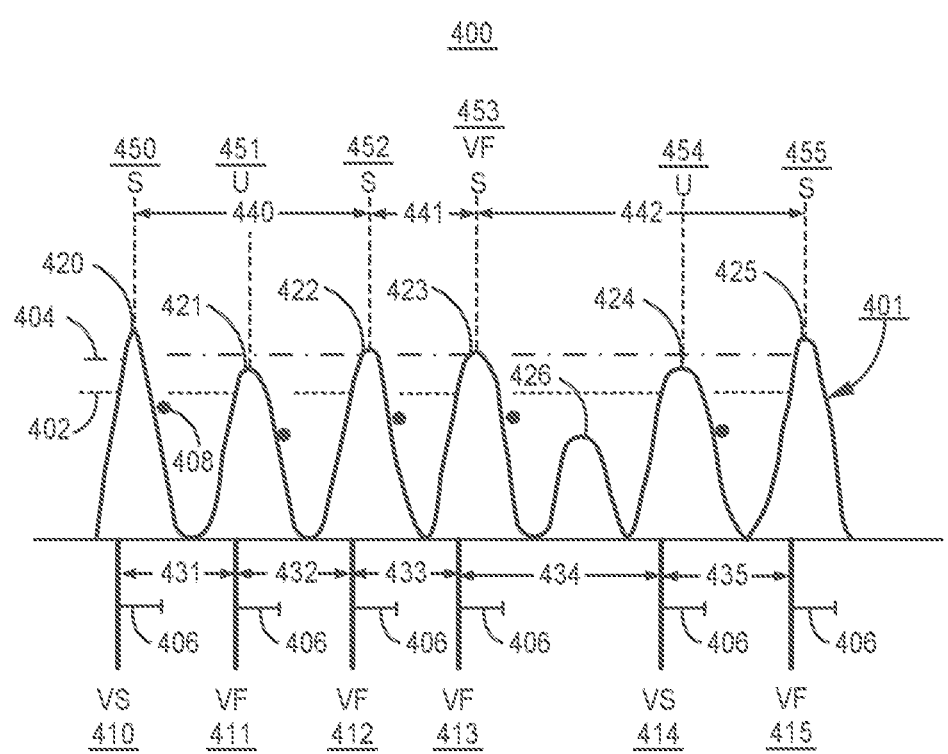
FIG. 9 is a diagram of a filtered rectified cardiac electrical signal during ventricular fibrillation.

FIG. 9 is a diagram 400 of a filtered rectified cardiac electrical signal 401 during ventricular fibrillation. Signal 401 represents a narrowband rectified signal that may be received by cardiac event detector 66 from narrowband filter 64 and rectifier 65. Low amplitude fibrillation waves may be sensed by cardiac event detector 66 according to a programmed sensitivity 402. The first fibrillation wave shown has a maximum peak amplitude 420 and is sensed when the cardiac electrical signal 401 crosses the sensing threshold adjusted to the programmed sensitivity 402. AVS event signal 410 is produced by sensing circuit 86. A post-sense blanking interval 406 is started, and sensing circuit 86 determines the maximum peak amplitude 420 during blanking interval 406.

Sensing circuit 86 may determine the starting sensing threshold 408 as a percentage of the maximum peak amplitude 420. Since this starting sensing threshold 408 is less than the programmed sensitivity 402, however, sensing circuit 86 sets the sensing threshold to the sensitivity 402 upon expiration of blanking interval 406. The next fibrillation wave having maximum peak 421 is sensed when cardiac electrical signal 401 crosses the sensing threshold set to sensitivity 402. Sensing circuit 86 may pass a VS event signal to control circuit 80. Because the VS event signal occurs at a sensed event interval 431 that is within a VF interval range, control circuit 80 counts a VF event 411.

At the programmed sensitivity 402, each fibrillation wave having a maximum peak amplitude 420, 421, 422, 423, 424 and 425 greater than the programmed sensitivity 402 is sensed by sensing circuit 80 at respective sensed event intervals 431, 432, 433, 434 and 435. The starting sensing thresholds indicated by solid black dots, e.g., starting sensing threshold 408, that are determined by sensing circuit 80 based on the respective maximum amplitudes 420, 421, 422, 423, and 424 are all less than the programmed sensitivity 402. As a result the sensing threshold is set to the sensitivity 402 after each blanking interval 406 until the next sensing threshold crossing by cardiac electrical signal 401.

One fibrillation wave having maximum peak amplitude 426 is not sensed according to the programmed sensitivity 402. As such, the sensing threshold started after the blanking interval following VF event 413 is held at the programmed sensitivity 402 until cardiac electrical signal 401 crosses the sensing threshold resulting in VS event signal 414. The associated sensed event interval 434 is longer than the VF interval range so the VS event signal 414 is not counted as a VF event. However, each of the fibrillation waves sensed at a sensed event interval 431, 432, 433 and 435 that is within the VF interval range is counted as a VF event, in this case events 411, 412, 413 and 415. Thus, in the example of FIG. 9, four VF intervals would be counted by control circuit 80 toward VF detection.

The sensed cardiac event data that may be determined and stored by ICD 14 for analysis according to an alternative sensitivity setting 404 may include each of the maximum peak amplitudes 420, 421, 423, 424, and 425 of the sensed events along with the respective associated event interval 431, 432, 433, 434, and 435 (or a time stamp of the maximum peak amplitude or the sensed cardiac event signal to enable determination of the event interval). Since the fibrillation wave having maximum amplitude 426 was not sensed, the maximum peak amplitude 426 is unknown and no sensed cardiac event data is stored corresponding to the unsensed fibrillation wave. The analysis of the sensed cardiac event data according to an alternative sensitivity setting may be performed for sensitivity settings that are higher than the programmed sensitivity setting 402 since no sensed cardiac event data is available regarding lower amplitude R-waves or fibrillation waves that are smaller in amplitude than the programmed sensitivity.

For the sake of convenience, analysis of the stored maximum peak amplitudes 420, 421, 423, 424, and 425 and associated sensed event intervals 431, 432, 433, 434 and 435 according to a higher sensitivity 404 will now be described as being performed by processor 52 of external device 40. External device 40 may retrieve the cardiac event data obtained by ICD 14. It is to be understood, however that in some examples ICD control circuit 80 may perform the analysis of the stored sensed cardiac event data without requiring transmission to the external device 40.

When the alternative higher sensitivity 404 is being applied by processor 52 to the sensed cardiac event data, the first maximum peak amplitude 420 is greater than the higher sensitivity 404 and predicted to be a sensed event 450. Processor 52 uses the sensed event time intervals and associated maximum peak amplitudes of the cardiac event data to construct the sensing threshold according to the same sensing control parameters that would be used by cardiac event detector 66, with the exception of the higher sensitivity 404 in this example. In this way, processor 52 may determine what value the sensing threshold is adjusted to at the time of each of the stored maximum peak amplitudes. Processor 52 may then determine if a given stored maximum peak amplitude is greater than or equal to the predicted value of the sensing threshold at the associated stored sensed event interval. When the stored maximum peak amplitude is greater than or equal to the predicted value of the sensing threshold, the event is a predicted sensed event. When the stored maximum peak amplitude is less than the predicted value of the sensing threshold, the event is a predicted undersensed event.

In the example of FIG. 9, processor 52 determines a value of the starting sensing threshold 408 based on the stored maximum peak amplitude 420. Since the starting sensing threshold 408 based on maximum peak amplitude 420 is less than the higher sensitivity 404, processor 52 determines that the predicted value of the sensing threshold at the end of the stored sensed event interval 431 is equal to the higher sensitivity 404. Since the maximum peak amplitude 421 stored in the sensed cardiac event data associated with cardiac event interval 431 is less than sensitivity 404, processor 52 classifies the maximum peak amplitude 421 as a predicted undersensed event 451.

The maximum peak amplitude 421 is not used to determine a starting threshold since it is classified as undersensed. Processor 52 determines that the predicted sensing threshold is held at the sensitivity 404 until the end of the next stored sensed event interval 432. The maximum peak amplitude 422 associated with the next stored sensed event interval 432 is compared to sensitivity 404. Since maximum peak amplitude 422 is equal to or greater than the sensitivity 404, processor 52 classifies the maximum peak amplitude 422 as a predicted sensed event 452. This classification results in a predicted sensed event interval 440 associated with the predicted sensed event 452. The predicted sensed event interval 440 is greater than a VF interval range and is therefore not determined to be a VF interval by processor 52.

This process of determining the predicted value of the R-wave sensing threshold at the expiration of each sensed event interval 433, 434 and 435 continues with corresponding comparisons of the maximum peak amplitudes 423, 424 and 425 to the predicted sensing threshold value, which is the alternative sensitivity 404 in each of these cases. The maximum peak amplitude 424 is less than sensitivity 404 (predicted at the expiration of sensed event interval 434) so a predicted undersensed event 454 may be made by processor 52. The predicted sensing threshold is held at sensitivity 404 until the end of the next sensed event interval 435 associated with a maximum peak amplitude 425. Processor 52 determines that maximum peak amplitude 425 is greater than the predicted value of the sensing threshold at sensitivity 404 and determines maximum peak amplitude 425 as a predicted sensed event 455.

After classifying each of the maximum peak amplitudes 421-425 according to the predicted sensing threshold value determined at the expiration of each sensed event interval 431-435, respectively, processor 52 may determine predicted sensed event intervals 440, 441 and 442 between predicted sensed events 450, 452, 454 and 455. Since two maximum peak amplitudes 451 and 454 are predicted to be undersensed events 451 and 454 according to the alternative sensitivity 404, processor 52 determines sensed event intervals 440 and 442 that exclude the predicted undersensed events 452 and 454. In this example, only one VF interval 441 is predicted according to the alternative, higher sensitivity 404 compared to four detected VF intervals 431, 432, 433 and 435 during sensing according to the programmed sensitivity 402. As described below, processor 52 may determine sensed event intervals according to an alternative sensitivity setting to predict a time of tachyarrhythmia detection and/or therapy delivery according to the alternative sensitivity.

The processor 52 of external device 40 may determine predicted sensed event intervals based on the classification of the stored maximum peak amplitudes as either undersensed or sensed based on one or more alternative sensitivity settings. The predicted sensed event intervals may be used by the processor 52 to determine when an arrhythmia detection and/or therapy response by ICD 14 is predicted to be different than an actual arrhythmia detection and/or therapy response to the actual sensed cardiac events (that are sensed according to the programmed sensitivity setting).

Figure 10:
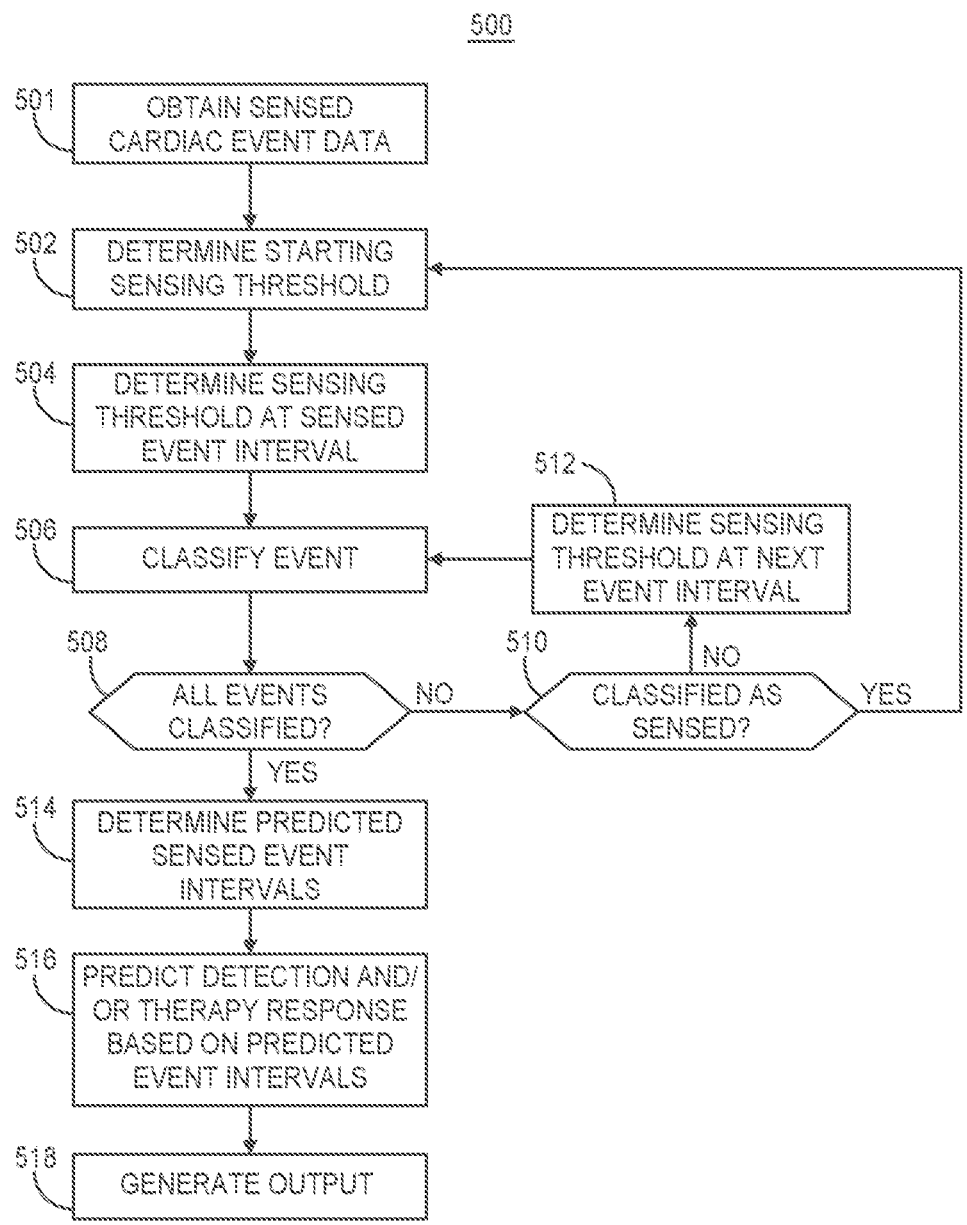
FIG. 10 is a flow chart of a method performed by a medical device system, such as the system of FIG. 1A, according to one example.

FIG. 10 is a flow chart 500 of a method performed by a medical device, such as external device 40 of FIG. 1A, according to one example. The process of flow chart 400 is described as being executed by external device processor 52 for the sake of convenience but may be performed by processor 81 of ICD 14 by retrieving sensed cardiac event data from memory 82 in other examples.

At block 501, processor 52 may obtain sensed cardiac event data from a medical device, e.g., ICD 14. Processor 52 may obtain the sensed cardiac event data by transmitting an interrogation command to ICD 14 via telemetry unit 58. Retrieval of the sensed cardiac event data may be initiated by a user interacting with user interface 56 in some examples. The sensed cardiac event data may correspond to an episode of normal sinus rhythm, bradycardia, tachycardia, fibrillation or other rhythm. In other examples, as described below, the sensed cardiac event data may be determined by ICD 14 during a tachyarrhythmia episode induced during a tachyarrhythmia induction procedure and transmitted to external device 40. As described in conjunction with FIG. 7, the sensed cardiac event data may include the maximum peak amplitude of each cardiac event sensed during the cardiac rhythm episode and a sensed event time interval associated with each maximum peak amplitude.

At block 502, processor 52 determines a starting sensing threshold based on the first maximum peak amplitude of the sensed cardiac event data. Based on this first starting sensing threshold, the sensed event interval associated with the second maximum peak amplitude, and an alternative sensitivity setting, processor 52 determines the predicted value of the sensing threshold at the expiration of the first sensed event interval (e.g., interval 431 of FIG. 9) at block 504. At block 506, processor 52 compares the predicted sensing threshold to the second maximum peak amplitude of the sensed cardiac event data (e.g., peak amplitude 421 of FIG. 9) to classify the second maximum peak amplitude as a predicted sensed event or a predicted undersensed event according to the alternative sensitivity setting. If the second maximum peak amplitude is greater than the predicted value of the sensing threshold, the second maximum peak amplitude is classified as a predicted sensed event according to the alternative sensitivity setting. If the second maximum peak amplitude is less than the determined sensing threshold value, the second maximum peak amplitude is classified as a predicted undersensed event according to the alternative sensitivity setting.

The alternative sensitivity setting may be less sensitive to sensing cardiac events than the sensitivity setting used to obtain the sensed cardiac event data. For example, a sensitivity setting that is greater than the programmed sensitivity setting in ICD 14 may be applied for predicting the value of the sensing threshold. A higher sensitivity setting corresponds to less sensitivity to sensing cardiac events since cardiac events having a maximum peak amplitude less than the higher sensitivity setting will not be sensed.

Processor 52 may continue the process of determining the predicted value of the sensing threshold at the end of each sensed event interval and comparing the predicted value of the sensing threshold to the maximum peak amplitude associated with the sensed event interval until each maximum peak amplitude of the retrieved sensed cardiac event data is classified at block 506, as determined at block 508. In some examples, processor 52 may compare a second feature of each sensed cardiac event, included in the received sensed cardiac event data, to cardiac event criteria at block 506. As described above, when one or more other event features do not meet cardiac event sensing criteria, the maximum peak amplitude may be associated with a non-cardiac event. For example, if a morphology match score of the sensed cardiac event does not match an R-wave morphology matching threshold, the signal width is wider or narrower than an R-wave threshold range, or the frequency content is above a noise threshold, the associated maximum peak amplitude may be rejected from the sensed cardiac event data as being a non-cardiac event in response to at least one second feature of the sensed cardiac event not meeting cardiac event criteria. The rejected maximum peak amplitude may be ignored by processor 52 in classifying each value of the first feature as one of a predicted sensed event or a predicted undersensed event.

When a maximum peak amplitude is classified as a predicted sensed event ("yes" branch of block 510), its maximum peak amplitude is used by processor 52 to determine the next starting sensing threshold at block 502 for determining the predicted value of the sensing threshold at the end of the next sensed event interval. When a maximum peak amplitude is classified as an undersensed event ("no" branch of block 510), processor 52 determines the sensing threshold at the end of the next sensed event interval (block 512) without determining a starting threshold based on the undersensed maximum peak amplitude. Since a maximum peak amplitude classified as undersensed is not predicted to be sensed according to the alternative sensitivity setting, the maximum peak amplitude is not used in determining a starting sensing threshold. The processor 52 determines the predicted value of the sensing threshold at the end of the next sensed event interval without adjusting the sensing threshold based on the maximum peak amplitude classified as undersensed. The sensing threshold is determined according to the sensing threshold control parameters from the starting sensing threshold based on the most recent maximum peak amplitude classified as a sensed event until the expiration of the next sensed event interval after the maximum peak amplitude classified as an undersensed event. This situation is represented in FIG. 9 by the predicted undersensed event 454. The predicted value of the sensing threshold at the expiration of the sensed event interval 435 is determined by processor 52 based on any adjustments of the sensing threshold since the expiration of the post-sense blanking interval 406 following the most recent predicted sensed event 453. In this example, the predicted sensing threshold at the expiration of the next sensed event interval 435 is the higher sensitivity 404.

The maximum peak amplitude associated with the next sensed event interval (e.g., maximum peak amplitude 425) is classified by processor 52 based on a comparison of the maximum peak amplitude to the predicted value of the sensing threshold that ignores any intervening predicted undersensed events. When all maximum peak amplitudes of the sensed cardiac event data have been classified, processor 52 may determine (at block 514) new event intervals between events classified as predicted sensed events and ignore the events classified as predicted undersensed events. As shown in FIG. 9 and described above, an undersensed classification results in a different sensed event interval (e.g., interval 442) than the actual sensed event intervals (e.g., intervals 434 and 435) received from ICD 14 in the sensed cardiac event data.

At block 516, processor 52 may determine when an arrhythmia is expected to be detected based on the predicted sensed event intervals and/or predict when a therapy is expected to be delivered based on the predicted sensed event intervals. For example, processor 52 may determine a predicted sensed event interval that is longer than a programmed pacing lower rate interval and predict delivery of a pacing pulse. As shown in the example of FIG. 9, processor 52 may determine a predicted sensed event interval that is longer than a programmed tachyarrhythmia interval range due to an undersensed event classification. When the sensed cardiac event data corresponds to a tachyarrhythmia episode, one or more predicted sensed event intervals that are longer than tachyarrhythmia event intervals (e.g., VT, VF, AT or AF intervals) stored in the sensed cardiac event data may result in a delay of a tachyarrhythmia detection based on the higher sensitivity setting (or other sensing control parameter setting) or prevent the tachyarrhythmia detection altogether.

In the example of FIG. 9, only one predicted sensed event interval 441 is determined as a VF interval compared to four VF intervals (431, 432, 433, and 435) in the sensed cardiac event data. As a result, the higher sensitivity 404 may delay or prevent detection of VF. At block 516, processor 52 may count the number of tachyarrhythmia intervals in the predicted sensed event intervals to determine when tachyarrhythmia detection criteria are met, if at all, based on the predicted sensed event intervals. Processor 52 may predict when a tachyarrhythmia detection is expected (or not) based on the predicted sensed event intervals and what therapy would be delivered (or not) based on the detection.

In some examples, the sensed cardiac event data may correspond to a VF episode and shock delivery. Based on the predicted sensed or undersensed event classifications according to the alternative sensitivity setting, the predicted sensed event intervals may result in a VT detection and ATP therapy delivery, a VF detection that occurs at the same time as the actual VF detection, a VF detection that occurs later than the actual VF detection such that shock delivery is predicted to occur later than the actual shock delivery, or no VT/VF detection at all and no delivered therapy.

At block 518, processor 52 may generate output based on the predicted sensed event intervals and/or arrhythmia detection. In some examples, the output generated at block 518 includes data for display on display unit 54. The display unit 54 may be a graphical user interface (GUI) that displays a visual representation of the actual sensed cardiac event data, the predicted sensed cardiac events, any predicted undersensed cardiac events, the predicted sensed event intervals, a predicted arrhythmia detection and/or therapy response or any combination thereof. The process of FIG. 10 may be performed for multiple alternative sensitivity settings such that data may be displayed for multiple alternative settings. A user may select a sensitivity setting for programming into ICD 14 based on the displayed data. Examples of GUIs are described below in conjunction with the accompanying drawings.

In some examples, the output generated at block 518 may include a programming command. External device processor 52 may determine a recommended sensing control parameter setting based on the predicted sensed event intervals and/or predicted arrhythmia detection and generate a programming command for transmission to ICD 14 by telemetry unit 58. In some instances, processor 52 may determine a sensitivity setting corresponding to a desired safety margin for detecting a tachyarrhythmia. Processor 52 may generate a programming command to adjust the programmed sensitivity stored in ICD memory 82 to the identified recommended sensitivity setting corresponding to the desired safety margin. When the process of flow chart 500 is performed by control circuit 80 of ICD 14, the output at block 518 may include adjusting the programmed sensitivity setting to a recommended setting determined based on the predicted sensed events. The output may additionally or alternatively include transmitting analysis results to external device 40 for generating a visual representation of the results.

Figure 11:
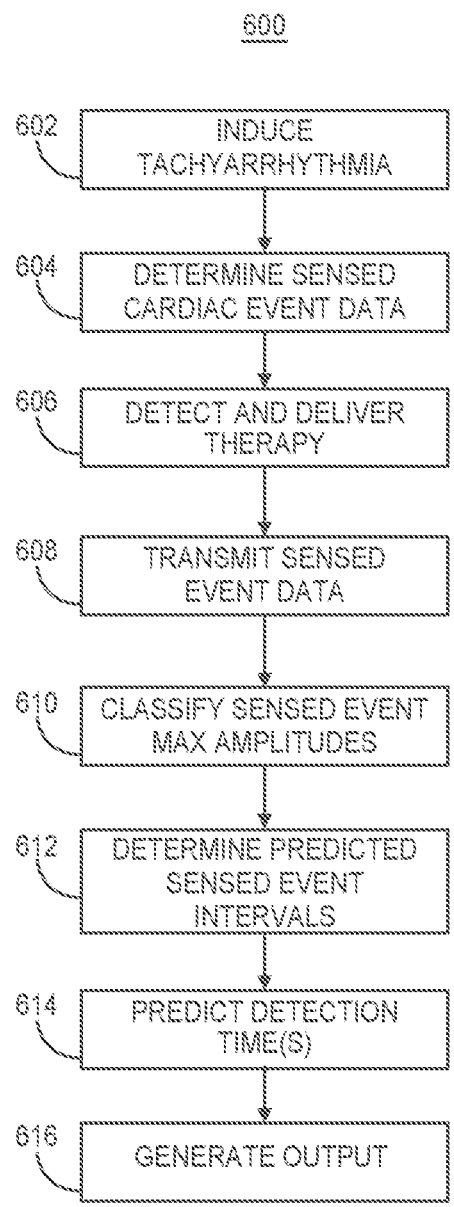
FIG. 11 is a flow chart of a method for evaluating alternative sensing control parameter settings by a medical device system according to another example.

FIG. 11 is a flow chart 600 of a method for evaluating sensed cardiac event data according to alternative sensing control parameter settings by a medical device according to another example. In this example, the sensed cardiac event data determined and stored by ICD 14 is determined during an inducted tachyarrhythmia episode. At block 602, ICD 14 may receive a VF induction command from external device 40 to induce tachyarrhythmia, e.g., by delivering a T-wave shock or a high frequency (e.g., 50 Hz) burst of pulses. ICD 14 senses ventricular events, e.g., R-waves and fibrillation waves, during the induced tachyarrhythmia at block 604 according to the programmed sensitivity and other programmed sensing control parameters. For each sensed event signal produced by sensing circuit 86, ICD 14 determines the maximum peak amplitude and the sensed event interval (or a time stamp associated with the maximum peak amplitude or the sensed cardiac event signal) to store in memory 82 as sensed cardiac event data at block 604.

Control circuit 80 detects the induced tachyarrhythmia, e.g., VF, and delivers therapy, e.g., a shock therapy, according to programmed therapy delivery parameters at block 606. During the induction, detection and therapy delivery, ICD 14 may be transmitting a wideband filtered EGM signal, sensed event markers and event intervals, time of detection and time of a delivered therapy.

At block 608, the sensed cardiac event data including maximum peak amplitudes of sensed events and associated sensed event intervals are transmitted to external device 40. At block 610, processor 52 classifies each of the maximum peak amplitudes of the sensed cardiac event data as a predicted undersensed or sensed event based on one or more alternative sensitivity settings, e.g., using any techniques described above in conjunction with FIGS. 9 and 10. At block 612, processor 52 determines predicted sensed event intervals based on the undersensed and sensed event classifications. Using the predicted sensed event intervals, processor 52 determines a predicted tachyarrhythmia detection time at block 614 for each sensitivity setting evaluated.

Processor 52 may generate an output at block 616 based on the predicted tachyarrhythmia detection times determined at block 614. The generated output may include data generated for display by display unit 54, e.g., in a GUI, which may include a visual representation of a comparison between the actual VF detection time and the predicted detection time for each of the alternative sensitivity settings evaluated. Processor 52 may be configured to determine a safety margin for detecting tachyarrhythmia for one or more sensitivity settings at block 616 as generated output. Methods for determining a safety margin are described below in conjunction with FIG. 14. The safety margin may be determined as the factor of the highest sensitivity setting for which tachyarrhythmia detection is predicted divided by a given, lower sensitivity margin. For example, if VF detection is predicted at 0.9 mV sensitivity and not predicted at sensitivity settings higher than 0.9 mV, the sensitivity setting of 0.45 mV is a predicted 2× safety margin for detecting VF. The sensitivity setting of 0.3 mV is a predicted 3× safety margin for detecting VF and so on.

In some examples, the generated output may include acceptable or recommended sensitivity setting(s) for display on the GUI. In still other examples, the generated output may include a programming command transmitted by external device telemetry unit 58 to program a recommended sensitivity setting for use by sensing circuit 86 in sensing cardiac events.

FIG. 12 is a table 650 of sensed cardiac event data and classifications of predicted sensed and predicted undersensed events of the sensed cardiac event data. Any portion of or all of data listed in table 650 may be generated by processor 52 for display by display unit 54, e.g., in a GUI, in some examples. The data presented in FIG. 12 includes sensed cardiac event data received from ICD 14 and predicted sensed event data determined by an analysis of the sensed cardiac event data. For the sake of convenience, predicted sensed event data presented in FIG. 12 is described as being determined and output by processor 52 of external device 40. As indicated above, however, the predicted sensed event data may be determined by ICD processor 81 and may be transmitted to external device 40 for generating a visual representation of the data in some examples. In still other examples, the ICD processor 81 and the external device processor 52 may cooperatively determine the predicted sensed event data in a distributed manner.

In the first column 652, the sensed cardiac events are numbered and labeled as VF events in this example. The sensed cardiac events of the sensed cardiac event data may be numbered and labeled according to the associated sensed event interval, shown in column 653 as the RRI in milliseconds. For example, the event may be labeled a VS event interval when the sensed event interval is greater than any tachyarrhythmia detection intervals, a VT interval when the sensed event interval falls into a VT interval range, or a VF interval when the sensed event interval falls into a VF interval range. In this example, all RRIs listed in column 653 are less than a programmed VF detection interval, e.g., 320 ms, and identified as VF events in column 652.

The maximum peak amplitude of each of the sensed cardiac events is listed in column 656. The programmed sensitivity used by ICD 14 for sensing the listed sensed cardiac events is indicated in cell 654. In this example, the programmed sensitivity is 0.075 mV, which may be the lowest available sensitivity setting. In the example of flow chart 600 of FIG. 11, external device 40 (or control circuit 80) may temporarily program the sensitivity of ICD sensing circuit 86 to the lowest available setting during the tachyarrhythmia induction procedure. In this way, the sensed cardiac event data will include all cardiac events sensed at the lowest available setting (which is the highest sensitivity for sensing cardiac events). The sensed cardiac event data can be evaluated by external device processor 52 according to all of the alternative sensitivity settings that are higher than the lowest available setting.

In the example table 650 of FIG. 12, the alternative, higher sensitivity settings 660 and 662 of 0.9 mV and 1.2 mV, respectively, are displayed though it is to be understood that one or more or all of the available sensitivity settings greater than the programmed sensitivity setting 654 may be applied to the sensed cardiac event data in an analysis performed by external device processor 52 or control circuit processor 81. The classifications of predicted sensed events (S) and predicted undersensed events (U) are listed in columns 664 and 666 of table 650 for each of the maximum peak amplitudes 656 of the sensed cardiac event data and the respective sensitivity setting 660 or 662.

As described above, external device processor 52 may classify each of the maximum peak amplitudes 656 as a predicted sensed event or a predicted undersensed event based on a comparison of the maximum peak amplitude 656 to a sensing threshold predicted according to the alternative sensitivity setting 660 or 662. As described above, the predicted value of the sensing threshold may be determined by processor 52 at the time of the sensed event using the preceding maximum peak amplitude, the sensed event interval and according to the alternative sensitivity setting. The predicted sensing threshold may be compared to the maximum peak amplitude to classify the maximum peak amplitude as a predicted sensed or undersensed event.

To illustrate, the VF4 event is sensed at an RRI of 242 ms and is determined to have a maximum peak amplitude of 1.19 mV. The processor 52 may determine the starting sensing threshold based on the preceding maximum peak amplitude of the VF3 event, which is 1.7 mV. If the percentage of the maximum peak amplitude used to set the starting threshold is 62.5%, the starting threshold in this example would be 1.06 based on the preceding maximum amplitude. For the alternative test sensitivity 0.9 mV, the sensing threshold is held at the starting sensing threshold of 1.06 for the sense delay interval 362, which may be 360 ms according to an example given above. Since the VF4 event is sensed at an RRI of 242 ms, the processor 52 determines the predicted sensing threshold at the approximate time of the maximum peak amplitude as being 1.06 mV for a sensitivity setting of 0.9 mV. Since the maximum peak amplitude of the VF4 event is 1.19 mV, greater than the predicted sensing threshold of 1.06 mV, the processor 52 determines the VF4 event as a predicted sensed event for the sensitivity setting of 0.9 mV, as indicated by an "S" in column 664.

Using the same VF4 event as an example for the alternative test sensitivity setting of 1.2 mV 662, the processor 52 determines that the starting sensing threshold of 1.06 mV based on the preceding maximum peak amplitude of 1.7 mV is less than the sensitivity setting. As a result, processor 52 determines the starting sensing threshold to be equal to the sensitivity setting of 1.2 mV since the sensitivity setting is the sensing "floor," the lowest possible sensing threshold as illustrated in FIG. 8. The starting sensing threshold set to the sensitivity setting of 1.2 mV would be held until a sensing threshold crossing occurs. Therefore, at 242 ms after the preceding VF3 event, the predicted sensing threshold is 1.2 mV. Since the maximum peak amplitude of the VF4 event is 1.19 mV, less than the predicted sensing threshold, processor 52 determines the VF4 event as a predicted undersensed event for the sensitivity setting of 1.2 mV, as indicated by a "U" in column 666.

Based on the predicted sensed and undersensed event classifications, processor 52 may determine when a VF detection 670 is predicted according to the alternative sensitivity settings 660 and 662. As described above, processor 52 may determine predicted sensed event intervals and count the predicted sensed event intervals that fall into the VF interval range. In the example shown in FIG. 12, VF is actually detected when 22 VF intervals are detected as indicated at 672. According to sensitivity setting 0.9 mV 660, the VF5, VF6, VF24 and VF25 events are predicted undersensed events. As a result, a long predicted sensed event interval is determined from the predicted sensed VF4 event until the next predicted sensed VF7 event and from the predicted sensed VF23 event to the predicted sensed VF26 event. To illustrate, the intervening RRIs of the VF5 and VF6 events would be added to the VF7 RRI to determine a predicted RRI of 733 ms for the predicted sensed VF7 event (since the most recent predicted sensed VF4 event). Since the predicted RRI of 733 ms is greater than a VT or VF interval, the VF7 event is a predicted VS event when the sensitivity setting is 0.9 mV. None of the VF5, VF6 and VF7 events, which were each counted as VF events for the actual programmed sensitivity setting of 0.075 mV, are counted as VF events by processor 52 for the test setting of 0.9 mV.

In some examples, instead of using only an "S" or a "U" to denote predicted sensed and undersensed events, processor 52 may generate VF, VT, VS or U labels to denote predicted sensed VF events, predicted sensed VT events, predicted sensed VS events and predicted undersensed events, respectively, based on both the comparison of the predicted sensing threshold to the maximum peak amplitude and the predicted sensed event interval since the most recent preceding predicted sensed event compared to the programmed VT and VF interval ranges. Furthermore, table 650 may include predicted sensed event intervals determined by and output by processor 52 in addition to an indication of predicted sensed and undersensed events.

In the example of FIG. 12, if the programmed NID to detect VF is set to 22 VF intervals, processor 52 may determine that VF is predicted to be detected upon the VF28 event, at 674, for the 0.9 mV sensitivity setting. The delay in the predicted VF detection at VF28 267 from the actual VF detection at the VF22 event 672 results from the long predicted sensed event intervals from VF4 to VF7 and from VF23 to VF26. Processor 52 may sum all the event intervals from the first predicted sensed VF1 event until the VF28 event meeting VF detection criteria to determine a predicted VF detection time.

According to sensitivity setting 1.2 mV 662, the VF4, VF5, VF6, VF18, VF19, VF21, VF22, VF24, VF25, VF27, VF28 and VF29 events are predicted undersensed events. Multiple predicted sensed event intervals that are longer than VT/VF detection intervals, are determined by processor 52 from VF3 to VF7, VF17 to VF20, and VF20 to VF26. As a result, processor 52 may predict that VF is not detected (ND) 676 when the sensitivity setting is 1.2 mV based on a count of predicted sensed events occurring at predicted sensed event intervals that are less than the programmed VF detection interval.

FIG. 13 is a diagram 700 of data that may be generated by processor 52 and displayed by display unit 54 of external device 40 according to another example. In this example, processor 52 may generate a predicted time to tachyarrhythmia detection 704 (in seconds, s) determined by processor 52 based on evaluating sensed cardiac event data according to multiple sensitivity settings 702 (in millivolts, mV). The programmed sensitivity setting 0.15 mV may be highlighted in the display as shown by dashed box 706. In other examples, the programmed sensitivity setting used to obtain the sensed cardiac event data may be highlighted in the display by enlarged or bolded font, underlining, colored font or other stylized font or by cell shading or colored fill to distinguish the programmed sensitivity setting from sensitivity settings applied to the sensed cardiac event data during the analysis. The data shown in diagram 700 may be generated from sensed cardiac event data acquired by ICD 14 during a tachyarrhythmia induction, e.g., during a VF induction. The actual time to detect the VF is 7 seconds when the programmed sensitivity is 0.15 mV in this example.

Since maximum peak amplitude and sensed event interval data is only available for R-waves and fibrillation waves actually sensed at the programmed 0.15 mV sensitivity, predicted sensed events and predicted sensed event intervals need not be determined by processor 52 at lower sensitivities, e.g., 0.075 and 0.1 mV. Any undersensed R-waves or fibrillation waves that occur at the 0.15 mV sensitivity are unknown. Accordingly, processor 52 may generate an assumed time to detect VF for alternative sensitivity settings that are less than the programmed sensitivity setting. Processor 52 may generate a predicted time to detect VF that is equal to or less than the actual time to detect VF, less than or equal to 7 seconds in this example. Any undersensed events at 0.15 mV sensitivity may be sensed at the lower sensitivity settings, potentially resulting in an earlier time to detection. Thus, the time to detect VF is displayed as equal to or less than 7 ms in the example of FIG. 12.

The time to detect VF at alternative higher sensitivity settings, greater than 0.15 mV in this example, may be estimated by processor 52 by determining predicted sensed event intervals based on classifying each of the maximum peak amplitudes of the sensed cardiac event data as sensed or undersensed events according to each of the alternative higher sensitivity settings, e.g., using the techniques described above. In the illustrative example, the time to detect the induced VF is predicted to be increased from 7 seconds at the programmed sensitivity of 0.15 mV to 10 seconds at 0.2 mV sensitivity, 11 seconds at mV sensitivity, 12 seconds at 0.45 mV and at 0.6 mV sensitivity and 15 seconds at 0.9 mV sensitivity. When the maximum alternative sensitivity setting of 1.2 mV is applied by processor 52 to the sensed cardiac event data, the predicted sensed event intervals determined by processor 52 do not reach VF detection criteria (e.g., NID not reached) and result in no VF detection. Based on the displayed data, a user may select a sensitivity to be programmed into ICD 14 which has an acceptable time to detection based on the data listed in diagram 700.

FIG. 14 is a diagram 710 of an alternative data table that may be displayed by display unit 54 from data generated by processor 52. In this example, instead of displaying a time to detection determined by processor 52 based on each sensitivity setting 712, processor 52 may generate data for display by display unit 54 indicating whether an induced VF (or other induced or spontaneous tachyarrhythmia) is predicted to be detected, yes (Y) or no (N), as indicated by column 714, for each available sensitivity setting 712. Processor 52 may determine predicted sensed event intervals for each of the alternative, sensitivity settings that are higher than the programmed setting, which may be the lowest setting of 0.075 mV in this example, and determine if VF is detected or not based on the predicted sensed event intervals. A clinician may be most concerned as to whether or not the tachyarrhythmia is detected and less concerned about whether the time to detection is increased by a few seconds.

In some examples, processor 52 may determine a sensing safety margin 715 based on predicted VF detections for display in a GUI on display unit 54. The sensing safety margin may be determined as the factor between the highest sensitivity setting at which tachyarrhythmia detection is predicted to occur and a given sensitivity setting. In the example shown, the highest sensitivity setting that VF detection is predicted to occur is a sensitivity setting of 0.9 mV, which is defined to be a 1× safety margin. At half of the 0.9 mV sensitivity setting, 0.45 mV, the safety margin for VF detection is 2×. At one-third of the highest sensitivity setting at which VF detection is predicted, 0.3 mV, the safety margin for detecting VF is 3×. The safety margin for VF detection is greater than 4× for sensitivity settings of 0.2 mV or less when the highest sensitivity setting resulting in VF detection is 0.9 mV.

A clinician may desire at least a 2× safety margin or at least a 3× safety margin for sensing VF. Accordingly, a visual representation of the predicted safety margin for detecting a tachyarrhythmia according to predicted sensed events may be included in a GUI to inform the user of acceptable sensitivity settings. In the example shown, a 3× safety margin may be recommended. As such, the sensitivity setting of 0.3 mV corresponding to a 3× safety margin may be highlighted in a display of the data of diagram 710, e.g., by outlining as shown, bolding, highlighting, colored or other stylized font, shading, colored fill or other formatting.

The data tables shown in FIGS. 13 and 14 may be displayed as part of an overall GUI that presents a visual representation of sensed cardiac event data, predicted sensed/undersensed events, and/or predicted arrhythmia detections which may include a corresponding cardiac electrical signal recording, sensed event markers, sensed event intervals, tachyarrhythmia detection time, therapy delivered, alternative sensitivity settings (or other sensing threshold control parameters), predicted sensed event intervals, predicted time of arrhythmia detections, predicted safety margins, and/or predicted therapy response.

Figure 15:
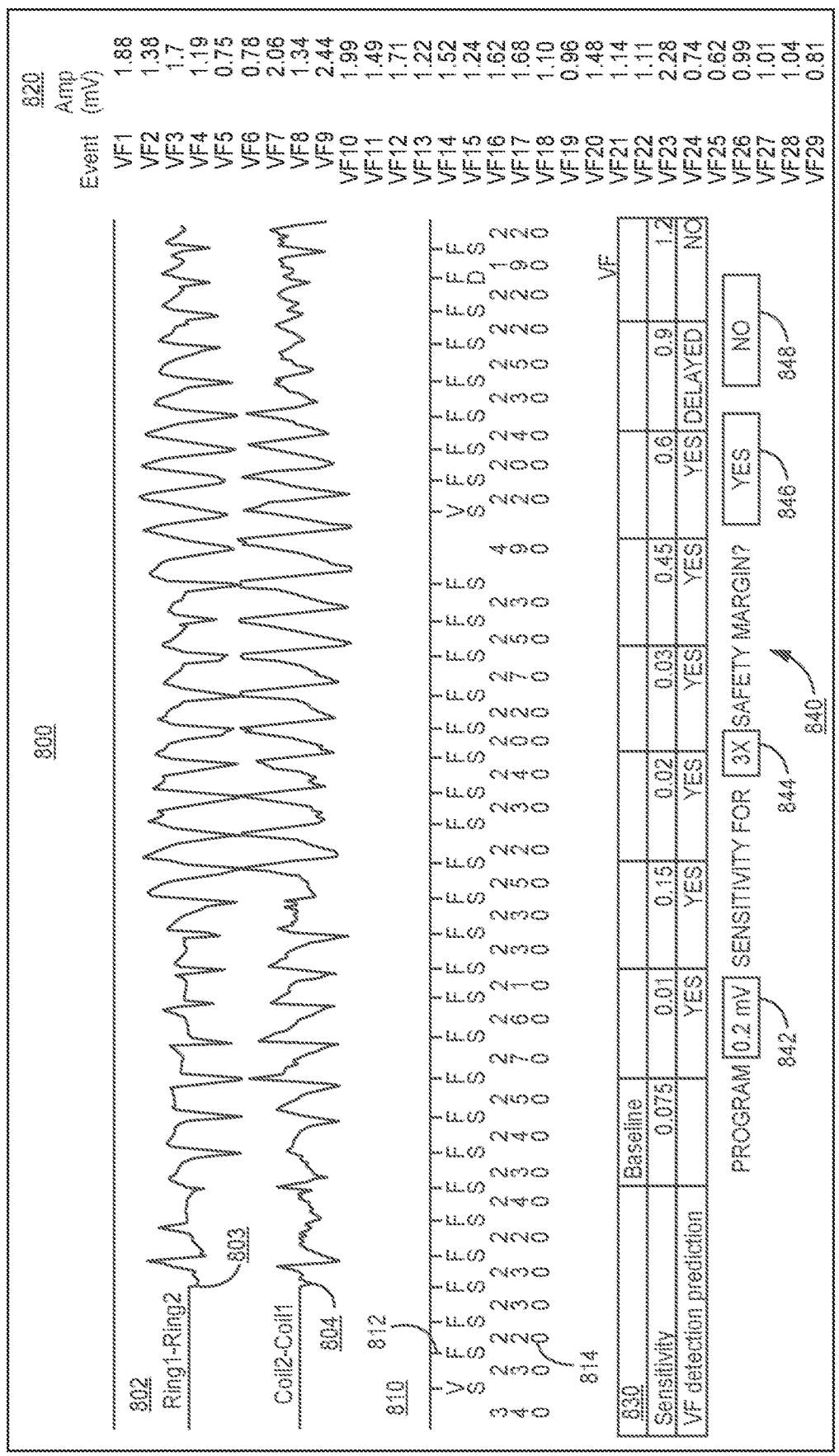
FIG. 15 is a diagram of a graphical user interface (GUI) that may be generated as output for display on a display unit according to one example.

FIG. 15 is a diagram of a GUI 800 that may be generated based on data output at block 518 of FIG. 10 by external device processor 52 according to one example. GUI 800 is displayed on display unit 54. In some examples, display unit 54 of external device 40 is a touch-sensitive screen that is configured to both display GUI 800 to a user as well as provide touch-sensitive regions of GUI 800 that allow the user to provide input to GUI 800. In other examples, a user may navigate to different user input portions of GUI 800, e.g., selectable windows, pop-up-windows, menus, icons, buttons or the like, using a mouse, keyboard or other user interface input device.

GUI 800 may include display of a cardiac electrical signal window 802, a timing diagram window 810, sensed cardiac event data table 820 and an analysis results window 830. In a cardiac electrical signal window 802 of GUI 800, one or more cardiac electrical signals 803 and 804 may be displayed. In the example shown, two wideband filtered ECG signals sensed using two different sensing electrode vectors are shown. The two wideband filtered ECG signals may be output from wideband filter 74 of sensing circuit 86. Signal 803 is labeled Ring1-Ring2 and may correspond to the signal sensed using electrodes 28 and 30 as shown in FIG. 1A. Signal 804 is labeled Coil2-Coil1 and may correspond to the signal sensed using defibrillation electrodes 24 and 26 as shown in FIG. 1A.

The sensed cardiac event table 820 includes a listing of sensed cardiac events (numbered VF1 through VF29) and corresponding maximum peak amplitude of each sensed cardiac event. The data in table 820 represents sensed cardiac event data that may be received by external device 40 from ICD 14. The data in table 820 may include sensed event intervals, as shown in FIG. 12, in some examples. The sensed cardiac event data of table 820 represents the maximum amplitude of cardiac events that are sensed by sensing circuit 86 from the narrowband filtered and rectified signal received by cardiac event detector 66. As such, the displayed wideband filtered, non-rectified ECG signals 802 and 804 may not necessarily be the signal from which the sensed cardiac event data is determined but may be the ECG signals output by sensing circuit 86 corresponding in time to the narrowband filtered, rectified signal from which the sensed cardiac event data is determined.

The timing diagram window 810 may display additional sensed cardiac event data by including sensed event intervals 814 determined between consecutive sensed events represented in table 820. The ECG signals 803 and 804 may be displayed to enable a clinician to verify the sensed cardiac event data represented in timing diagram window 810. As such, timing diagram window 810 may be aligned in time with the cardiac electrical signals 803 and 804 to provide a visual representation of sensed event signals generated by cardiac event detector 66, represented by sense event markers 812, and the corresponding sensed event intervals 814 between each consecutive pair of sense event markers 812.

In timing diagram 810, each marker 812 and sensed event interval 814 (in milliseconds) is generated by processor 52 to indicate the time of a cardiac event sensing threshold crossing by the narrowband filtered, rectified signal received by cardiac event detector 86. The sensed event marker 812 and sensed event intervals 814 represent the actual sensed cardiac event data received from ICD 14 in this example, however, in other examples, timing diagram window 810 may include multiple rows of sensed cardiac event markers 812, with each additional row displaying predicted sensed event makers generated by processor 52 according to alternative sensing control parameter settings, e.g., according to different sensitivity settings. Each row of predicted sensed event markers may include corresponding predicted sensed event intervals.

In the example shown, the analysis results window 830 includes a baseline sensitivity 0.075 mV and each available sensitivity setting (0.1 mV through 1.2 mV) greater than the baseline sensitivity. During the VF induction, the programmed sensitivity used by ICD 14 in obtaining sensed cardiac event data may be the lowest sensitivity setting of 0.075 mV. The analysis results window 830 includes a visual representation of predicted VF detection for each sensitivity setting. The visual representation may include a "yes," "no," or "delayed" indicator that indicates that VF detection is predicted, not predicted, or predicted but at a later time than the actual VF detection made at the baseline sensitivity. In some examples, the visual representation may include a color coded cell fill or text indicating acceptable and/or recommended sensitivity settings and/or unacceptable or non-recommended sensitivity settings.

For example, the VF detection prediction cells corresponding to sensitivity settings of 0.1 to 0.6 mV may be filled green to indicate acceptable sensitivity settings with predicted VF detection at the same time (or within an acceptable time limit) of the actual VF detection at the baseline 0.075 mV sensitivity. A VF detection prediction cell corresponding to a sensitivity setting (0.9 mV in this example) at which VF detection is predicted but at a delayed time from the actual VF detection may be filled yellow to indicate the sensitivity setting is a non-recommended setting. The VF detection prediction cell corresponding to a sensitivity setting (1.2 mV in this example) resulting in no predicted VF detection may be filled red to indicate an unacceptable setting. In other examples, the VF detection prediction cells may list the predicted time to detect and/or a predicted VF detection safety margin as a visual representation of the predicted performance of ICD 14 in detecting VF according to different sensitivity settings.

GUI 800 may include a user input region 840. Processor 52 may generate a recommended sensitivity setting 842 corresponding to a desired VF detection safety margin 844. A user may select "yes" button 846 to accept and program the recommended sensitivity setting 842 (or "no" button 848 to reject and not program the recommended setting). In some examples, the recommended sensitivity setting 842 is a scrollable or drop down menu that enables a user to select different sensitivity settings. Processor 52 may determine and adjust the corresponding safety margin 844 displayed for a user selected sensitivity setting 842. Additionally or alternatively, the safety margin 844 may be a scrollable or drop down menu that enables a user to select different desired safety margins. Processor 52 may determine and adjust the displayed sensitivity setting 842 that corresponds to a user selected safety margin. The user may select the sensitivity 842 or the safety margin 844 and click on the "yes" button 846 to select and program the displayed sensitivity 842 and safety margin 844. In some examples, when the user clicks the "no" button 848, the processor 52 may generate an alternative recommended sensitivity setting 842 and corresponding safety margin 844 for display in user input region 840 to enable the user to accept or reject an alternative sensitivity setting.

The user input region 840 may include a programming pop-up window displayed in response to a user clicking on the "yes" button 846. The pop-up window may be a programming confirmation window that indicates the selected programmable sensitivity setting and include "confirm" and "cancel" user inputs for confirming or cancelling the programming of the selected sensitivity setting in ICD 14. In response to a user input confirmation of a sensing control parameter setting, e.g., sensitivity setting, processor 52 may generate a programming command for transmission to ICD 14 via telemetry unit 58.

While not explicitly shown in GUI 800, other user input portions of GUI 800 may include zoom in and zoom out buttons for viewing cardiac electrical signal window 802 and/or timing diagram 810 at different horizontal time resolutions and, in the case of cardiac electrical signal window 802, vertical voltage scale resolution. Other user input portions of GUI 800 may include a pause, fast forward, reverse, store, download, save, print or other operational buttons that enable a user to view, print and/or save data displayed in GUI 800 as desired.

The GUI 800 shown in FIG. 15 illustrates data that may be included in a GUI generated for display by display unit 54. In other examples, GUI 800 may include less data or more data than shown in FIG. 15. For example, display of the cardiac electrical signals 803 and 804 may be optional. In some examples, timing diagram 810 is omitted with sensed cardiac event data presented in table 820, which may include sensed event intervals for each corresponding maximum peak amplitude. In other examples, only table 820 may be shown in GUI 800 or only timing diagram 810 may be shown instead of both.

GUI 800 may include other patient-related data such as a patient name, birthdate or other identification (not shown in FIG. 15). GUI 800 may further include other informational data such as a display of the date and time that a cardiac electrical signal episode was recorded by ICD 14 (when transmitted at a later time), therapy delivered, therapy outcome, or the like. GUI 800 may include more or fewer user input portions and/or more or fewer data windows, tables, etc. than shown in FIG. 15.

Accordingly, the techniques set forth herein provide specific improvements to the computer-related field of programming medical devices that have practical applications. For example, the use of the techniques herein may enable external device 40 to generate visualizations of sensed cardiac event data, predicted sensed cardiac events and/or predicted detected arrhythmias, and/or predicted sensed cardiac event interval data corresponding to multiple sensing control parameter settings that define the cardiac event sensing performed by ICD 14. Such visualizations may enable an external device, such as external device 40, to inform a user as to how the ICD 14 is expected to perform in sensing cardiac events according to a variety of sensing control parameter settings without requiring ICD 14 to be reprogrammed to perform actual cardiac event sensing and arrhythmia detection according to the variety of sensing control parameter settings.

By providing the GUI 800 or other user interface for displaying the data relating to predicted sensed cardiac events, the likelihood of human error in predicting cardiac event sensing and arrhythmia detection performance by ICD 14 and in determining and programming sensing control parameters is reduced. The displayed data provides a higher confidence in safely programming a higher sensitivity setting than the currently programmed sensitivity setting based on predicted sensed cardiac events and predicted tachyarrhythmia detections. By programming a higher sensitivity setting that is associated with a desired safety margin, ICD performance in detecting arrhythmias with a high degree of sensitivity and specificity is promoted while avoiding false tachyarrhythmia detections. Furthermore, the techniques disclosed herein may reduce the complexity of programming a medical device to sense cardiac events to the degree of accuracy required for controlling the delivery and timing of cardiac electrical stimulation therapies, e.g., pacing and/or CV/DF therapies. As such, the techniques disclosed herein may enable a medical device, such as ICD 14, to be programmed to sense cardiac events in a manner that is simplified, flexible, and patient-specific such that the ICD may reliably sense cardiac events to control delivery and timing of therapies.

Figure 16:
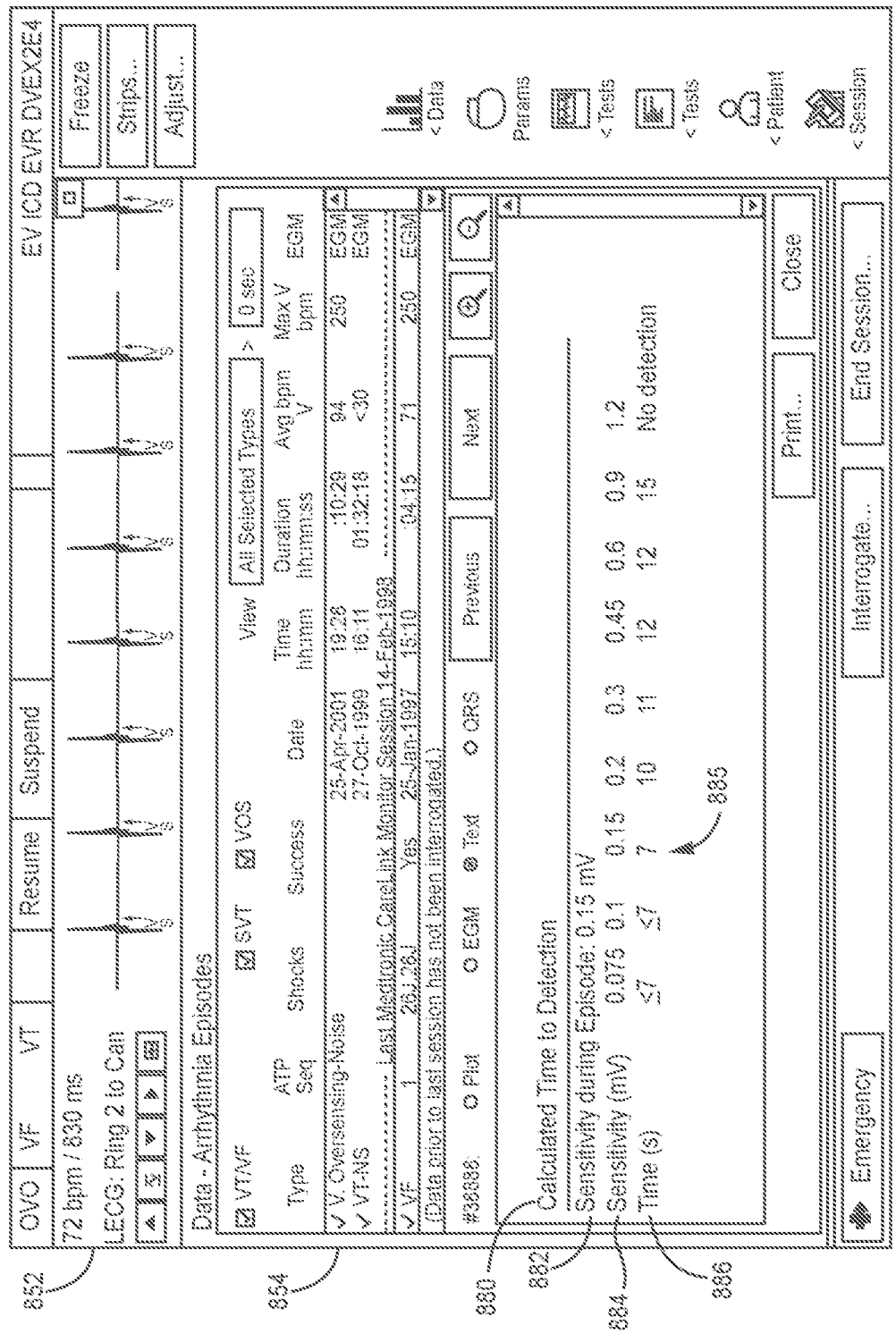
FIG. 16 is a diagram of a GUI including data generated by a processor from a sensing control parameter analysis of sensed cardiac event data according to another example.

FIG. 16 is a diagram 850 of a GUI that may be generated for display by display unit 54 including data generated by external device processor 52 (or ICD processor 81) from the sensing control parameter analysis of sensed cardiac event data received from ICD 14 according to another example. In this example, GUI 850 includes a cardiac signal window 852 which may display a real time ECG or EGM signal received from an implanted medical device. Alternatively, the displayed cardiac signal may be a stored cardiac signal episode corresponding in time to the sensed cardiac event data represented by the analysis results presented in the analysis results window 880. A historical data/information window 854 is shown including a history of arrhythmia and/or noise detection episodes detected by the ICD 14, e.g., a ventricular oversensing of noise detection and a non-sinus VT detection in the example shown, with corresponding date and time stamps, average and maximum ventricular rates, and an indication of the most recent interrogation session with the ICD 14.

The analysis results window 880 in this example displays a calculated time to detection table representing the actual time to detect a tachyarrhythmia 885 for the programmed sensitivity setting 882 and the predicted time to detect 886 for all other available sensitivity settings 884. Note that the predicted times to detect for sensitivity settings less than the programmed sensitivity setting 882 are listed as equal to or less than the actual time to detect 885, since any R-waves or fibrillation waves undersensed at the programmed sensitivity setting of 0.15 mV (in this example) are unknown and excluded from the sensed cardiac event data.

The predicted times to detect 886 listed for sensitivity settings 884 that are higher than the programmed sensitivity setting of 0.15 mV (in this example) are determined by processor 52 using the techniques described above. For example, processor 52 may receive the maximum peak amplitude of each sensed cardiac event and an associated time stamp or sensed event interval as sensed cardiac event data from ICD 14. Processor 52 may predict the value of the sensing threshold at each associated time stamp or sensed cardiac event interval using the most recent preceding maximum peak amplitude and according to sensing threshold control parameters, e.g., as described in conjunction with FIG. 8, and compare the predicted sensing threshold value to the associated maximum peak amplitude to classify each maximum peak amplitude as either a predicted sensed event or a predicted undersensed event.

Processor 52 may determine predicted sensed event intervals between all consecutive pairs of predicted sensed events and count the predicted sensed event intervals that fall into a tachyarrhythmia interval range. Processor 52 may determine if the count of predicted tachyarrhythmia sensed event intervals reaches an NID and sum the predicted sensed event intervals that occur from the first predicted tachyarrhythmia sensed event interval to and including the last predicted tachyarrhythmia sensed event interval that reaches the NID. This sum of the predicted sensed event intervals may be rounded or truncated and displayed as the time to detect in analysis results window 880. When the NID is not reached, an indication of "no detection" is displayed, as observed for the sensitivity setting of 1.2 mV. While not shown explicitly in FIG. 16, the analysis results window may include a programming user input feature or icon to enable the user to select a desired sensitivity setting for programming into ICD 14 based on the data displayed, as generally described above in conjunction with FIG. 15.

Various user input icons or buttons may also be displayed in GUI 850 as shown allowing a user to interact with the GUI using a touch screen, mouse, or other pointing tool or user interface device, e.g., to select different screens for display on display unit 54 which may include a programmable parameters display, select text or graphical versions of the displayed data, print or save displayed data, interrogate ICD 14, end the programming and interrogation session or the like.

Figure 17:
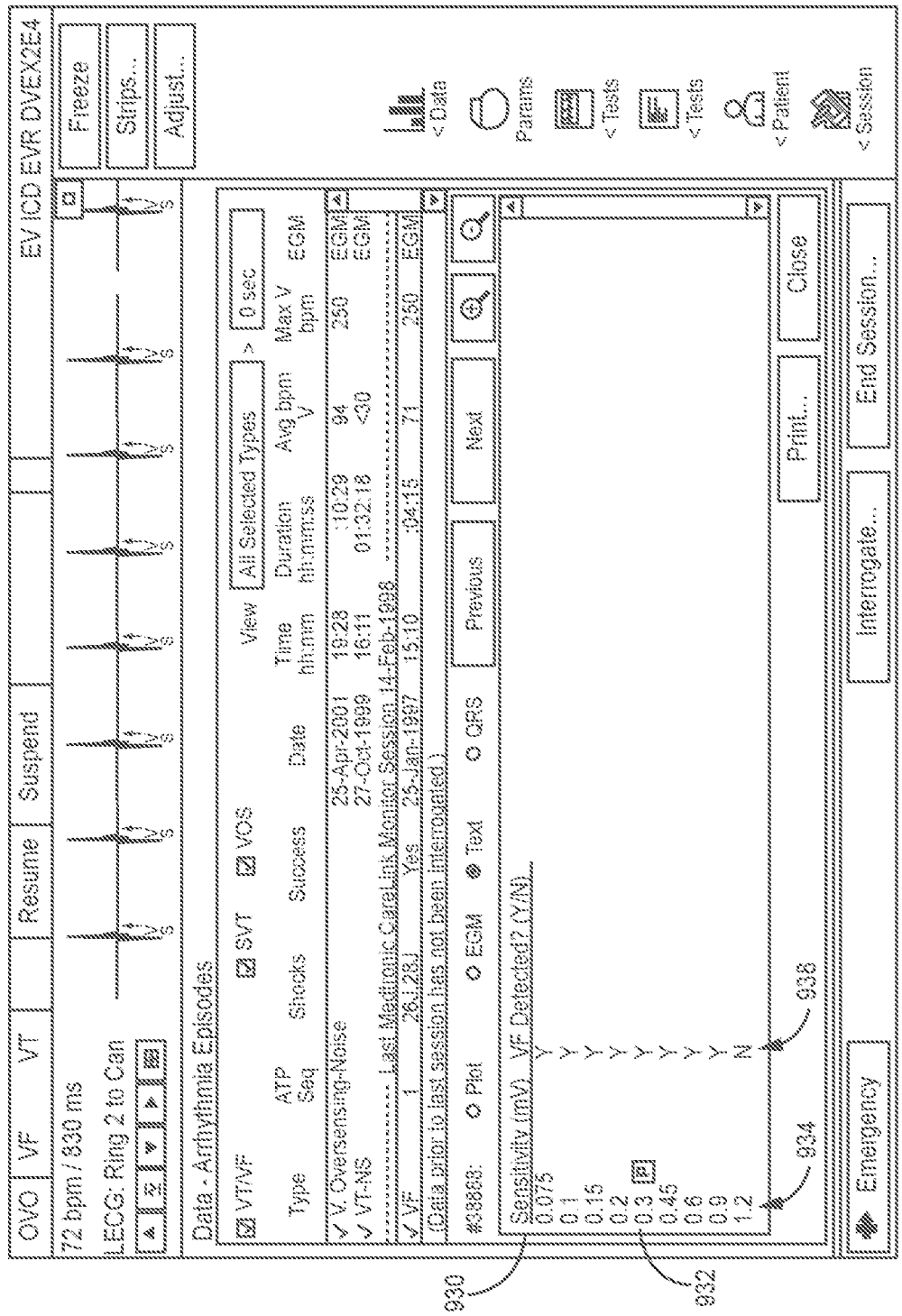
FIG. 17 is a diagram of a GUI including a visual representation of data generated by a processor according to another example.

FIG. 17 is a diagram 900 of a GUI that may be displayed by display unit 54 including data generated by processor 52 according to another example. In this example, the analysis results window 930 includes a vertical tabular listing of the available sensitivity settings 934, with the programmed sensitivity setting 932 corresponding to the actual sensed cardiac event data designated by a "P" icon. Instead of listing the predicted (or actual) time to detect for each sensitivity setting, predicted VF detections 938 (and the actual VF detection for the programmed sensitivity setting) are designated as a "yes" (Y) or a "no" (N). In this example, no VF detection is predicted for the highest sensitivity setting 1.2 mV. In some examples, a clinician may not be concerned with differences in times to detect and is primarily concerned with whether or not detection is predicted in selecting sensing control parameters.

Figure 18:
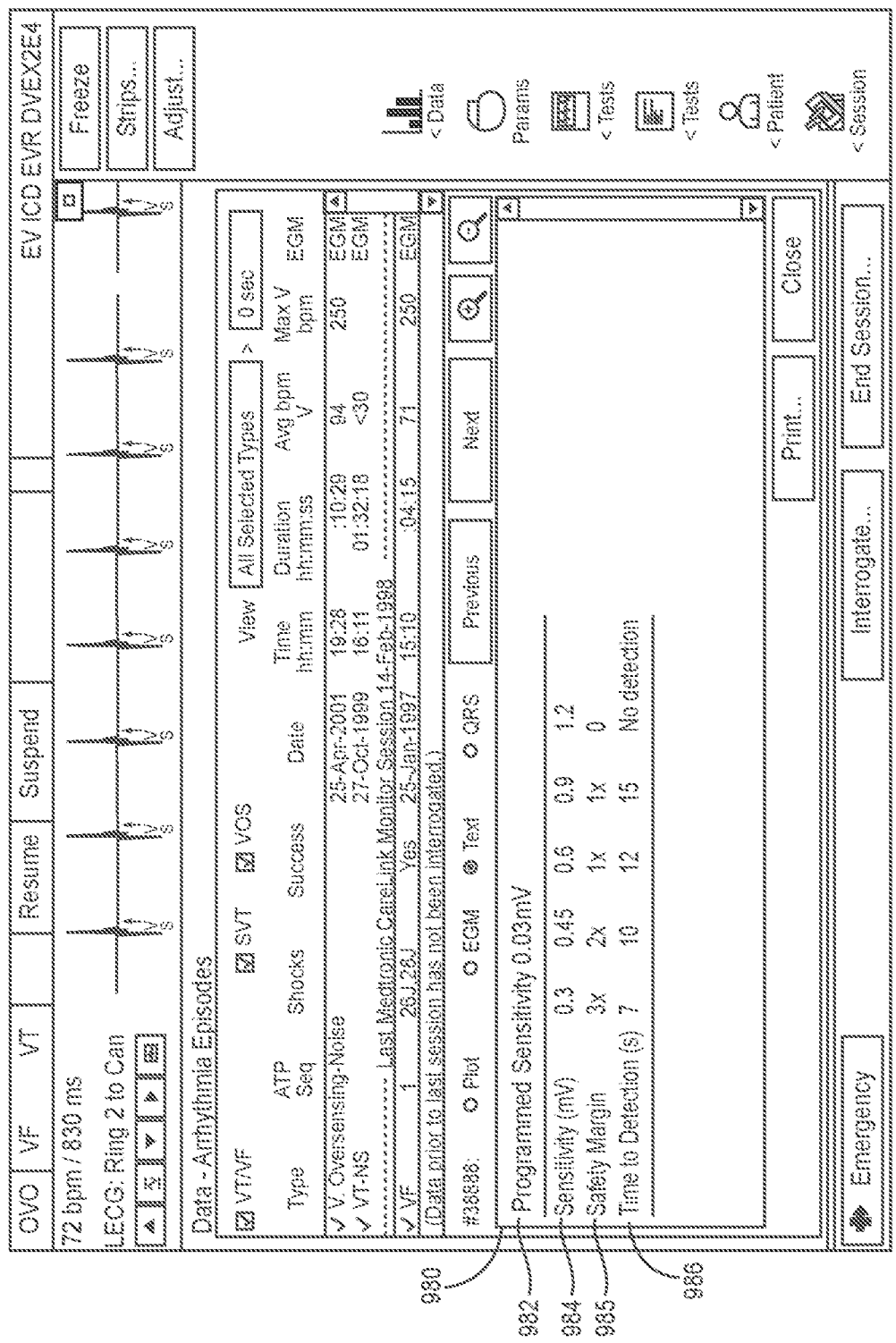
FIG. 18 is a diagram of a GUI including a visual representation of data generated by a processor according to yet another example.

FIG. 18 is a diagram 950 of a GUI that may be generated for display by display unit 54 including predicted sensed event related data generated by processor 52 according to yet another example. In this example, the analysis results window 980 includes a table indicating the programmed sensitivity setting 982, a listing of only higher available sensitivity settings 984 that are greater than the programmed sensitivity setting 982, corresponding predicted (and actual) times to VF detection 986 and the safety margin 985 determined by processor 52 for each sensitivity setting 984. Available sensitivity settings less than the programmed sensitivity setting may be omitted from the analysis results window 980 in some examples since the predicted times to detect are not determined by processor 52 by way of predicting sensed cardiac events. The predicted times to detect for lower sensitivity settings may be assumed and are predicted to be equal to or less than the actual time to detect for the programmed sensitivity setting.

As described above, processor 52 may determine the safety margin as the factor of the highest sensitivity at which detection occurs divided by a given sensitivity setting. The safety margin for the highest sensitivity setting at which VF detection is predicted is set as 1×. The safety margin for each lower sensitivity setting may be set to the rounded or truncated factor of the highest sensitivity setting at which VF detection is predicted divided by the lower sensitivity setting.

In some examples, the sensitivity settings 984 corresponding to at least a 2× safety margin may be highlighted as acceptable sensitivity settings, e.g., by colored, highlighted or other stylized font or formatting. The sensitivity setting corresponding to a recommended safety margin, e.g., 3×, may be distinguished from acceptable sensitivity settings by different stylized font or formatting, cell color or fill, highlighting, etc. As indicated above, the analysis results window 980 may include a user input button or region to accept and enable programming of a recommended sensitivity setting.

Figure 19:
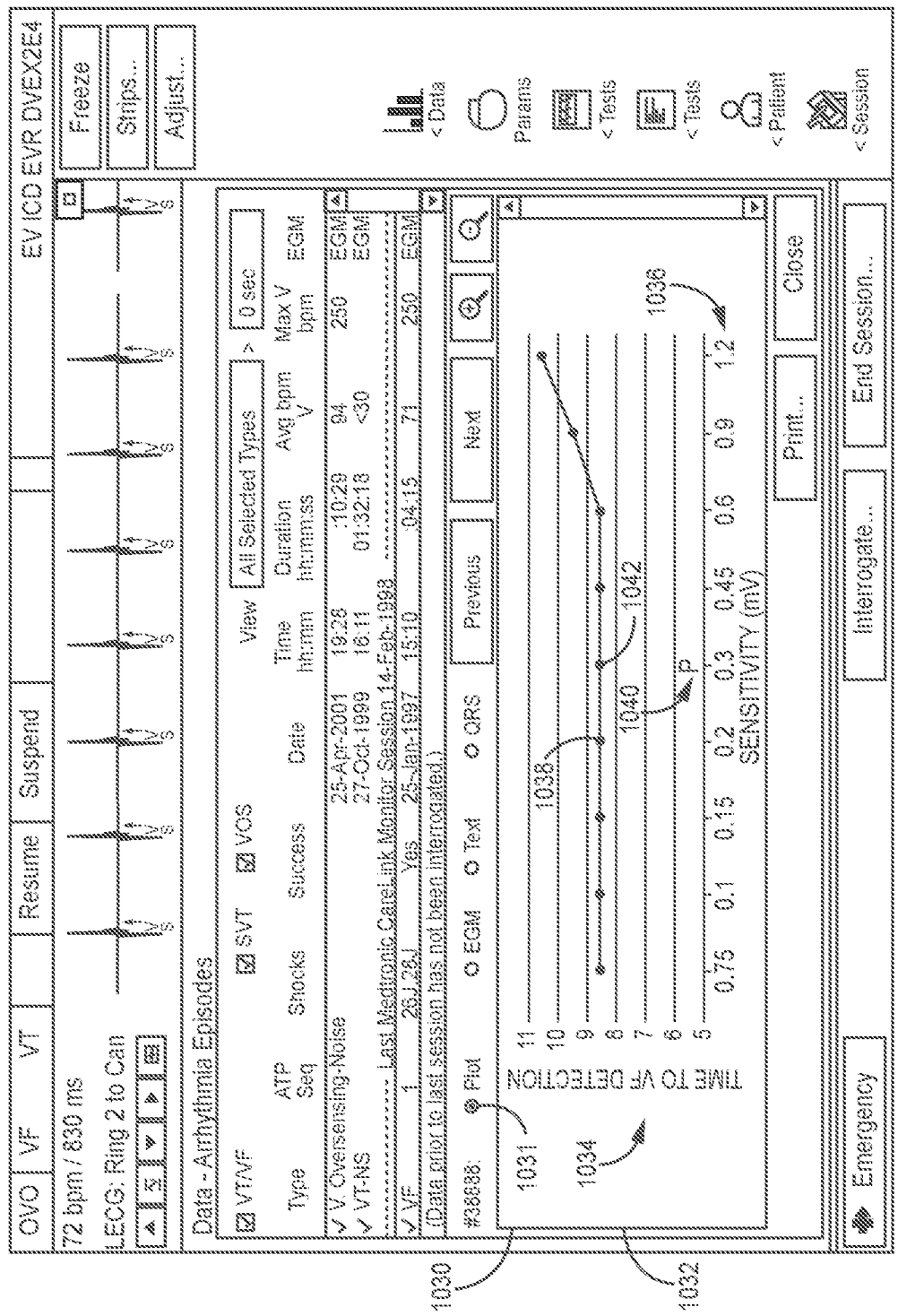
FIG. 19 is a diagram of a GUI including a visual representation of data generated by a processor according to yet another example.

FIG. 19 is a diagram 1000 of a GUI that may be generated for display by display unit 54 including predicted sensed event related data generated by processor 52 according to yet another example. The analysis results window 1030 in this example includes a graph 1032 of the sensing control parameter analysis results of the sensed cardiac event data instead of a tabular or text display as shown in FIGS. 15-17. A user may toggle between a plotted graphical display and a text or table display of the data using user input selection buttons 1031 in some examples. When "plot" 1031 is selected, the predicted times to VF detection 1038 may be graphed along the y-axis 1034 for each available sensitivity setting plotted along the x-axis 1036. The actual programmed sensitivity setting 1040 may be indicated by a "P" icon with the corresponding actual time to VF detection 1042. Various formatting techniques may be used to highlight the programmed and recommended or acceptable and/or non-recommended or unacceptable sensitivity settings in the graph 1032. For example, all settings resulting in at least a 2× safety margin may be shown by a green plot symbol. A setting resulting in a desired safety margin, e.g., 3×, may be displayed as an enlarged plot symbol and/or with an "R" icon or labeled as 3× safety margin. All sensitivity settings resulting in a 1× safety margin may be displayed as non-recommended settings indicated by a yellow plot symbol and/or an "X" plot symbol instead of a circle "O," for example. Any sensitivity setting resulting a prediction of no VF detection may be distinguished as an unacceptable setting by a red plot symbol and/or an "X" plot symbol or be shaded or darkened compared to other plotted symbols or left out altogether to indicate that this setting should not be programmed. As generally described above, the analysis results window 1030 may include a user input region enabling a user to select a sensitivity setting for programming into ICD 14.

While the techniques described herein generally refer to processor 52 receiving sensed cardiac event data transmitted from ICD 14, it is contemplated that processor 52 may determine sensed cardiac event data from a received cardiac electrical signal and perform the subsequent analysis of the sensed cardiac event data according to different sensing control parameter settings. The sensed cardiac event data may be determined by processor 52 from a cardiac electrical signal received by external device 40 via sensing electrodes coupled to external device 40, e.g., carried by lead 16 and coupled via alligator clips and wires or other electrical connectors. Alternatively, the sensed cardiac event data may be determined by processor 52 from a cardiac signal transmitted from ICD 14 (or another implantable medical device).

In still other examples, ICD control circuit 80 may perform the sensed cardiac event analysis described herein and transmit data of the analysis results to external device via telemetry circuit 88. Processor 52 may generate output based on the received data for display by display unit 54. In some examples, control circuit 80 may additionally or alternatively adjust the programmed sensitivity to a different setting based on the results of the sensed cardiac event data. As such, a single medical device processor may perform the methods disclosed herein for receiving sensed cardiac event data, analyzing the sensed cardiac event data according to at least one different sensing control parameter settings and generating an output, which may include a programming command and/or data for display in a GUI.

It should be understood that, depending on the example, certain acts or events of any of the methods described herein can be performed in a different sequence, may be added, merged, or left out altogether (e.g., not all described acts or events are necessary for the practice of the method). Moreover, in certain examples, acts or events may be performed concurrently, e.g., through multi-threaded processing, interrupt processing, or multiple processors, rather than sequentially. In addition, while certain aspects of this disclosure are described as being performed by a single circuit or unit for purposes of clarity, it should be understood that the techniques of this disclosure may be performed by a combination of units or circuits associated with, for example, a medical device.

In one or more examples, the functions described may be implemented in hardware, software, firmware, or any combination thereof. If implemented in software, the functions may be stored as one or more instructions or code on a computer-readable medium and executed by a hardware-based processing unit. Computer-readable media may include computer-readable storage media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPLAs), or other equivalent integrated or discrete logic circuitry. Accordingly, the term "processor," as used herein may refer to any of the foregoing structure or any other structure suitable for implementation of the techniques described herein. Also, the techniques could be fully implemented in one or more circuits or logic elements.

Thus, a medical device system has been presented in the foregoing description with reference to specific examples. It is to be understood that various aspects disclosed herein may be combined in different combinations than the specific combinations presented in the accompanying drawings. It is appreciated that various modifications to the referenced examples may be made without departing from the scope of the disclosure and the following claims.

What is claimed is:

1. A medical device system comprising:
processing circuitry configured to:
receive a first feature determined from a sensed cardiac event signal for each of a plurality of sensed cardiac event signals, where each of the plurality of sensed cardiac event signals are sensed from a cardiac electrical signal according to a first setting of a sensing control parameter;
according to a second setting of the sensing control parameter, classify each of the first features as one of a predicted sensed event or a predicted undersensed event; and
based on the first features classified as predicted sensed events according to the second setting, generate a tachyarrhythmia detection prediction associated with the second setting of the sensing control parameter; and
a display unit configured to display the tachyarrhythmia detection prediction associated with the second setting of the sensing control parameter.

2. The medical device system of claim 1 further comprising:
sensing circuitry configured to:
sense a cardiac signal; and sense the plurality of cardiac event signals according to the first setting of the sensing control parameter from the cardiac signal;

control circuitry configured to detect a tachyarrhythmia based on the cardiac event signals sensed by the sensing circuitry according to the first setting of the sensing control parameter; and a therapy delivery circuit configured to deliver a therapy in response to the tachyarrhythmia being detected by the control circuitry.

3. The medical device system of claim 2 further comprising:

an implantable medical device comprising:
a housing enclosing the sensing circuitry, the control circuitry, and the therapy delivery circuitry, wherein the sensing circuitry and the control circuitry being configured to cooperatively determine the first features; and first telemetry circuitry configured to transmit the first features event data; and an external device comprising second telemetry circuitry for receiving the transmitted first features and the processing circuitry, wherein the processing circuitry being configured to receive the first features via the second telemetry circuit.

4. The medical device system of claim 2 wherein the therapy delivery circuitry is further configured to deliver electrical stimulation to induce the tachyarrhythmia.

5. The medical device system of claim 1 wherein the processing circuitry is further configured to:

receive the first features and a sensed event time for each of the plurality of cardiac event signals sensed according to the first setting of the sensing control parameter; and classify a given one of the first features as one of a predicted sensed event or a predicted undersensed event by:

determining a predicted sensing threshold amplitude at a given one of the sensed event times corresponding to the given one of the first features, the predicted sensing threshold amplitude determined based on a most recent preceding first feature classified as a predicted sensed event;

comparing the predicted sensing threshold amplitude to the given one of the first features;

classifying the given one of the first features as a predicted sensed event in response to the given one of the first features meeting the predicted sensing threshold amplitude; and classifying the given one of the first features as a predicted undersensed event in response to the given one of the first features not meeting the predicted sensing threshold amplitude.

6. The medical device system of claim 1 wherein the processor is configured to generate the tachyarrhythmia detection prediction by:

determining predicted sensed event intervals based on the first features classified as predicted sensed events;

determining if the predicted sensed event intervals meet tachyarrhythmia detection criteria; and generating the tachyarrhythmia detection prediction as one of:

a detected tachyarrhythmia when the predicted sensed event intervals meet the tachyarrhythmia detection criteria; and an undetected tachyarrhythmia when the predicted sensed event intervals do not meet the tachyarrhythmia detection criteria.

7. The medical device system of claim 1 wherein the processing circuitry is further configured to generate the tachyarrhythmia detection prediction by determining a predicted time to detect a tachyarrhythmia based on the first features classified as predicted sensed events.

8. The medical device system of claim 1 wherein:

the processing circuitry is further configured to, for each setting of a plurality of settings of the sensing control parameter comprising the second setting:

classify each of the first features as one of a predicted sensed event or a predicted undersensed event; and determine a tachyarrhythmia detection prediction associated with the respective setting of the plurality of settings of the sensing control parameter, the tachyarrhythmia detection prediction including one of a detected tachyarrhythmia or an undetected tachyarrhythmia; and the display unit is further configured to display the tachyarrhythmia detection predictions associated with each of the plurality of settings of the sensing control parameter.

9. The medical device system of claim 8 wherein:

the processing circuitry is further configured to:

determine a least sensitive setting of the plurality of settings of the sensing control parameter associated with the tachyarrhythmia detection predictions that are detected tachyarrhythmias; and determining a safety margin for detecting tachyarrhythmia for at least one of the plurality of settings of the sensing control parameter based on the least sensitive setting associated with a tachyarrhythmia detection prediction that is a detected tachyarrhythmia; and the display unit is further configured to display the determined safety margin.

10. The medical device of claim 8 wherein:

the processing circuitry is further configured to, based on the tachyarrhythmia detection predictions, determine a recommendation for at least one setting of the plurality of settings of the sensing control parameters as being one of a non-recommended setting or a recommended setting of the sensing control parameter; and the display unit is further configured to display the at least one setting as being a recommended setting or a non-recommended setting of the sensing control parameter based on the determined recommendation.

11. A method comprising:

receiving a first feature determined from a sensed cardiac event signal for each of a plurality of sensed cardiac event signals, where each of the plurality of sensed cardiac event signals are sensed from a cardiac electrical signal by sensing circuitry according to a first setting of a sensing control parameter;

according to a second setting of the sensing control parameter, classifying each of the first features as one of a predicted sensed event or a predicted undersensed event;

based on the first features classified as predicted sensed events according to the second setting, generating a tachyarrhythmia detection prediction associated with the second setting of the sensing control parameter; and displaying the tachyarrhythmia detection prediction associated with the second setting of the sensing control parameter.

12. The method of claim 11 further comprising:
sensing a cardiac signal;
sensing the plurality of cardiac event signals according to the first setting of the sensing control parameter from the cardiac signal;
detecting a tachyarrhythmia based on the cardiac event signals sensed according to the first setting of the sensing control parameter; and
delivering a therapy in response to detecting the tachyarrhythmia.

13. The method of claim 12 further comprising:
determining the first features from the plurality of sensed cardiac event signals;
transmitting the first features by a first telemetry circuit; and
receiving the transmitted first features by a second telemetry circuit prior to classifying each of the first features as one of a predicted sensed event or a predicted undersensed event.

14. The method of claim 12 further comprising delivering electrical stimulation to induce the tachyarrhythmia.

15. The method of claim 11 further comprising:
receiving the first features and a sensed event time for each of the plurality of cardiac event signals sensed according to the first setting of the sensing control parameter; and
classifying a given one of the first features as one of a predicted sensed event or a predicted undersensed event by:
determining a predicted sensing threshold amplitude at a given one of the sensed event times corresponding to the given one of the first features, the predicted sensing threshold amplitude determined based on a most recent preceding first feature classified as a predicted sensed event;
comparing the predicted sensing threshold amplitude to the given one of the first features;
classifying the given one of the first features as a predicted sensed event in response to the given one of the first features meeting the predicted sensing threshold amplitude; and
classifying the given one of the first features as a predicted undersensed event in response to the given one of the first features not meeting the predicted sensing threshold amplitude.

16. The method of claim 11 further comprising generating the tachyarrhythmia detection prediction by:
determining predicted sensed event intervals based on the first features classified as predicted sensed events;
determining if the predicted sensed event intervals meet tachyarrhythmia detection criteria; and
generating the tachyarrhythmia detection prediction as one of:
a detected tachyarrhythmia when the predicted sensed event intervals meet the tachyarrhythmia detection criteria; and
an undetected tachyarrhythmia when the predicted sensed event intervals do not meet the tachyarrhythmia detection criteria.

17. The method of claim 11 further comprising generating the tachyarrhythmia detection prediction by determining a predicted time to detect a tachyarrhythmia based on the first features classified as predicted sensed events.

18. The method of claim 11 further comprising:
for each setting of a plurality of settings of the sensing control parameter comprising the second setting:
classifying each of the first features as one of a predicted sensed event or a predicted undersensed event; and
determining a tachyarrhythmia detection prediction associated with the respective setting of the plurality of settings of the sensing control parameter, the tachyarrhythmia detection prediction including one of a detected tachyarrhythmia or an undetected tachyarrhythmia; and
displaying the tachyarrhythmia detection predictions associated with each of the plurality of settings of the sensing control parameter.

19. The method of claim 18 further comprising:
determining a least sensitive setting of the plurality of settings of the sensing control parameter associated with the tachyarrhythmia detection predictions that are detected tachyarrhythmias; and
determining a safety margin for detecting tachyarrhythmia for at least one of the plurality of settings of the sensing control parameter based on the least sensitive setting associated with a tachyarrhythmia detection prediction that is a detected tachyarrhythmia; and
displaying the determined safety margin.

20. The method of claim 18 further comprising:
based on the tachyarrhythmia detection predictions, determining a recommendation for at least one setting of the plurality of settings of the sensing control parameters as being one of a non-recommended setting or a recommended setting of the sensing control parameter; and
displaying the at least one setting as the recommended setting or the non-recommended setting of the sensing control parameter based on the determined recommendation.

21. A non-transitory computer-readable medium storing a set of instructions which, when executed by a processor of a medical device, cause the medical device to:
receive a first feature determined from a sensed cardiac event signal for each of a plurality of sensed cardiac event signals, where each of the plurality of sensed cardiac event signals are sensed from a cardiac electrical signal according to a first setting of a sensing control parameter;
according to a second setting of the sensing control parameter, classifying each of the first features as one of a predicted sensed event or a predicted undersensed event;
based on the first features classified as predicted sensed events according to the second setting, generating a tachyarrhythmia detection prediction associated with the second setting of the sensing control parameter; and
displaying the tachyarrhythmia detection prediction associated with the second setting of the sensing control parameter.

* * * * *